(12) United States Patent
Reddy et al.

(10) Patent No.: US 11,006,631 B2
(45) Date of Patent: May 18, 2021

(54) SUBSTITUTED PYRIMIDINYLOXY PYRIDINE DERIVATIVES AS HERBICIDES

(71) Applicant: FMC Corporation, Philadelphia, PA (US)

(72) Inventors: Ravisekhara Pochimireddy Reddy, Secunderabad (IN); Nicholas Ryan Deprez, East Windsor, NJ (US); Yuzhong Chen, Wilmington, DE (US)

(73) Assignee: FMC Corporation, Philadelphia, PA (US)

( * ) Notice: Subject to any disclaimer, the term of this patent is extended or adjusted under 35 U.S.C. 154(b) by 0 days.

(21) Appl. No.: 15/551,656

(22) PCT Filed: Mar. 16, 2016

(86) PCT No.: PCT/US2016/022562
§ 371 (c)(1),
(2) Date: Aug. 17, 2017

(87) PCT Pub. No.: WO2016/149315
PCT Pub. Date: Sep. 22, 2016

(65) Prior Publication Data
US 2018/0020664 A1    Jan. 25, 2018

Related U.S. Application Data

(60) Provisional application No. 62/134,665, filed on Mar. 18, 2015.

(51) Int. Cl.
| | | |
|---|---|---|
| A01N 43/54 | (2006.01) | |
| C07D 401/14 | (2006.01) | |
| C07D 413/14 | (2006.01) | |
| A01N 43/80 | (2006.01) | |
| A01N 43/56 | (2006.01) | |
| A01N 43/647 | (2006.01) | |
| A01N 43/653 | (2006.01) | |
| A01N 43/76 | (2006.01) | |
| A01N 43/78 | (2006.01) | |
| A01N 43/82 | (2006.01) | |
| C07D 401/12 | (2006.01) | |
| C07D 417/14 | (2006.01) | |

(52) U.S. Cl.
CPC ............ *A01N 43/54* (2013.01); *A01N 43/56* (2013.01); *A01N 43/647* (2013.01); *A01N 43/653* (2013.01); *A01N 43/76* (2013.01); *A01N 43/78* (2013.01); *A01N 43/80* (2013.01); *A01N 43/82* (2013.01); *C07D 401/12* (2013.01); *C07D 401/14* (2013.01); *C07D 413/14* (2013.01); *C07D 417/14* (2013.01)

(58) Field of Classification Search
CPC ............................ C07D 413/14; A01N 43/54
See application file for complete search history.

(56) References Cited

U.S. PATENT DOCUMENTS

| | | | | |
|---|---|---|---|---|
| 3,013,054 | A | * | 12/1961 | Richter ................... C07C 59/58 560/65 |
| 4,248,619 | A | | 2/1981 | Serban et al. |
| 4,371,736 | A | | 2/1983 | Selby |
| 4,427,437 | A | | 1/1984 | Serban et al. |
| 4,460,588 | A | | 7/1984 | Serban et al. |
| 4,634,649 | A | * | 1/1987 | Knapp ............... G03G 9/08755 430/106.2 |
| 4,863,924 | A | | 9/1989 | Haga et al. |
| 5,962,685 | A | | 10/1999 | Ueda et al. |
| 9,695,155 | B2 | | 7/2017 | Sharpe et al. |
| 2009/0221547 | A1 | | 9/2009 | Gao et al. |
| 2010/0022538 | A1 | | 1/2010 | Boebel et al. |
| 2012/0252818 | A1 | | 10/2012 | Chiosis et al. |
| 2016/0333000 | A1 | | 11/2016 | Deprez et al. |
| 2017/0190671 | A1 | | 7/2017 | Reddy et al. |
| 2017/0204081 | A1 | | 7/2017 | Satterfield |

FOREIGN PATENT DOCUMENTS

| | | |
|---|---|---|
| AU | 535637 B2 | 3/1984 |
| CA | 2290379 A1 | 11/1998 |
| DE | 4438824 A1 | 4/1995 |

(Continued)

OTHER PUBLICATIONS

Machine translation of WO 94/17059 (Aug. 1994).*

(Continued)

*Primary Examiner* — John Pak
(74) *Attorney, Agent, or Firm* — FMC Corporation

(57) ABSTRACT

Disclosed are compounds of Formula 1, including all stereoisomers, N-oxides, and salts thereof,

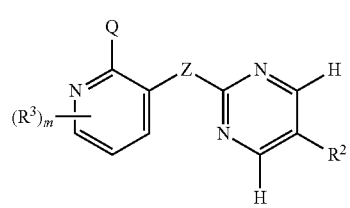

wherein Q, Z, $R^2$, $R^3$ and m are as defined in the disclosure.

Also disclosed are compositions containing the compounds of Formula 1 and methods for controlling undesired vegetation comprising contacting the undesired vegetation or its environment with an effective amount of a compound or a composition of the invention.

10 Claims, No Drawings

(56) References Cited

FOREIGN PATENT DOCUMENTS

| EP | 0 008192 A1 | 2/1980 |
|---|---|---|
| EP | 0410590 A1 | 1/1991 |
| EP | 0226104 B1 | 2/1991 |
| EP | 0665224 A1 | 8/1995 |
| GB | 2237570 B | 5/1993 |
| JP | 54-117486 | 9/1979 |
| JP | S61 236766 A | 10/1986 |
| JP | H41 08777 A | 4/1992 |
| JP | 10-251255 A | 9/1998 |
| JP | 2012/012299 A | 1/2012 |
| JP | 5753178 B2 | 7/2015 |
| WO | 84/00685 A1 | 3/1984 |
| WO | 94/17059 A1 | 8/1994 |
| WO | 96/33994 A1 | 10/1996 |
| WO | 98/40379 | 9/1998 |
| WO | 98/52938 A1 | 11/1998 |
| WO | 20070095602 | 8/2007 |
| WO | 20080009963 | 1/2008 |
| WO | 2012/039141 A1 | 3/2012 |
| WO | 2015/108779 A1 | 7/2015 |

OTHER PUBLICATIONS

Derwent Abstract 1994-264003; abstracting WO 94/17059 (Aug. 1994).*

Saito, Yoshihiro et al. "Preparation of pyrimidine derivatives as herbicides". XP002735697, retrieved from STN Database accession No. 1992:545339 abstract, CAS-RN 143437-16-5.

Selby et al., "N-Azolyl Phenoxypyrimidine Herbicides: Novel Inhibitors of Carotenoid Biosynthesis Part 1," Water-Soluble Polymers: Synthesis, Solution Properties and Applications, vol. 800, Jan. 1, 2002 (Jan. 1, 2002), pp. 74-84, XP001120637, ISBN: 978-0-541-23408-9.

Hiroshi Okada et al., "Synthesis and Antitumor Activities of Novel Benzoylphenylurea Derivatives", Chemical and Pharmaceutical Bulletin, vol. 39, No. 9, 1991, pp. 2308-2315, XP001205628, ISSN: 0009-2363.

PCT International Search Report for WO2016/149315, dated Jun. 30, 2016.

* cited by examiner

SUBSTITUTED PYRIMIDINYLOXY PYRIDINE DERIVATIVES AS HERBICIDES

CROSS-REFERENCE TO RELATED APPLICATIONS

This application is a continuation of International Application No. PCT/US2016/022562, filed on Mar. 16, 2016, which claims priority to U.S. Provisional Application No. 62/134,665, filed on Mar. 18, 2015, both of which are incorporated by reference in their entirety herein.

FIELD OF THE INVENTION

This invention relates to certain substituted pyrimidyloxy pyridine derivatives, their N-oxides, salts and compositions, and methods of their use for controlling undesirable vegetation.

BACKGROUND OF THE INVENTION

The control of undesired vegetation is extremely important in achieving high crop efficiency. Achievement of selective control of the growth of weeds especially in such useful crops as rice, soybean, sugar beet, maize, potato, wheat, barley, tomato and plantation crops, among others, is very desirable. Unchecked weed growth in such useful crops can cause significant reduction in productivity and thereby result in increased costs to the consumer. The control of undesired vegetation in noncrop areas is also important. Many products are commercially available for these purposes, but the need continues for new compounds that are more effective, less costly, less toxic, environmentally safer or have different sites of action.

SUMMARY OF THE INVENTION

This invention is directed to compounds of Formula 1 (including all stereoisomers), N-oxides, and salts thereof, agricultural compositions containing them and their use as herbicides:

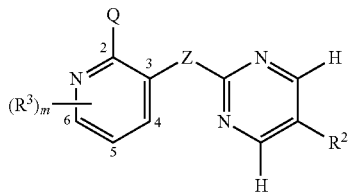

Q is a 5- or 6-membered aromatic heterocylic ring optionally substituted with 1 to 4 $R^1$;
Z is O or S;
each $R^1$ is independently halogen, cyano, nitro, $SF_5$, CHO, $C(=O)NH_2$, $C(=S)NH_2$, $SO_2NH_2$, $C_1$-$C_4$ alkyl, $C_2$-$C_4$ alkenyl, $C_2$-$C_4$ alkynyl, $C_1$-$C_4$ haloalkyl, $C_2$-$C_4$ haloalkenyl, $C_2$-$C_4$ haloalkynyl, $C_3$-$C_6$ cycloalkyl, $C_3$-$C_6$ halocycloalkyl, $C_4$-$C_8$ alkylcycloalkyl, $C_4$-$C_8$ cycloalkylalkyl, $C_2$-$C_6$ alkylcarbonyl, $C_2$-$C_6$ haloalkylcarbonyl, $C_2$-$C_6$ alkoxycarbonyl, $C_3$-$C_7$ cycloalkylcarbonyl, $C_2$-$C_8$ alkylaminocarbonyl, $C_3$-$C_{10}$ dialkylaminocarbonyl, $C_1$-$C_4$ alkoxy, $C_3$-$C_4$ alkenyloxy, $C_3$-$C_4$ alkynyloxy, $C_1$-$C_4$ haloalkoxy, $C_3$-$C_4$ haloalkenyloxy, $C_3$-$C_4$ haloalkynyloxy, $C_3$-$C_6$ cycloalkoxy, $C_3$-$C_6$ halocycloalkoxy, $C_4$-$C_8$ cycloalkylalkoxy, $C_2$-$C_6$ alkoxyalkyl, $C_2$-$C_6$ haloalkoxyalkyl, $C_2$-$C_6$ alkoxyhaloalkyl, $C_2$-$C_6$ alkoxyalkoxy, $C_2$-$C_4$ alkylcarbonyloxy, $C_2$-$C_6$ cyanoalkyl, $C_2$-$C_6$ cyanoalkoxy, $C_1$-$C_4$ hydroxyalkyl, $C_2$-$C_4$ alkylthioalkyl, $SO_nR^{1A}$, $Si(CH_3)_3$ or $B(-OC(R^{1B})_2C(R^{1B})_2O-)$; or a phenyl ring optionally substituted with up to 5 substituents independently selected from $R^{1C}$; or a 5- or 6-membered heteroaromatic ring containing ring members selected from carbon atoms and up to 4 heteroatoms independently selected from up to 2 O, up to 2 S and up to 4 N atoms, each ring optionally substituted with up to 3 substituents independently selected from $R^{1C}$ on carbon atom ring members and $R^{1D}$ on nitrogen atom ring members;
$R^2$ is halogen, cyano, nitro, $C_1$-$C_4$ alkoxy, $C_1$-$C_4$ alkyl, $C_2$-$C_6$ alkenyl, $C_2$-$C_6$ alkynyl, $SO_nR^{2A}$, $C_1$-$C_4$ haloalkyl or $C_3$-$C_6$ cycloalkyl;
each $R^3$ is independently halogen, cyano, hydroxy, nitro, amino, CHO, $C(=O)NH_2$, $C(=S)NH_2$, $SO_2NH_2$, $C_1$-$C_4$ alkyl, $C_2$-$C_4$ alkenyl, $C_2$-$C_4$ alkynyl, $C_1$-$C_4$ haloalkyl, $C_2$-$C_4$ haloalkenyl, $C_2$-$C_4$ haloalkynyl, $C_3$-$C_6$ cycloalkyl, $C_3$-$C_6$ halocycloalkyl, $C_4$-$C_8$ alkylcycloalkyl, $C_4$-$C_8$ cycloalkylalkyl, $C_2$-$C_6$ alkylcarbonyl, $C_2$-$C_6$ haloalkylcarbonyl, $C_2$-$C_6$ alkoxycarbonyl, $C_3$-$C_7$ cycloalkylcarbonyl, $C_1$-$C_4$ alkoxy, $C_3$-$C_4$ alkenyloxy, $C_3$-$C_4$ alkynyloxy, $C_1$-$C_4$ haloalkoxy, $C_3$-$C_4$ haloalkenyloxy, $C_3$-$C_4$ haloalkynyloxy, $C_3$-$C_6$ cycloalkoxy, $C_3$-$C_6$ halocycloalkoxy, $C_4$-$C_8$ cycloalkylalkoxy, $C_2$-$C_6$ alkoxyalkyl, $C_2$-$C_6$ haloalkoxyalkyl, $C_2$-$C_6$ alkoxyhaloalkyl, $C_2$-$C_6$ alkoxyalkoxy, $C_2$-$C_4$ alkylcarbonyloxy, $C_2$-$C_6$ cyanoalkyl, $C_2$-$C_6$ cyanoalkoxy, $C_2$-$C_4$ alkylthioalkyl, $Si(CH_3)_3$, $C\equiv CSi(CH_3)_3$, $C(=O)N(R^{3A})(R^{3B})$, $C(=NOR^{3C})H$, $C(=NR^{3D})H$ or $SO_nR^{3E}$; or a phenyl ring optionally substituted with up to 5 substituents independently selected from $R^{3F}$; or a 5- or 6-membered heteroaromatic ring containing ring members selected from carbon atoms and up to 4 heteroatoms independently selected from up to 2 O, up to 2 S and up to 4 N atoms, each ring optionally substituted with up to 3 substituents independently selected from $R^{3F}$ on carbon atom ring members and $R^{3G}$ on nitrogen atom ring members; or pyrimidinyloxy;
m is 0, 1, 2 or 3;
each n is independently 0, 1 or 2;
each $R^{1A}$, $R^{2A}$ and $R^{3E}$ is independently $C_1$-$C_4$ alkyl, $C_1$-$C_4$ haloalkyl, $C_1$-$C_4$ alkylamino or $C_2$-$C_6$ dialkylamino;
each $R^{1B}$ is independently H or $C_1$-$C_4$ alkyl;
each $R^{1C}$ is independently hydroxy, halogen, cyano, nitro, $C_1$-$C_6$ alkyl, $C_1$-$C_6$ haloalkyl, $C_1$-$C_6$ alkoxy or $C_1$-$C_6$ haloalkoxy;
each $R^{1D}$ is independently cyano, $C_1$-$C_6$ alkyl, $C_1$-$C_6$ haloalkyl, $C_1$-$C_6$ alkoxy or $C_2$-$C_6$ alkylcarbonyl;
each $R^{3A}$ is independently $C_1$-$C_4$ alkyl or $C_1$-$C_4$ haloalkyl;
each $R^{3B}$ is independently H, $C_1$-$C_4$ alkyl or $C_1$-$C_4$ haloalkyl;
each $R^{3C}$ is independently H or $C_1$-$C_4$ alkyl;
each $R^{3D}$ is independently H, amino, $C_1$-$C_4$ alkyl or $C_1$-$C_4$ alkylamino;
each $R^{3F}$ is independently hydroxy, halogen, cyano, nitro, $C_1$-$C_6$ alkyl, $C_1$-$C_6$ haloalkyl, $C_1$-$C_6$ alkoxy or $C_1$-$C_6$ haloalkoxy; and
each $R^{3G}$ is independently cyano, $C_1$-$C_6$ alkyl, $C_1$-$C_6$ haloalkyl, $C_1$-$C_6$ alkoxy or $C_2$-$C_6$ alkylcarbonyl.

More particularly, this invention relates to a compound of Formula 1 including all geometric and stereoisomers, an N-oxide or a salt thereof.

This invention also relates to a herbicidal composition comprising a herbicidally effective amount of a compound of the invention and at least one additional component selected from the group consisting of surfactants, solid diluents and liquid diluents.

This invention also relates to a herbicidal composition comprising (a) a compound of the invention and (b) at least one other herbicide (e.g., at least one other herbicide having the same or different site of action).

This invention further relates to a method for controlling the growth of undesired vegetation comprising contacting the vegetation or its environment with a herbicidally effective amount of a compound of the invention (e.g., as a composition described herein).

This invention also includes a herbicidal mixture comprising (a) a compound selected from Formula 1, N-oxides, and salts thereof, and (b) at least one additional active ingredient selected from (b1) through (b16); and salts of compounds of (b1) through (b16), as described below.

DETAILS OF THE INVENTION

As used herein, the terms "comprises," "comprising," "includes," "including," "has," "having," "contains", "containing," "characterized by" or any other variation thereof, are intended to cover a non-exclusive inclusion, subject to any limitation explicitly indicated. For example, a composition, mixture, process, method, article, or apparatus that comprises a list of elements is not necessarily limited to only those elements but may include other elements not expressly listed or inherent to such composition, mixture, process, method, article, or apparatus.

The transitional phrase "consisting of" excludes any element, step, or ingredient not specified. If in the claim, such would close the claim to the inclusion of materials other than those recited except for impurities ordinarily associated therewith. When the phrase "consisting of" appears in a clause of the body of a claim, rather than immediately following the preamble, it limits only the element set forth in that clause; other elements are not excluded from the claim as a whole.

The transitional phrase "consisting essentially of" is used to define a composition, method or apparatus that includes materials, steps, features, components, or elements, in addition to those literally disclosed, provided that these additional materials, steps, features, components, or elements do not materially affect the basic and novel characteristic(s) of the claimed invention. The term "consisting essentially of" occupies a middle ground between "comprising" and "consisting of".

Where applicants have defined an invention or a portion thereof with an open-ended term such as "comprising," it should be readily understood that (unless otherwise stated) the description should be interpreted to also describe such an invention using the terms "consisting essentially of" or "consisting of."

Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, the indefinite articles "a" and "an" preceding an element or component of the invention are intended to be nonrestrictive regarding the number of instances (i.e. occurrences) of the element or component. Therefore "a" or "an" should be read to include one or at least one, and the singular word form of the element or component also includes the plural unless the number is obviously meant to be singular.

As referred to herein, the term "seedling", used either alone or in a combination of words means a young plant developing from the embryo of a seed.

As referred to herein, the term "broadleaf" used either alone or in words such as "broadleaf weed" means dicot or dicotyledon, a term used to describe a group of angiosperms characterized by embryos having two cotyledons.

In the above recitations, the term "alkyl", used either alone or in compound words such as "alkylthio" or "haloalkyl" includes straight-chain or branched alkyl, such as, methyl, ethyl, n-propyl, i-propyl, or the different butyl, pentyl or hexyl isomers. "Alkenyl" includes straight-chain or branched alkenes such as ethenyl, 1-propenyl, 2-propenyl, and the different butenyl, pentenyl and hexenyl isomers. "Alkenyl" also includes polyenes such as 1,2-propadienyl and 2,4-hexadienyl. "Alkynyl" includes straight-chain or branched alkynes such as ethynyl, 1-propynyl, 2-propynyl and the different butynyl, pentynyl and hexynyl isomers. "Alkynyl" can also include moieties comprised of multiple triple bonds such as 2,5-hexadiynyl. "Alkylene" denotes a straight-chain or branched alkanediyl. Examples of "alkylene" include $CH_2$, $CH_2CH_2$, $CH(CH_3)$, $CH_2CH_2CH_2$, $CH_2CH(CH_3)$ and the different butylene isomers. "Alkenylene" denotes a straight-chain or branched alkenediyl containing one olefinic bond. Examples of "alkenylene" include $CH=CH$, $CH_2CH=CH$, $CH=C(CH_3)$ and the different butenylene isomers. "Alkynylene" denotes a straight-chain or branched alkynediyl containing one triple bond. Examples of "alkynylene" include $C≡C$, $CH_2C≡C$, $C≡CCH_2$ and the different butynylene isomers.

"Alkoxy" includes, for example, methoxy, ethoxy, n-propyloxy, isopropyloxy and the different butoxy, pentoxy and hexyloxy isomers. "Alkoxyalkyl" denotes alkoxy substitution on alkyl. Examples of "alkoxyalkyl" include $CH_3OCH_2$, $CH_3OCH_2CH_2$, $CH_3CH_2OCH_2$, $CH_3CH_2CH_2CH_2OCH_2$ and $CH_3CH_2OCH_2CH_2$. "Alkoxyalkoxy" denotes alkoxy substitution on alkoxy. "Alkenyloxy" includes straight-chain or branched alkenyloxy moieties. Examples of "alkenyloxy" include $H_2C=CHCH_2O$, $(CH_3)_2C=CHCH_2O$, $(CH_3)CH=CHCH_2O$, $(CH_3)CH=C(CH_3)CH_2O$ and $CH_2=CHCH_2CH_2O$. "Alkynyloxy" includes straight-chain or branched alkynyloxy moieties. Examples of "alkynyloxy" include $HC≡CCH_2O$, $CH_3C≡CCH_2O$ and $CH_3C≡CCH_2CH_2O$. "Alkylthio" includes branched or straight-chain alkylthio moieties such as methylthio, ethylthio, and the different propylthio, butylthio, pentylthio and hexylthio isomers. "Alkylsulfinyl" includes both enantiomers of an alkylsulfinyl group. Examples of "alkylsulfinyl" include $CH_3S(O)$—, $CH_3CH_2S(O)$—, $CH_3CH_2CH_2S(O)$—, $(CH_3)_2CHS(O)$— and the different butylsulfinyl, pentylsulfinyl and hexylsulfinyl isomers. Examples of "alkylsulfonyl" include $CH_3S(O)_2$—, $CH_3CH_2S(O)_2$—, $CH_3CH_2CH_2S(O)_2$—, $(CH_3)_2CHS(O)_2$—, and the different butylsulfonyl, pentylsulfonyl and hexylsulfonyl isomers. "Alkylthioalkyl" denotes alkylthio substitution on alkyl. Examples of "alkylthioalkyl" include $CH_3SCH_2$, $CH_3SCH_2CH_2$, $CH_3CH_2SCH_2$, $CH_3CH_2CH_2CH_2SCH_2$ and $CH_3CH_2SCH_2CH_2$. "Cyanoalkyl" denotes an alkyl group substituted with one cyano group. Examples of "cyanoalkyl" include $NCCH_2$, NCCH$_2$CH$_2$ and CH$_3$CH(CN)CH$_2$. "Alkylamino", "dialkylamino", and the like, are defined analogously to the above examples.

"Cycloalkyl" includes, for example, cyclopropyl, cyclobutyl, cyclopentyl and cyclohexyl. The term "alkylcycloalkyl" denotes alkyl substitution on a cycloalkyl moiety and includes, for example, ethylcyclopropyl, i-propylcyclobutyl, 3-methylcyclopentyl and 4-methylcyclohexyl. The term "cycloalkylalkyl" denotes cycloalkyl substitution on an alkyl moiety. Examples of "cycloalkylalkyl" include cyclopropylmethyl, cyclopentylethyl, and other cycloalkyl moieties bonded to straight-chain or branched alkyl groups. The term "cycloalkoxy" denotes cycloalkyl linked through an oxygen atom such as cyclopentyloxy and cyclohexyloxy.

The term "halogen", either alone or in compound words such as "haloalkyl", or when used in descriptions such as "alkyl substituted with halogen" includes fluorine, chlorine, bromine or iodine. Further, when used in compound words such as "haloalkyl", or when used in descriptions such as "alkyl substituted with halogen" said alkyl may be partially or fully substituted with halogen atoms which may be the same or different. Examples of "haloalkyl" or "alkyl substituted with halogen" include F$_3$C, ClCH$_2$, CF$_3$CH$_2$ and CF$_3$CCl$_2$. The terms "halocycloalkyl", "haloalkoxy", "haloalkylthio", "haloalkenyl", "haloalkynyl", and the like, are is defined analogously to the term "haloalkyl". Examples of "haloalkoxy" include CF$_3$O—, CCl$_3$CH$_2$O—, HCF$_2$CH$_2$CH$_2$O— and CF$_3$CH$_2$O—. Examples of "haloalkylthio" include CCl$_3$S—, CF$_3$S—, CCl$_3$CH$_2$S— and ClCH$_2$CH$_2$CH$_2$S—. Examples of "haloalkylsulfinyl" include CF$_3$S(O)—, CCl$_3$S(O)—, CF$_3$CH$_2$S(O)— and CF$_3$CF$_2$S(O)—. Examples of "haloalkylsulfonyl" include CF$_3$S(O)$_2$—, CCl$_3$S(O)$_2$—, CF$_3$CH$_2$S(O)$_2$— and CF$_3$CF$_2$S(O)$_2$—. Examples of "haloalkenyl" include (Cl)$_2$C=CHCH$_2$— and CF$_3$CH$_2$CH=CHCH$_2$—. Examples of "haloalkynyl" include HC≡CCHCl—, CF$_3$C≡C—, CCl$_3$C≡C— and FCH$_2$C≡CCH$_2$—. Examples of "haloalkoxyalkoxy" include CF$_3$OCH$_2$O—, ClCH$_2$CH$_2$OCH$_2$CH$_2$O—, Cl$_3$CCH$_2$OCH$_2$O— as well as branched alkyl derivatives.

"Alkylcarbonyl" denotes a straight-chain or branched alkyl moieties bonded to a C(=O) moiety. Examples of "alkylcarbonyl" include CH$_3$C(=O)—, CH$_3$CH$_2$CH$_2$C(=O)— and (CH$_3$)$_2$CHC(=O)—. Examples of "alkoxycarbonyl" include CH$_3$OC(=O)—, CH$_3$CH$_2$OC(=O)—, CH$_3$CH$_2$CH$_2$OC(=O)—, (CH$_3$)$_2$CHOC(=O)— and the different butoxy- or pentoxycarbonyl isomers.

The total number of carbon atoms in a substituent group is indicated by the "$C_i$-$C_j$" prefix where i and j are numbers from 1 to 10. For example, $C_1$-$C_4$ alkylsulfonyl designates methylsulfonyl through butylsulfonyl; $C_2$ alkoxyalkyl designates CH$_3$OCH$_2$—; $C_3$ alkoxyalkyl designates, for example, CH$_3$CH(OCH$_3$)—, CH$_3$OCH$_2$CH$_2$— or CH$_3$CH$_2$OCH$_2$—; and $C_4$ alkoxyalkyl designates the various isomers of an alkyl group substituted with an alkoxy group containing a total of four carbon atoms, examples including CH$_3$CH$_2$CH$_2$OCH$_2$— and CH$_3$CH$_2$OCH$_2$CH$_2$—.

When a compound is substituted with a substituent bearing a subscript that indicates the number of said substituents can exceed 1, said substituents (when they exceed 1) are independently selected from the group of defined substituents, e.g., [(R$^3$)$_m$], m is 0, 1, 2 or 3). Further, when the subscript indicates a range, e.g. (R)$_{i-j}$, then the number of substituents may be selected from the integers between i and j inclusive. When a group contains a substituent which can be hydrogen, for example (R$^1$ or R$^3$), then when this substituent is taken as hydrogen, it is recognized that this is equivalent to said group being unsubstituted. When a variable group is shown to be optionally attached to a position, for example [(R$^3$)$_m$] wherein m may be 0, then hydrogen may be at the position even if not recited in the variable group definition. When one or more positions on a group are said to be "not substituted" or "unsubstituted", then hydrogen atoms are attached to take up any free valency.

Unless otherwise indicated, a "ring" or "ring system" as a component of Formula 1 (e.g., substituent Q) is heterocyclic. The term "ring system" denotes two or more fused rings. The terms "bicyclic ring system" and "fused bicyclic ring system" denote a ring system consisting of two fused rings, in which either ring can be saturated, partially unsaturated, or fully unsaturated unless otherwise indicated. The term "fused heterobicyclic ring system" denotes a fused bicyclic ring system in which at least one ring atom is not carbon. A "bridged bicyclic ring system" is formed by bonding a segment of one or more atoms to nonadjacent ring members of a ring. The term "ring member" refers to an atom or other moiety (e.g., C(=O), C(=S), S(O) or S(O)$_2$) forming the backbone of a ring or ring system.

The terms "carbocyclic ring", "carbocycle" or "carbocyclic ring system" denote a ring or ring system wherein the atoms forming the ring backbone are selected only from carbon. Unless otherwise indicated, a carbocyclic ring can be a saturated, partially unsaturated, or fully unsaturated ring. When a fully unsaturated carbocyclic ring satisfies Hückel's rule, then said ring is also called an "aromatic ring". "Saturated carbocyclic" refers to a ring having a backbone consisting of carbon atoms linked to one another by single bonds; unless otherwise specified, the remaining carbon valences are occupied by hydrogen atoms.

The terms "heterocyclic ring", "heterocycle" or "heterocyclic ring system" denote a ring or ring system in which at least one atom forming the ring backbone is not carbon, e.g., nitrogen, oxygen or sulfur. Typically a heterocyclic ring contains no more than 4 nitrogens, no more than 2 oxygens and no more than 2 sulfurs. Unless otherwise indicated, a heterocyclic ring can be a saturated, partially unsaturated, or fully unsaturated ring. When a fully unsaturated heterocyclic ring satisfies Hückel's rule, then said ring is also called a "heteroaromatic ring" or "aromatic heterocyclic ring". Unless otherwise indicated, heterocyclic rings and ring systems can be attached through any available carbon or nitrogen by replacement of a hydrogen on said carbon or nitrogen.

"Aromatic" indicates that each of the ring atoms is essentially in the same plane and has a p-orbital perpendicular to the ring plane, and that (4n+2) π electrons, where n is a positive integer, are associated with the ring to comply with Hückel's rule. The term "aromatic ring system" denotes a carbocyclic or heterocyclic ring system in which at least one ring of the ring system is aromatic. The term "aromatic carbocyclic ring system" denotes a carbocyclic ring system in which at least one ring of the ring system is aromatic. The term "aromatic heterocyclic ring system" denotes a heterocyclic ring system in which at least one ring of the ring system is aromatic. The term "nonaromatic ring system" denotes a carbocyclic or heterocyclic ring system that may be fully saturated, as well as partially or fully unsaturated, provided that none of the rings in the ring system are aromatic. The term "nonaromatic carbocyclic ring system" in which no ring in the ring system is aromatic. The term "nonaromatic heterocyclic ring system" denotes a heterocyclic ring system in which no ring in the ring system is aromatic.

The term "optionally substituted" in connection with the heterocyclic rings refers to groups which are unsubstituted or have at least one non-hydrogen substituent that does not extinguish the biological activity possessed by the unsubstituted analog. As used herein, the following definitions shall apply unless otherwise indicated. The term "optionally substituted" is used interchangeably with the phrase "substituted or unsubstituted" or with the term "(un)substituted." Unless otherwise indicated, an optionally substituted group may have a substituent at each substitutable position of the group, and each substitution is independent of the other.

When Q is a 5- or 6-membered aromatic heterocyclic ring, it may be attached to the remainder of Formula 1 though any available carbon or nitrogen ring atom, unless otherwise described.

$R^3$ can be (among others) phenyl optionally substituted with one or more substituents selected from a group of substituents as defined in the Summary of the Invention. An example of phenyl optionally substituted with one to five substituents is the ring illustrated as U-1 in Exhibit 1, wherein $R^v$ is $R^{3F}$ as defined in the Summary of the Invention for $R^3$ and r is an integer (from 0 to 5).

As noted above, Q or $R^3$ can be (among others) a 5- or 6-membered aromatic heterocyclic ring, optionally substituted with one or more substituents selected from a group of substituents as defined in the Summary of the Invention. Examples of a 5- or 6-membered aromatic heterocyclic ring optionally substituted with from one or more substituents include the rings U-2 through U-61 illustrated in Exhibit 1 wherein $R^v$ is any substituent as defined in the Summary of the Invention for Q or $R^3$ and r is an integer from 0 to 3, limited by the number of available positions on each U group. As U-29, U-30, U-36, U-37, U-38, U-39, U-40, U-41, U-42 and U-43 have only one available position, for these U groups r is limited to the integers 0 or 1, and r being 0 means that the U group is unsubstituted and a hydrogen is present at the position indicated by $(R^v)_r$.

Exhibit 1

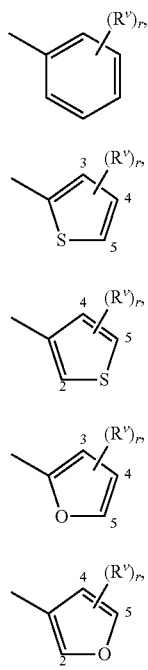

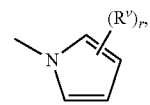
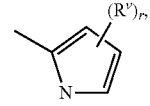
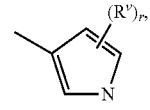
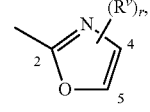
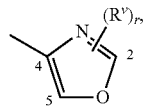
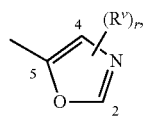
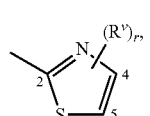
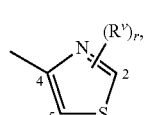
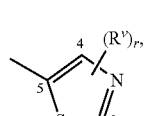
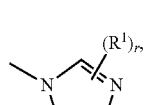
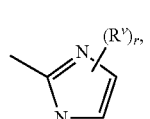
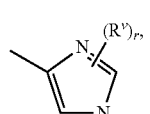
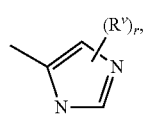

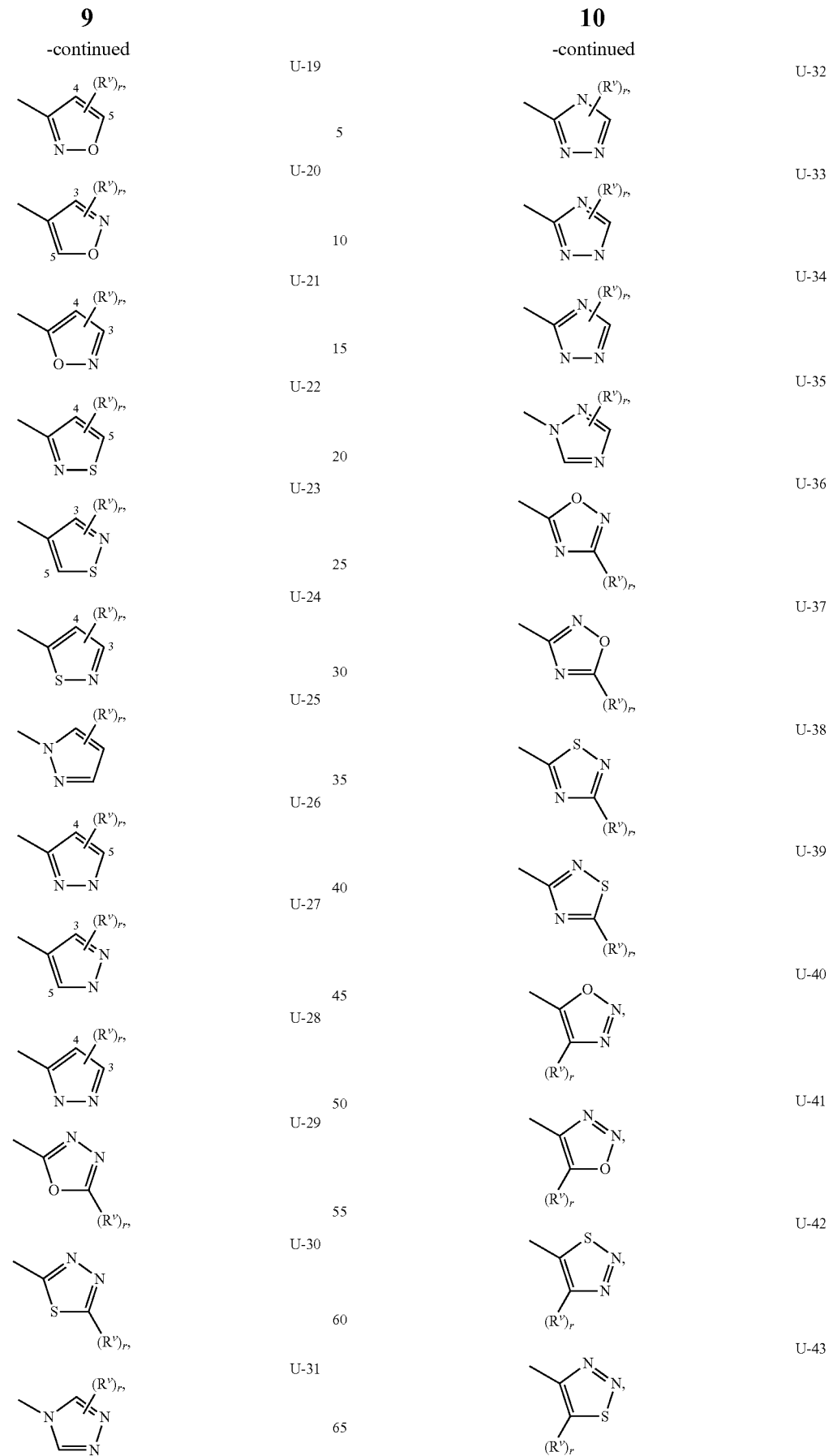

-continued

U-44 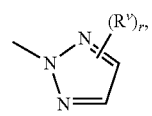

U-45 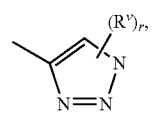

U-46 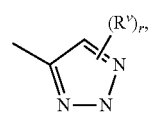

U-47 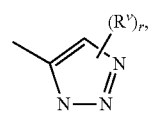

U-48 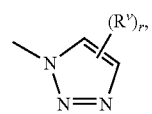

U-49 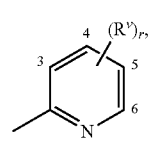

U-50 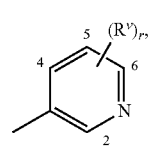

U-51 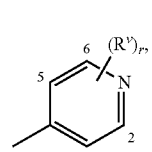

U-52 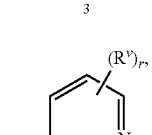

U-53 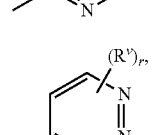

U-54 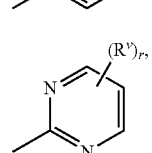

U-55 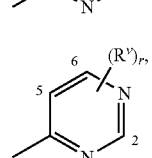

-continued

U-56 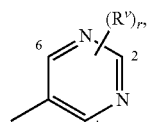

U-57 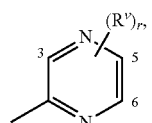

U-58 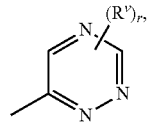

U-59 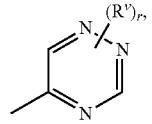

U-60 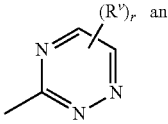

U-61 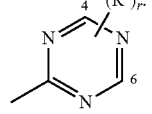

Although $R^v$ groups are shown in the structures U-1 through U-61, it is noted that they do not need to be present since they are optional substituents. Note that when $R^v$ is H when attached to an atom, this is the same as if said atom is unsubstituted. The nitrogen atoms that require substitution to fill their valence are substituted with H or $R^v$. Note that when the attachment point between $(R^v)_r$ and the U group is illustrated as floating, $(R^v)_r$ can be attached to any available carbon atom or nitrogen atom of the U group. Note that when the attachment point on the U group is illustrated as floating, the U group can be attached to the remainder of Formula 1 through any available carbon or nitrogen of the U group by replacement of a hydrogen atom. Note that some U groups can only be substituted with less than 4 $R^v$ groups (e.g., U-2 through U-5, U-7 through U-48, and U-52 through U-61).

A wide variety of synthetic methods are known in the art to enable preparation of aromatic and nonaromatic heterocyclic rings and ring systems; for extensive reviews see the eight volume set of *Comprehensive Heterocyclic Chemistry*, A. R. Katritzky and C. W. Rees editors-in-chief, Pergamon Press, Oxford, 1984 and the twelve volume set of *Comprehensive Heterocyclic Chemistry II*, A. R. Katritzky, C. W. Rees and E. F. V. Scriven editors-in-chief, Pergamon Press, Oxford, 1996.

Compounds of this invention can exist as one or more stereoisomers. The various stereoisomers include enantiomers, diastereomers, atropisomers and geometric isomers. Stereoisomers are isomers of identical constitution but differing in the arrangement of their atoms in space and include enantiomers, diastereomers, cis-trans isomers (also known as geometric isomers) and atropisomers. Atropisomers result from restricted rotation about single bonds where the rotational barrier is high enough to permit isolation of the isomeric species. One skilled in the art will appreciate that one stereoisomer may be more active and/or may exhibit beneficial effects when enriched relative to the other stereoisomer(s) or when separated from the other stereoisomer(s). Additionally, the skilled artisan knows how to separate, enrich, and/or to selectively prepare said stereoisomers. The compounds of the invention may be present as a mixture of stereoisomers, individual stereoisomers or as an optically active form.

Compounds of Formula 1 typically exist in more than one form, and Formula 1 thus include all crystalline and non-crystalline forms of the compounds they represent. Non-crystalline forms include embodiments which are solids such as waxes and gums as well as embodiments which are liquids such as solutions and melts. Crystalline forms include embodiments which represent essentially a single crystal type and embodiments which represent a mixture of polymorphs (i.e. different crystalline types). The term "polymorph" refers to a particular crystalline form of a chemical compound that can crystallize in different crystalline forms, these forms having different arrangements and/or conformations of the molecules in the crystal lattice. Although polymorphs can have the same chemical composition, they can also differ in composition due the presence or absence of co-crystallized water or other molecules, which can be weakly or strongly bound in the lattice. Polymorphs can differ in such chemical, physical and biological properties as crystal shape, density, hardness, color, chemical stability, melting point, hygroscopicity, suspensibility, dissolution rate and biological availability. One skilled in the art will appreciate that a polymorph of a compound of Formula 1 can exhibit beneficial effects (e.g., suitability for preparation of useful formulations, improved biological performance) relative to another polymorph or a mixture of polymorphs of the same compound of Formula 1. Preparation and isolation of a particular polymorph of a compound of Formula 1 can be achieved by methods known to those skilled in the art including, for example, crystallization using selected solvents and temperatures. For a comprehensive discussion of polymorphism see R. Hilfiker, Ed., *Polymorphism in the Pharmaceutical Industry*, Wiley-VCH, Weinheim, 2006.

One skilled in the art will appreciate that not all nitrogen-containing heterocycles can form N-oxides since the nitrogen requires an available lone pair for oxidation to the oxide; one skilled in the art will recognize those nitrogen-containing heterocycles which can form N-oxides. One skilled in the art will also recognize that tertiary amines can form N-oxides. Synthetic methods for the preparation of N-oxides of heterocycles and tertiary amines are very well known by one skilled in the art including the oxidation of heterocycles and tertiary amines with peroxy acids such as peracetic and m-chloroperbenzoic acid (MCPBA), hydrogen peroxide, alkyl hydroperoxides such as t-butyl hydroperoxide, sodium perborate, and dioxiranes such as dimethyldioxirane. These methods for the preparation of N-oxides have been extensively described and reviewed in the literature, see for example: T. L. Gilchrist in *Comprehensive Organic Synthesis*, vol. 7, pp 748-750, S. V. Ley, Ed., Pergamon Press; M. Tisler and B. Stanovnik in *Comprehensive Heterocyclic Chemistry*, vol. 3, pp 18-20, A. J. Boulton and A. McKillop, Eds., Pergamon Press; M. R. Grimmett and B. R. T. Keene in *Advances in Heterocyclic Chemistry*, vol. 43, pp 149-161, A. R. Katritzky, Ed., Academic Press; M. Tisler and B. Stanovnik in *Advances in Heterocyclic Chemistry*, vol. 9, pp 285-291, A. R. Katritzky and A. J. Boulton, Eds., Academic Press; and G. W. H. Cheeseman and E. S. G. Werstiuk in *Advances in Heterocyclic Chemistry*, vol. 22, pp 390-392, A. R. Katritzky and A. J. Boulton, Eds., Academic Press.

One skilled in the art recognizes that because in the environment and under physiological conditions salts of chemical compounds are in equilibrium with their corresponding nonsalt forms, salts share the biological utility of the nonsalt forms. Thus a wide variety of salts of a compound of Formula 1 are useful for control of undesired vegetation (i.e. are agriculturally suitable). The salts of a compound of Formula 1 include acid-addition salts with inorganic or organic acids such as hydrobromic, hydrochloric, nitric, phosphoric, sulfuric, acetic, butyric, fumaric, lactic, maleic, malonic, oxalic, propionic, salicylic, tartaric, 4-toluenesulfonic or valeric acids. When a compound of Formula 1 contains an acidic moiety such as a carboxylic acid or phenol, salts also include those formed with organic or inorganic bases such as pyridine, triethylamine or ammonia, or amides, hydrides, hydroxides or carbonates of sodium, potassium, lithium, calcium, magnesium or barium. Accordingly, the present invention comprises compounds selected from Formula 1, N-oxides and agriculturally suitable salts thereof.

Embodiments of the present invention as described in the Summary of the Invention include (where Formula 1 as used in the following Embodiments includes N-oxides and salts thereof):

Embodiment 1

A compound of Formula 1 wherein Q is selected from

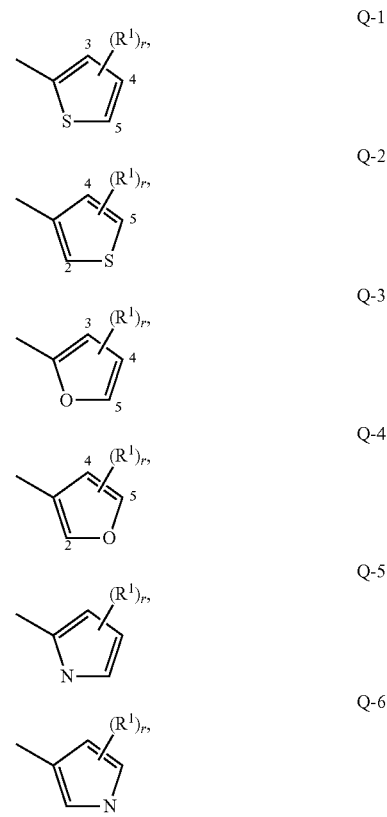

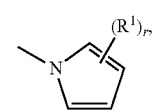  Q-7
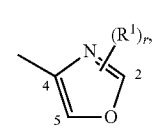  Q-8
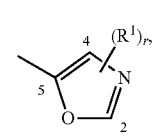  Q-9
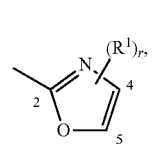  Q-10
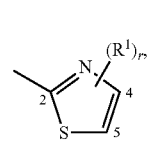  Q-11
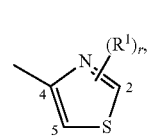  Q-12
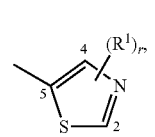  Q-13
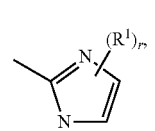  Q-14
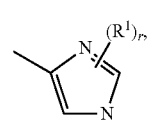  Q-15
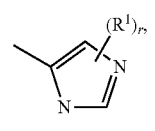  Q-16
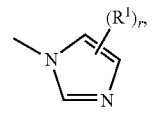  Q-17
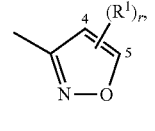  Q-18
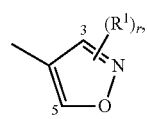  Q-19
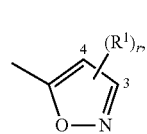  Q-20
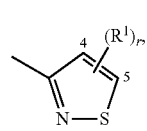  Q-21
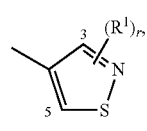  Q-22
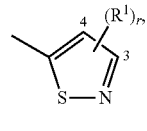  Q-23
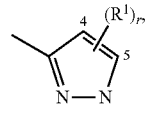  Q-24
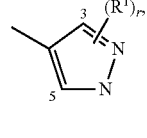  Q-25
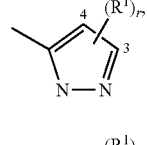  Q-26
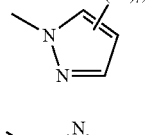  Q-27
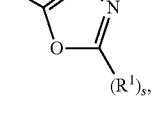  Q-28
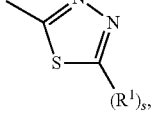  Q-29
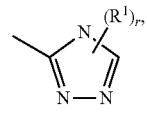  Q-30

| | | |
|---|---|---|
| 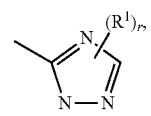 | Q-31 | |
| 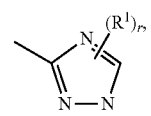 | Q-32 | |
| 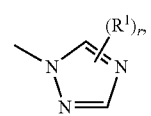 | Q-33 | |
| 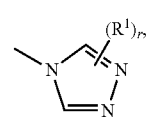 | Q-34 | |
| 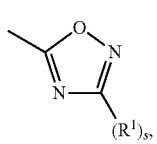 | Q-35 | |
| 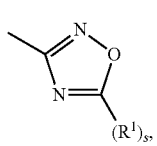 | Q-36 | |
| 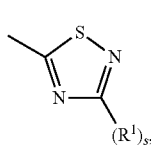 | Q-37 | |
| 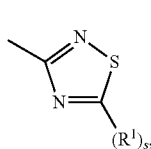 | Q-38 | |
| 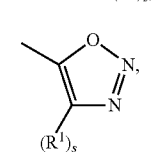 | Q-39 | |
| 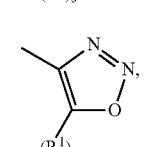 | Q-40 | |
| 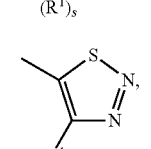 | Q-41 | |
| 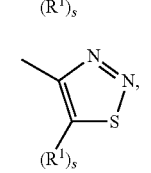 | Q-42 | |
| | | |
|---|---|---|
| 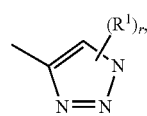 | Q-43 | |
| 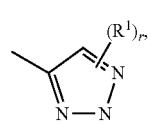 | Q-44 | |
| 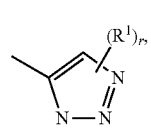 | Q-45 | |
| 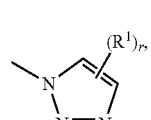 | Q-46 | |
| 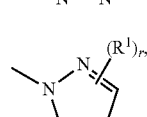 | Q-47 | |
| 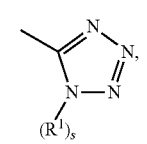 | Q-48 | |
| 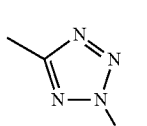 | Q-49 | |
| 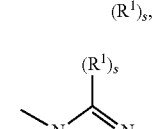 | Q-50 | |
| 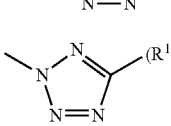 | Q-51 | |
| 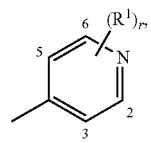 | Q-52 | |
| 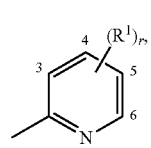 | Q-53 | |
| 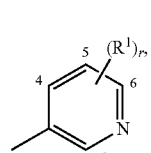 | Q-54 | |

-continued

Q-55 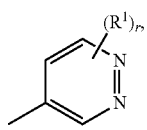

Q-56 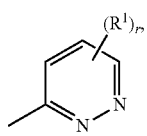

Q-57 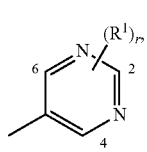

Q-58 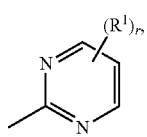

Q-59 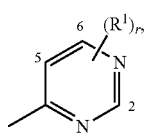

Q-60 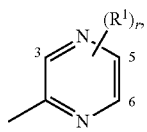

Q-61 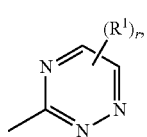

Q-62 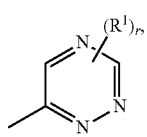

Q-63 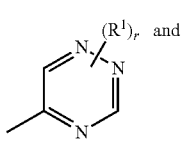

Q-64 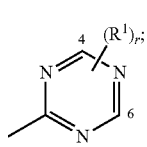

r is 0, 1, 2 or 3; and s is 0 or 1.

Embodiment 2

A compound of Embodiment 1 wherein Q is selected from Q-1 through Q-51.

Embodiment 3

A compound of Embodiment 2 wherein Q is selected from Q-8 through Q-27 and Q-46.

Embodiment 3a

A compound of Embodiment 3 wherein Q is selected from Q-18, Q-20, Q-27 and Q-46.

Embodiment 3b

A compound of Embodiment 2 wherein Q is selected from Q-12 through Q-27.

Embodiment 3c

A compound of Embodiment 2 wherein Q is selected from Q-12 through Q-27 and Q-46.

Embodiment 3d

A compound of Embodiment 1 wherein Q is selected from

Q-18 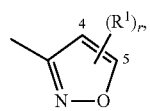

Q-20 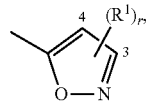

Q-27 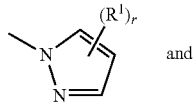 and

Q-52 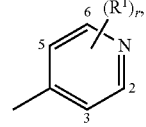

Embodiment 4

A compound of Embodiment 3a wherein Q is selected from

Q-18 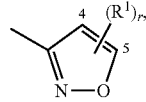

Q-20 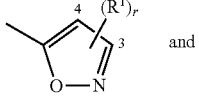 and

-continued

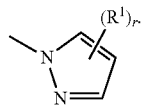

Q-27

Embodiment 5

A compound of Embodiment 4 wherein Q is Q-18.

Embodiment 6

A compound of Embodiment 4 wherein Q is Q-20.

Embodiment 7

A compound of Embodiment 4 wherein Q is Q-27.

Embodiment 7a

A compound of Embodiment 3 wherein Q is selected from Q-18, Q-19 and Q-20.

Embodiment 7b

A compound of Embodiment 1 wherein Q is Q-52.

Embodiment 7c

A compound of Embodiment 1 wherein Q is other than Q-8, Q-9 and Q-10.

Embodiment 8

A compound of Formula 1 or any one of Embodiments 1 through 7 either alone or in combination, wherein Z is O.

Embodiment 9

A compound of Formula 1 or any one of Embodiments 1 through 8 either alone or in combination, wherein each $R^1$ is independently halogen, cyano, $SF_5$, CHO, $C_1$-$C_4$ alkyl, $C_2$-$C_4$ alkenyl, $C_2$-$C_4$ alkynyl, $C_1$-$C_4$ haloalkyl, $C_2$-$C_4$ haloalkenyl, $C_2$-$C_4$ haloalkynyl, $C_2$-$C_6$ alkylcarbonyl, $C_2$-$C_6$ haloalkylcarbonyl, $C_2$-$C_6$ alkoxycarbonyl, $C_1$-$C_4$ alkoxy, $C_3$-$C_4$ alkenyloxy, $C_3$-$C_4$ alkynyloxy, $C_1$-$C_4$ haloalkoxy, $C_3$-$C_4$ haloalkenyloxy, $C_3$-$C_4$ haloalkynyloxy, $C_2$-$C_6$ alkoxyalkyl, $C_2$-$C_6$ haloalkoxyalkyl, $C_2$-$C_6$ cyanoalkyl, $C_1$-$C_4$ hydroxyalkyl, $C_2$-$C_4$ alkylthioalkyl or $SO_nR^{14}$.

Embodiment 10

A compound of Embodiment 9 wherein each $R^1$ is independently halogen, cyano, CHO, $C_1$-$C_4$ alkyl, $C_2$-$C_4$ alkenyl, $C_2$-$C_4$ alkynyl, $C_1$-$C_4$ haloalkyl, $C_2$-$C_4$ haloalkenyl, $C_2$-$C_4$ haloalkynyl, $C_1$-$C_4$ alkoxy, $C_3$-$C_4$ alkenyloxy, $C_3$-$C_4$ alkynyloxy, $C_1$-$C_4$ haloalkoxy, $C_3$-$C_4$ haloalkenyloxy, $C_3$-$C_4$ haloalkynyloxy, $C_2$-$C_6$ alkoxyalkyl, $C_2$-$C_6$ haloalkoxyalkyl, $C_1$-$C_4$ hydroxyalkyl, $C_2$-$C_4$ alkylthioalkyl or $SO_nR^{14}$.

Embodiment 11

A compound of Embodiment 10 wherein each $R^1$ is independently halogen, cyano, $C_1$-$C_4$ alkyl, $C_1$-$C_4$ haloalkyl, $C_1$-$C_4$ alkoxy, $C_1$-$C_4$ haloalkoxy or $SO_nR^{14}$.

Embodiment 12

A compound of Embodiment 11 wherein each $R^1$ is independently halogen, $C_1$-$C_4$ alkyl, $C_1$-$C_4$ haloalkyl or $C_1$-$C_4$ haloalkoxy.

Embodiment 13

A compound of Embodiment 12 wherein each $R^1$ is independently halogen, $C_1$-$C_4$ haloalkyl or $C_1$-$C_4$ haloalkoxy.

Embodiment 14

A compound of Embodiment 13 wherein each $R^1$ is independently halogen or $C_1$-$C_4$ haloalkyl.

Embodiment 15

A compound of Embodiment 14 wherein each $R^1$ is independently F, Cl, Br, $CF_3$, $CHF_2$ or $CH_2F$.

Embodiment 16

A compound of Formula 1 or any one of Embodiments 1 through 15 either alone or in combination, wherein r is 0, 1 or 2.

Embodiment 17

A compound of Embodiment 16 wherein r is 1.

Embodiment 18

A compound of Formula 1 or any one of Embodiments 1 through 15 either alone or in combination, wherein s is 1.

Embodiment 19

A compound of Formula 1 or any one of Embodiments 1 through 18 either alone or in combination, wherein when Q is Q-18 and r is 1 then $R^1$ is attached at the 5 position of the Q-18 ring.

Embodiment 20

A compound of Formula 1 or any one of Embodiments 1 through 18 either alone or in combination, wherein when Q is Q-20 and r is 1 then $R^1$ is attached at the 3 position of the Q-20 ring.

Embodiment 21

A compound of Formula 1 or any one of Embodiments 1 through 18 either alone or in combination, wherein when Q is Q-27 and r is 1 then $R^1$ is attached at the 4 position of the Q-27 ring.

Embodiment 22

A compound of Formula 1 or any one of Embodiments 1 through 21 either alone or in combination, wherein $R^2$ is halogen, $C_1$-$C_4$ alkyl or $C_1$-$C_4$ haloalkyl.

Embodiment 23

A compound of Embodiment 22 wherein $R^2$ is halogen or $C_1$-$C_4$ alkyl.

Embodiment 24

A compound of Embodiment 23 wherein $R^2$ is halogen or $CH_3$.

Embodiment 25

A compound of Embodiment 24 wherein $R^2$ is halogen.

Embodiment 26

A compound of Embodiment 25 wherein $R^2$ is F, Cl or Br.

Embodiment 27

A compound of Formula 1 or any one of Embodiments 1 through 26 either alone or in combination, wherein m is 0, 1 or 2.

Embodiment 28

A compound of Embodiment 27 wherein m is 0 or 1.

Embodiment 29

A compound of Embodiment 28 wherein m is 1.

Embodiment 30

A compound of Embodiment 27 wherein m is 0 (i.e. the 4-, 5- and 6-positions are unsubtituted by $R^3$).

Embodiment 31

A compound of Formula 1 or any one of Embodiments 1 through 30 either alone or in combination, wherein each $R^3$ is independently halogen, cyano, CHO, $C_1$-$C_4$ alkyl, $C_2$-$C_4$ alkenyl, $C_2$-$C_4$ alkynyl, $C_1$-$C_4$ haloalkyl, $C_2$-$C_4$ haloalkenyl, $C_2$-$C_4$ haloalkynyl, $C_3$-$C_6$ cycloalkyl, $C_3$-$C_6$ halocycloalkyl, $C_4$-$C_8$ alkylcycloalkyl, $C_2$-$C_6$ alkylcarbonyl, $C_2$-$C_6$ haloalkylcarbonyl, $C_2$-$C_6$ alkoxycarbonyl, $C_1$-$C_4$ alkoxy, $C_3$-$C_4$ alkenyloxy, $C_3$-$C_4$ alkynyloxy, $C_1$-$C_4$ haloalkoxy, $C_3$-$C_4$ haloalkenyloxy, $C_3$-$C_4$ haloalkynyloxy, $C_3$-$C_6$ cycloalkoxy, $C_3$-$C_6$ halocycloalkoxy, $C_2$-$C_6$ alkoxyalkyl, $C_2$-$C_6$ haloalkoxyalkyl, $C_2$-$C_4$ alkylcarbonyloxy, $C_2$-$C_6$ cyanoalkyl, $C(=O)N(R^{3A})(R^{3B})$, $C(=NOR^{3C})H$ or $SO_nR^{3E}$; or a phenyl ring optionally substituted with up to 5 substituents independently selected from $R^{3F}$; or a 5- or 6-membered heteroaromatic ring containing ring members selected from carbon atoms and up to 4 heteroatoms independently selected from up to 2 O, up to 2 S and up to 4 N atoms, each ring optionally substituted with up to 3 substituents independently selected from $R^{3F}$ on carbon atom ring members and $R^{3G}$ on nitrogen atom ring members.

Embodiment 32

A compound of Embodiment 31 wherein each $R^3$ is independently halogen, cyano, CHO, $C_1$-$C_4$ alkyl, $C_2$-$C_4$ alkenyl, $C_2$-$C_4$ alkynyl, $C_1$-$C_4$ haloalkyl, $C_2$-$C_4$ haloalkenyl, $C_2$-$C_4$ haloalkynyl, $C_3$-$C_6$ cycloalkyl, $C_3$-$C_6$ halocycloalkyl, $C_2$-$C_6$ alkylcarbonyl, $C_2$-$C_6$ haloalkylcarbonyl, $C_2$-$C_6$ alkoxycarbonyl, $C_1$-$C_4$ alkoxy, $C_1$-$C_4$ haloalkoxy, $C_2$-$C_6$ alkoxyalkyl, $C_2$-$C_6$ haloalkoxyalkyl, $C_2$-$C_6$ cyanoalkyl or $SO_nR^{3E}$; or a 5- or 6-membered heteroaromatic ring containing ring members selected from carbon atoms and up to 4 heteroatoms independently selected from up to 2 O, up to 2 S and up to 4 N atoms, each ring optionally substituted with up to 3 substituents independently selected from $R^{3F}$ on carbon atom ring members and $R^{3G}$ on nitrogen atom ring members.

Embodiment 33

A compound of Embodiment 32 wherein each $R^3$ is independently halogen, cyano, $C_1$-$C_4$ alkyl, $C_2$-$C_4$ alkenyl, $C_2$-$C_4$ alkynyl, $C_1$-$C_4$ haloalkyl, $C_2$-$C_6$ alkylcarbonyl, $C_2$-$C_6$ haloalkylcarbonyl, $C_2$-$C_6$ alkoxycarbonyl, $C_1$-$C_4$ alkoxy, $C_1$-$C_4$ haloalkoxy, $C_2$-$C_6$ alkoxyalkyl or $C_2$-$C_6$ haloalkoxyalkyl.

Embodiment 34

A compound of Embodiment 33 wherein each $R^3$ is independently halogen, cyano, $C_1$-$C_4$ alkyl or $C_1$-$C_4$ haloalkyl.

Embodiment 35

A compound of Embodiment 34 wherein each $R^3$ is independently halogen or cyano.

Embodiment 36

A compound of Embodiment 35 wherein each $R^3$ is independently halogen.

Embodiment 37

A compound of Formula 1 or any one of Embodiments 1 through 36 either alone or in combination, wherein each $R^{1A}$ is independently $C_1$-$C_4$ alkyl or $C_1$-$C_4$ haloalkyl.

Embodiment 38

A compound of Embodiment 37 wherein each $R^{1A}$ is independently $C_1$-$C_4$ haloalkyl.

Embodiment 39

A compound of Formula 1 or any one of Embodiments 1 through 38 either alone or in combination, wherein each $R^{3E}$ is independently $C_1$-$C_4$ alkyl.

Embodiment 39a

A compound of Formula 1 or any one of Embodiments 1 through 39 either alone or in combination, wherein each $R^{3E}$ is $CH_3$.

Embodiment 40

A compound of Formula 1 or any one of Embodiments 1 through 39 either alone or in combination, wherein each $R^{3A}$ is independently $C_1$-$C_4$ alkyl.

Embodiment 41

A compound of Formula 1 or any one of Embodiments 1 through 40 either alone or in combination, wherein each $R^{3B}$ is independently H or $C_1$-$C_4$ alkyl.

Embodiment 42

A compound of Formula 1 or any one of Embodiments 1 through 41 either alone or in combination, wherein each $R^{3C}$ is independently H or $C_1$-$C_4$ alkyl.

Embodiment 43

A compound of Formula 1 or any one of Embodiments 1 through 42 either alone or in combination, wherein each $R^{3D}$ is independently H or $C_1$-$C_4$ alkyl.

Embodiment 44

A compound of Formula 1 or any one of Embodiments 1 through 43 either alone or in combination, wherein each n is independently 0 or 2.

Embodiment 45

A compound of Embodiment 44 wherein n is 2.

Embodiment 46

A compound of Embodiment 44 wherein n is 0.

Embodiments of this invention, including Embodiments 1-46 above as well as any other embodiments described herein, can be combined in any manner, and the descriptions of variables in the embodiments pertain not only to the compounds of Formula 1 but also to the starting compounds and intermediate compounds useful for preparing the compounds of Formula 1. In addition, embodiments of this invention, including Embodiments 1-46 above as well as any other embodiments described herein, and any combination thereof, pertain to the compositions and methods of the present invention.

Combinations of Embodiments 1-46 are illustrated by:

Embodiment A

A compound of Formula 1 wherein
Q is selected from Q-1 through Q-64;
r is 0, 1, 2 or 3;
s is 0 or 1;
each $R^1$ is independently halogen, cyano, $SF_5$, CHO, $C_1$-$C_4$ alkyl, $C_2$-$C_4$ alkenyl, $C_2$-$C_4$ alkynyl, $C_1$-$C_4$ haloalkyl, $C_2$-$C_4$ haloalkenyl, $C_2$-$C_4$ haloalkynyl, $C_2$-$C_6$ alkylcarbonyl, $C_2$-$C_6$ haloalkylcarbonyl, $C_2$-$C_6$ alkoxycarbonyl, $C_1$-$C_4$ alkoxy, $C_3$-$C_4$ alkenyloxy, $C_3$-$C_4$ alkynyloxy, $C_1$-$C_4$ haloalkoxy, $C_3$-$C_4$ haloalkenyloxy, $C_3$-$C_4$ haloalkynyloxy, $C_2$-$C_6$ alkoxyalkyl, $C_2$-$C_6$ haloalkoxyalkyl, $C_2$-$C_6$ cyanoalkyl, $C_1$-$C_4$ hydroxyalkyl, $C_2$-$C_4$ alkylthioalkyl or $SO_nR^{14}$;
$R^3$ is independently halogen, cyano, CHO, $C_1$-$C_4$ alkyl, $C_2$-$C_4$ alkenyl, $C_2$-$C_4$ alkynyl, $C_1$-$C_4$ haloalkyl, $C_2$-$C_4$ haloalkenyl, $C_2$-$C_4$ haloalkynyl, $C_3$-$C_6$ cycloalkyl, $C_3$-$C_6$ halocycloalkyl, $C_4$-$C_8$ alkylcycloalkyl, $C_2$-$C_6$ alkylcarbonyl, $C_2$-$C_6$ haloalkylcarbonyl, $C_2$-$C_6$ alkoxycarbonyl, $C_1$-$C_4$ alkoxy, $C_3$-$C_4$ alkenyloxy, $C_3$-$C_4$ alkynyloxy, $C_1$-$C_4$ haloalkoxy, $C_3$-$C_4$ haloalkenyloxy, $C_3$-$C_4$ haloalkynyloxy, $C_3$-$C_6$ cycloalkoxy, $C_3$-$C_6$ halocycloalkoxy, $C_2$-$C_6$ alkoxyalkyl, $C_2$-$C_6$ haloalkoxyalkyl, $C_2$-$C_4$ alkylcarbonyloxy, $C_2$-$C_6$ cyanoalkyl, $C(=O)N(R^{3A})(R^{3B})$, $C(=NOR^{3C})H$ or $SO_nR^{3E}$; or a phenyl ring optionally substituted with up to 5 substituents independently selected from $R^{3F}$; or a 5- or 6-membered heteroaromatic ring containing ring members selected from carbon atoms and up to 4 heteroatoms independently selected from up to 2 O, up to 2 S and up to 4 N atoms, each ring optionally substituted with up to 3 substituents independently selected from $R^{3F}$ on carbon atom ring members and $R^{3G}$ on nitrogen atom ring members;
Z is O; and
m is 0, 1 or 2.

Embodiment B

A compound of Embodiment A wherein
each $R^1$ is independently halogen, cyano, CHO, $C_1$-$C_4$ alkyl, $C_2$-$C_4$ alkenyl, $C_2$-$C_4$ alkynyl, $C_1$-$C_4$ haloalkyl, $C_2$-$C_4$ haloalkenyl, $C_2$-$C_4$ haloalkynyl, $C_1$-$C_4$ alkoxy, $C_3$-$C_4$ alkenyloxy, $C_3$-$C_4$ alkynyloxy, $C_1$-$C_4$ haloalkoxy, $C_3$-$C_4$ haloalkenyloxy, $C_3$-$C_4$ haloalkynyloxy, $C_2$-$C_6$ alkoxyalkyl, $C_2$-$C_6$ haloalkoxyalkyl, $C_1$-$C_4$ hydroxyalkyl, $C_2$-$C_4$ alkylthioalkyl or $SO_nR^{14}$;
$R^2$ is halogen, $C_1$-$C_4$ alkyl or $C_1$-$C_4$ haloalkyl;
each $R^3$ is independently halogen, cyano, CHO, $C_1$-$C_4$ alkyl, $C_2$-$C_4$ alkenyl, $C_2$-$C_4$ alkynyl, $C_1$-$C_4$ haloalkyl, $C_2$-$C_4$ haloalkenyl, $C_2$-$C_4$ haloalkynyl, $C_3$-$C_6$ cycloalkyl, $C_3$-$C_6$ halocycloalkyl, $C_2$-$C_6$ alkylcarbonyl, $C_2$-$C_6$ haloalkylcarbonyl, $C_2$-$C_6$ alkoxycarbonyl, $C_1$-$C_4$ alkoxy, $C_1$-$C_4$ haloalkoxy, $C_2$-$C_6$ alkoxyalkyl, $C_2$-$C_6$ haloalkoxyalkyl, $C_2$-$C_6$ cyanoalkyl or $SO_nR^{3E}$; or a 5- or 6-membered heteroaromatic ring containing ring members selected from carbon atoms and up to 4 heteroatoms independently selected from up to 2 O, up to 2 S and up to 4 N atoms, each ring optionally substituted with up to 3 substituents independently selected from $R^{3F}$ on carbon atom ring members and $R^{3G}$ on nitrogen atom ring members; and
m is 0 or 1.

Embodiment B1

A compound of Embodiment A wherein
Q is selected from Q-12 through Q-27;
each $R^1$ is independently halogen, cyano, CHO, $C_1$-$C_4$ alkyl, $C_2$-$C_4$ alkenyl, $C_2$-$C_4$ alkynyl, $C_1$-$C_4$ haloalkyl, $C_2$-$C_4$ haloalkenyl, $C_2$-$C_4$ haloalkynyl, $C_1$-$C_4$ alkoxy, $C_3$-$C_4$ alkenyloxy, $C_3$-$C_4$ alkynyloxy, $C_1$-$C_4$ haloalkoxy, $C_3$-$C_4$ haloalkenyloxy, $C_3$-$C_4$ haloalkynyloxy, $C_2$-$C_6$ alkoxyalkyl, $C_2$-$C_6$ haloalkoxyalkyl, $C_1$-$C_4$ hydroxyalkyl, $C_2$-$C_4$ alkylthioalkyl or $SO_nR^{14}$;
$R^2$ is halogen, $C_1$-$C_4$ alkyl or $C_1$-$C_4$ haloalkyl;
each $R^3$ is independently halogen, cyano, CHO, $C_1$-$C_4$ alkyl, $C_2$-$C_4$ alkenyl, $C_2$-$C_4$ alkynyl, $C_1$-$C_4$ haloalkyl, $C_2$-$C_4$ haloalkenyl, $C_2$-$C_4$ haloalkynyl, $C_3$-$C_6$ cycloalkyl, $C_3$-$C_6$ halocycloalkyl, $C_2$-$C_6$ alkylcarbonyl, $C_2$-$C_6$ haloalkylcarbonyl, $C_2$-$C_6$ alkoxycarbonyl, $C_1$-$C_4$ alkoxy, $C_1$-$C_4$ haloalkoxy, $C_2$-$C_6$ alkoxyalkyl, $C_2$-$C_6$ haloalkoxyalkyl, $C_2$-$C_6$ cyanoalkyl or $SO_nR^{3E}$; or a 5- or 6-membered heteroaromatic ring containing ring members selected from carbon atoms and up to 4 heteroatoms independently selected from up to 2 O, up to 2 S and up to 4 N atoms, each ring optionally substituted with up to 3 substituents independently selected from $R^{3F}$ on carbon atom ring members and $R^{3G}$ on nitrogen atom ring members; and m is 0 or 1.

Embodiment C

A compound of Embodiment B wherein
Q is selected from Q-8 through Q-27 and Q-46;
each $R^1$ is independently halogen, cyano, $C_1$-$C_4$ alkyl, $C_1$-$C_4$ haloalkyl, $C_1$-$C_4$ alkoxy, $C_1$-$C_4$ haloalkoxy or $SO_nR^{14}$;
$R^2$ is halogen or $C_1$-$C_4$ alkyl;
each $R^3$ is independently halogen, cyano, $C_1$-$C_4$ alkyl, $C_2$-$C_4$ alkenyl, $C_2$-$C_4$ alkynyl, $C_1$-$C_4$ haloalkyl, $C_2$-$C_6$ alkylcarbonyl, $C_2$-$C_6$ haloalkylcarbonyl, $C_2$-$C_6$ alkoxycarbonyl, $C_1$-$C_4$ alkoxy, $C_1$-$C_4$ haloalkoxy, $C_2$-$C_6$ alkoxyalkyl or $C_2$-$C_6$ haloalkoxyalkyl; and
each $R^{14}$ is independently $C_1$-$C_4$ alkyl or $C_1$-$C_4$ haloalkyl.

Embodiment C1

A compound of Embodiment B wherein
Q is selected from

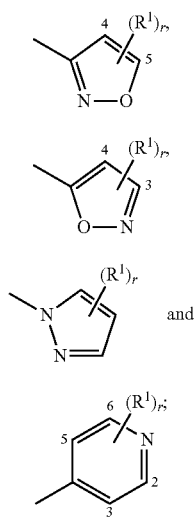

r is 1;
$R^1$ is independently halogen, cyano, $C_1$-$C_4$ alkyl, $C_1$-$C_4$ haloalkyl, $C_1$-$C_4$ alkoxy, $C_1$-$C_4$ haloalkoxy or $SO_nR^{14}$;
$R^2$ is halogen or $C_1$-$C_4$ alkyl;
each $R^3$ is independently halogen, cyano, $C_1$-$C_4$ alkyl, $C_2$-$C_4$ alkenyl, $C_2$-$C_4$ alkynyl, $C_1$-$C_4$ haloalkyl, $C_2$-$C_6$ alkylcarbonyl, $C_2$-$C_6$ haloalkylcarbonyl, $C_2$-$C_6$ alkoxycarbonyl, $C_1$-$C_4$ alkoxy, $C_1$-$C_4$ haloalkoxy, $C_2$-$C_6$ alkoxyalkyl or $C_2$-$C_6$ haloalkoxyalkyl;
each $R^{14}$ is independently $C_1$-$C_4$ alkyl or $C_1$-$C_4$ haloalkyl; and
m is 0 or 1.

Embodiment D

A compound of Embodiment C wherein
Q is selected from Q-18, Q-20 and Q-27;
each $R^1$ is independently halogen, $C_1$-$C_4$ alkyl, $C_1$-$C_4$ haloalkyl or $C_1$-$C_4$ haloalkoxy;
$R^2$ is halogen or $CH_3$; and
each $R^3$ is independently halogen, cyano, $C_1$-$C_4$ alkyl or $C_1$-$C_4$ haloalkyl.

Specific embodiments include compounds of Formula 1 selected from the group consisting of:
2-[[2-(4-bromo-1H-pyrazol-1-yl)-3-pyridinyl]oxy]-5-chloropyrimidine (Compound 1),
5-chloro-2-[[2-(4-chloro-1H-pyrazol-1-yl)-3-pyridinyl]oxy]pyrimidine (Compound 2),
5-chloro-2-[[2-[3-(difluoromethyl)-5-isoxazolyl]-3-pyridinyl]oxy]pyrimidine (Compound 5) and
5-chloro-2-[[2-[5-(difluoromethyl)-3-isoxazolyl]-3-pyridinyl]oxy]pyrimidine (Compound 6).

This invention also relates to a method for controlling undesired vegetation comprising applying to the locus of the vegetation herbicidally effective amounts of the compounds of the invention (e.g., as a composition described herein). Of note as embodiments relating to methods of use are those involving the compounds of embodiments described above. Compounds of the invention are particularly useful for selective control of weeds in crops such as wheat, barley, maize, soybean, sunflower, cotton, oilseed rape and rice, and specialty crops such as sugarcane, citrus, fruit and nut crops.

Also noteworthy as embodiments are herbicidal compositions of the present invention comprising the compounds of embodiments described above.

This invention also includes a herbicidal mixture comprising (a) a compound selected from Formula 1, N-oxides, and salts thereof, and (b) at least one additional active ingredient selected from (b1) photosystem II inhibitors, (b2) acetohydroxy acid synthase (AHAS) inhibitors, (b3) acetyl-CoA carboxylase (ACCase) inhibitors, (b4) auxin mimics, (b5) 5-enol-pyruvylshikimate-3-phosphate (EPSP) synthase inhibitors, (b6) photosystem I electron diverters, (b7) protoporphyrinogen oxidase (PPO) inhibitors, (b8) glutamine synthetase (GS) inhibitors, (b9) very long chain fatty acid (VLCFA) elongase inhibitors, (b10) auxin transport inhibitors, (b11) phytoene desaturase (PDS) inhibitors, (b12) 4-hydroxyphenyl-pyruvate dioxygenase (HPPD) inhibitors, (b13) homogentisate solenesyltransererase (HST) inhibitors, (b14) cellulose biosynthesis inhibitors, (b15) other herbicides including mitotic disruptors, organic arsenicals, asulam, bromobutide, cinmethylin, cumyluron, dazomet, difenzoquat, dymron, etobenzanid, flurenol, fosamine, fosamine-ammonium, hydantocidin, metam, methyldymron, oleic acid, oxaziclomefone, pelargonic acid and pyributicarb, and (b16) herbicide safeners; and salts of compounds of (b1) through (b16).

"Photosystem II inhibitors" (b1) are chemical compounds that bind to the D-1 protein at the $Q_B$-binding niche and thus block electron transport from $Q_A$ to $Q_B$ in the chloroplast thylakoid membranes. The electrons blocked from passing through photosystem II are transferred through a series of reactions to form toxic compounds that disrupt cell membranes and cause chloroplast swelling, membrane leakage, and ultimately cellular destruction. The $Q_B$-binding niche has three different binding sites: binding site A binds the triazines such as atrazine, triazinones such as hexazinone, and uracils such as bromacil, binding site B binds the phenylureas such as diuron, and binding site C binds benzothiadiazoles such as bentazon, nitriles such as bromoxynil and phenyl-pyridazines such as pyridate. Examples of photosystem II inhibitors include ametryn, amicarbazone, atrazine, bentazon, bromacil, bromofenoxim, bromoxynil, chlorbromuron, chloridazon, chlorotoluron, chloroxuron, cumyluron, cyanazine, daimuron, desmedipham, desmetryn, dimefuron, dimethametryn, diuron, ethidimuron, fenuron, fluometuron, hexazinone, ioxynil, isoproturon, isouron, lenacil, linuron, metamitron, methabenzthiazuron, metobromuron, metoxuron, metribuzin, monolinuron, neburon, pentanochlor, phenmedipham, prometon, prometryn, propanil, propazine, pyridafol, pyridate, siduron, simazine, simetryn, tebuthiuron, terbacil, terbumeton, terbuthylazine, terbutryn and trietazine.

"AHAS inhibitors" (b2) are chemical compounds that inhibit acetohydroxy acid synthase (AHAS), also known as acetolactate synthase (ALS), and thus kill plants by inhibiting the production of the branched-chain aliphatic amino acids such as valine, leucine and isoleucine, which are required for protein synthesis and cell growth. Examples of AHAS inhibitors include amidosulfuron, azimsulfuron, bensulfuron-methyl, bispyribac-sodium, cloransulam-methyl, chlorimuron-ethyl, chlorsulfuron, cinosulfuron, cyclosulfamuron, diclosulam, ethametsulfuron-methyl, ethoxysulfuron, flazasulfuron, florasulam, flucarbazone-sodium, flumetsulam, flupyrsulfuron-methyl, flupyrsulfuron-sodium, foramsulfuron, halosulfuron-methyl, imazamethabenz-methyl, imazamox, imazapic, imazapyr, imazaquin, imazethapyr, imazosulfuron, iodosulfuron-methyl (including sodium salt), iofensulfuron (2-iodo-N-[[(4-methoxy-6-methyl-1,3,5-triazin-2-yl)amino]carbonyl]benzenesulfonamide), mesosulfuron-methyl, metazosulfuron (3-chloro-4-(5,6-dihydro-5-methyl-1,4,2-dioxazin-3-yl)-N-[[(4,6-dimethoxy-2-pyrimidinyl)amino]carbonyl]-1-methyl-1H-pyrazole-5-sulfonamide), metosulam, metsulfuron-methyl, nicosulfuron, oxasulfuron, penoxsulam, primisulfuron-methyl, propoxycarbazone-sodium, propyrisulfuron (2-chloro-N-[[(4,6-dimethoxy-2-pyrimidinyl)amino]carbonyl]-6-propylimidazo[1,2-b]pyridazine-3-sulfonamide), prosulfuron, pyrazosulfuron-ethyl, pyribenzoxim, pyriftalid, pyriminobac-methyl, pyrithiobac-sodium, rimsulfuron, sulfometuron-methyl, sulfosulfuron, thiencarbazone, thifensulfuron-methyl, triafamone (N-[2-[(4,6-dimethoxy-1,3,5-triazin-2-yl)carbonyl]-6-fluorophenyl]-1,1-difluoro-N-methylmethanesulfonamide), triasulfuron, tribenuron-methyl, trifloxysulfuron (including sodium salt), triflusulfuron-methyl and tritosulfuron.

"ACCase inhibitors" (b3) are chemical compounds that inhibit the acetyl-CoA carboxylase enzyme, which is responsible for catalyzing an early step in lipid and fatty acid synthesis in plants. Lipids are essential components of cell membranes, and without them, new cells cannot be produced. The inhibition of acetyl CoA carboxylase and the subsequent lack of lipid production leads to losses in cell membrane integrity, especially in regions of active growth such as meristems. Eventually shoot and rhizome growth ceases, and shoot meristems and rhizome buds begin to die back. Examples of ACCase inhibitors include alloxydim, butroxydim, clethodim, clodinafop, cycloxydim, cyhalofop, diclofop, fenoxaprop, fluazifop, haloxyfop, pinoxaden, profoxydim, propaquizafop, quizalofop, sethoxydim, tepraloxydim and tralkoxydim, including resolved forms such as fenoxaprop-P, fluazifop-P, haloxyfop-P and quizalofop-P and ester forms such as clodinafop-propargyl, cyhalofop-butyl, diclofop-methyl and fenoxaprop-P-ethyl.

Auxin is a plant hormone that regulates growth in many plant tissues. "Auxin mimics" (b4) are chemical compounds mimicking the plant growth hormone auxin, thus causing uncontrolled and disorganized growth leading to plant death in susceptible species. Examples of auxin mimics include aminocyclopyrachlor (6-amino-5-chloro-2-cyclopropyl-4-pyrimidinecarboxylic acid) and its methyl and ethyl esters and its sodium and potassium salts, aminopyralid, benazolin-ethyl, chloramben, clacyfos, clomeprop, clopyralid, dicamba, 2,4-D, 2,4-DB, dichlorprop, fluroxypyr, halauxifen (4-amino-3-chloro-6-(4-chloro-2-fluoro-3-methoxyphenyl)-2-pyridinecarboxylic acid), halauxifen-methyl (methyl 4-amino-3-chloro-6-(4-chloro-2-fluoro-3-methoxyphenyl)-2-pyridinecarboxylate), MCPA, MCPB, mecoprop, picloram, quinclorac, quinmerac, 2,3,6-TBA, triclopyr, and methyl 4-amino-3-chloro-6-(4-chloro-2-fluoro-3-methoxyphenyl)-5-fluoro-2-pyridinecarboxylate.

"EPSP synthase inhibitors" (b5) are chemical compounds that inhibit the enzyme, 5-enol-pyruvylshikimate-3-phosphate synthase, which is involved in the synthesis of aromatic amino acids such as tyrosine, tryptophan and phenylalanine. EPSP inhibitor herbicides are readily absorbed through plant foliage and translocated in the phloem to the growing points. Glyphosate is a relatively nonselective postemergence herbicide that belongs to this group. Glyphosate includes esters and salts such as ammonium, isopropylammonium, potassium, sodium (including sesquisodium) and trimesium (alternatively named sulfosate).

"Photosystem I electron diverters" (b6) are chemical compounds that accept electrons from Photosystem I, and after several cycles, generate hydroxyl radicals. These radicals are extremely reactive and readily destroy unsaturated lipids, including membrane fatty acids and chlorophyll. This destroys cell membrane integrity, so that cells and organelles "leak", leading to rapid leaf wilting and desiccation, and eventually to plant death. Examples of this second type of photosynthesis inhibitor include diquat and paraquat.

"PPO inhibitors" (b7) are chemical compounds that inhibit the enzyme protoporphyrinogen oxidase, quickly resulting in formation of highly reactive compounds in plants that rupture cell membranes, causing cell fluids to leak out. Examples of PPO inhibitors include acifluorfen-sodium, azafenidin, benzfendizone, bifenox, butafenacil, carfentrazone, carfentrazone-ethyl, chlomethoxyfen, cinidon-ethyl, fluazolate, flufenpyr-ethyl, flumiclorac-pentyl, flumioxazin, fluoroglycofen-ethyl, fluthiacet-methyl, fomesafen, halosafen, lactofen, oxadiargyl, oxadiazon, oxyfluorfen, pentoxazone, profluazol, pyraclonil, pyraflufen-ethyl, saflufenacil, sulfentrazone, thidiazimin, trifludimoxazin (dihydro-1,5-dimehyl-6-thioxo-3-[2,2,7-trifluoro-3,4-dihydro-3-oxo-4-(2-propyn-1-yl)-2H-1,4-benzoxazin-6-yl]-1,3,5-triazine-2,4(1H,3H)-dione) and tiafenacil (methyl N-[2-[[2-chloro-5-[3,6-dihydro-3-methyl-2,6-dioxo-4-(trifluoromethyl)-1(2H)-pyrimidinyl]-4-fluorophenyl]thio]-1-oxopropyl]-β-alaninate).

"GS inhibitors" (b8) are chemical compounds that inhibit the activity of the glutamine synthetase enzyme, which plants use to convert ammonia into glutamine. Consequently, ammonia accumulates and glutamine levels decrease. Plant damage probably occurs due to the combined effects of ammonia toxicity and deficiency of amino acids required for other metabolic processes. The GS inhibitors include glufosinate and its esters and salts such as glufosinate-ammonium and other phosphinothricin derivatives, glufosinate-P ((2S)-2-amino-4-(hydroxymethylphosphinyl)butanoic acid) and bilanaphos.

"VLCFA elongase inhibitors" (b9) are herbicides having a wide variety of chemical structures, which inhibit the elongase. Elongase is one of the enzymes located in or near chloroplasts which are involved in biosynthesis of VLCFAs.

In plants, very-long-chain fatty acids are the main constituents of hydrophobic polymers that prevent desiccation at the leaf surface and provide stability to pollen grains. Such herbicides include acetochlor, alachlor, anilofos, butachlor, cafenstrole, dimethachlor, dimethenamid, diphenamid, fenoxasulfone (3-[[(2,5-dichloro-4-ethoxyphenyl)methyl]sulfonyl]-4,5-dihydro-5,5-dimethylisoxazole), fentrazamide, flufenacet, indanofan, mefenacet, metazachlor, metolachlor, naproanilide, napropamide, napropamide-M ((2R)—N,N-diethyl-2-(1-naphthalenyloxy)propanamide), pethoxamid, piperophos, pretilachlor, propachlor, propisochlor, pyroxasulfone, and thenylchlor, including resolved forms such as S-metolachlor and chloroacetamides and oxyacetamides.

"Auxin transport inhibitors" (b10) are chemical substances that inhibit auxin transport in plants, such as by binding with an auxin-carrier protein. Examples of auxin transport inhibitors include diflufenzopyr, naptalam (also known as N-(1-naphthyl)phthalamic acid and 2-[(1-naphthalenylamino)carbonyl]benzoic acid).

"PDS inhibitors" (b11) are chemical compounds that inhibit carotenoid biosynthesis pathway at the phytoene desaturase step. Examples of PDS inhibitors include beflubutamid, diflufenican, fluridone, flurochloridone, flurtamone norflurzon and picolinafen.

"HPPD inhibitors" (b12) are chemical substances that inhibit the biosynthesis of synthesis of 4-hydroxyphenylpyruvate dioxygenase. Examples of HPPD inhibitors include benzobicyclon, benzofenap, bicyclopyrone (4-hydroxy-3-[[2-[(2-methoxyethoxy)methyl]-6-(trifluoromethyl)-3-pyridinyl]carbonyl]bicyclo[3.2.1]oct-3-en-2-one), fenquinotrione (2-[[8-chloro-3,4-dihydro-4-(4-methoxyphenyl)-3-oxo-2-quinoxalinyl]carbonyl]-1,3-cyclohexanedione), isoxachlortole, isoxaflutole, mesotrione, pyrasulfotole, pyrazolynate, pyrazoxyfen, sulcotrione, tefuryltrione, tembotrione, tolpyralate (1-[[1-ethyl-4-[3-(2-methoxyethoxy)-2-methyl-4-(methylsulfonyl)benzoyl]-1H-pyrazol-5-yl]oxy]ethyl methyl carbonate), topramezone, 5-chloro-3-[(2-hydroxy-6-oxo-1-cyclohexen-1-yl)carbonyl]-1-(4-methoxyphenyl)-2(1H)-quinoxalinone, 4-(2,6-diethyl-4-methylphenyl)-5-hydroxy-2,6-dimethyl-3(2H)-pyridazinone, 4-(4-fluorophenyl)-6-[(2-hydroxy-6-oxo-1-cyclohexen-1-yl)carbonyl]-2-methyl-1,2,4-triazine-3,5(2H,4H)-dione, 5-[(2-hydroxy-6-oxo-1-cyclohexen-1-yl)carbonyl]-2-(3-methoxyphenyl)-3-(3-methoxypropyl)-4(3H)-pyrimidinone, 2-methyl-N-(4-methyl-1,2,5-oxadiazol-3-yl)-3-(methylsulfinyl)-4-(trifluoromethyl)benzamide and 2-methyl-3-(methylsulfonyl)-N-(1-methyl-1H-tetrazol-5-yl)-4-(trifluoromethyl)benzamide.

"HST inhibitors" (b13) disrupt a plant's ability to convert homogentisate to 2-methyl-6-solanyl-1,4-benzoquinone, thereby disrupting carotenoid biosynthesis. Examples of HST inhibitors include cyclopyrimorate (6-chloro-3-(2-cyclopropyl-6-methylphenoxy)-4-pyridazinyl 4-morpholinecarboxylate), haloxydine, pyriclor, 3-(2-chloro-3,6-difluorophenyl)-4-hydroxy-1-methyl-1,5-naphthyridin-2(1H)-one, 7-(3,5-dichloro-4-pyridinyl)-5-(2,2-difluoroethyl)-8-hydroxypyrido[2,3-b]pyrazin-6(5H)-one and 4-(2,6-diethyl-4-methylphenyl)-5-hydroxy-2,6-dimethyl-3(2H)-pyridazinone.

HST inhibitors also include compounds of Formulae A and B.

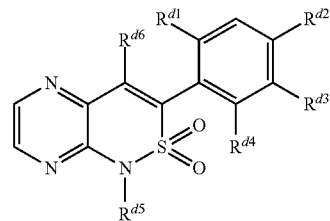

A

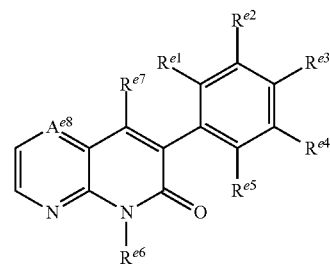

B wherein $R^{d1}$ is H, Cl or $CF_3$; $R^{d2}$ is H, Cl or Br; $R^{d3}$ is H or Cl; $R^{d4}$ is H, Cl or $CF_3$; $R^{d5}$ is $CH_3$, $CH_2CH_3$ or $CH_2CHF_2$; and $R^{d6}$ is OH, or —OC(=O)-i-Pr; and $R^{e1}$ is H, F, Cl, $CH_3$ or $CH_2CH_3$; $R^{e2}$ is H or $CF_3$; $R^{e3}$ is H, $CH_3$ or $CH_2CH_3$; $R^{e4}$ is H, F or Br; $R^{e5}$ is Cl, $CH_3$, $CF_3$, $OCF_3$ or $CH_2CH_3$; $R^{e6}$ is H, $CH_3$, $CH_2CHF_2$ or C≡CH; $R^{e7}$ is OH, —OC(=O)Et, —OC(=O)-i-Pr or —OC(=O)-t-Bu; and $A^{e8}$ is N or CH.

"Cellulose biosynthesis inhibitors" (b14) inhibit the biosynthesis of cellulose in certain plants. They are most effective when applied preemergence or early postemergence on young or rapidly growing plants. Examples of cellulose biosynthesis inhibitors include chlorthiamid, dichlobenil, flupoxam, indaziflam ($N^2$-[(1R,2S)-2,3-dihydro-2,6-dimethyl-1H-inden-1-yl]-6-(1-fluoroethyl)-1,3,5-triazine-2,4-diamine), isoxaben and triaziflam.

"Other herbicides" (b15) include herbicides that act through a variety of different modes of action such as mitotic disruptors (e.g., flamprop-M-methyl and flamprop-M-isopropyl), organic arsenicals (e.g., DSMA, and MSMA), 7,8-dihydropteroate synthase inhibitors, chloroplast isoprenoid synthesis inhibitors and cell-wall biosynthesis inhibitors. Other herbicides include those herbicides having unknown modes of action or do not fall into a specific category listed in (b1) through (b14) or act through a combination of modes of action listed above. Examples of other herbicides include aclonifen, asulam, amitrole, bromobutide, cinmethylin, clomazone, cumyluron, daimuron, difenzoquat, etobenzanid, fluometuron, flurenol, fosamine, fosamine-ammonium, dazomet, dymron, ipfencarbazone (1-(2,4-dichlorophenyl)-N-(2,4-difluorophenyl)-1,5-dihydro-N-(1-methylethyl)-5-oxo-4H-1,2,4-triazole-4-carboxamide), metam, methyldymron, oleic acid, oxaziclomefone, pelargonic acid, pyributicarb and 5-[[(2,6-difluorophenyl)methoxy]methyl]-4,5-dihydro-5-methyl-3-(3-methyl-2-thienyl)isoxazole.

"Herbicide safeners" (b16) are substances added to a herbicide formulation to eliminate or reduce phytotoxic effects of the herbicide to certain crops. These compounds protect crops from injury by herbicides but typically do not prevent the herbicide from controlling undesired vegetation. Examples of herbicide safeners include but are not limited to benoxacor, cloquintocet-mexyl, cumyluron, cyometrinil, cyprosulfamide, daimuron, dichlormid, dicyclonon, dietholate, dimepiperate, fenchlorazole-ethyl, fenclorim, flurazole, fluxofenim, furilazole, isoxadifen-ethyl, mefenpyr-diethyl, mephenate, methoxyphenone, naphthalic anhydride, oxabetrinil, N-(aminocarbonyl)-2-methylbenzenesulfonamide and N-(aminocarbonyl)-2-fluorobenzenesulfonamide, 1-bromo-4-[(chloromethyl)sulfonyl]benzene, 2-(dichloromethyl)-2-methyl-1,3-dioxolane (MG 191), 4-(dichloroacetyl)-1-oxa-4-azospiro[4.5]decane (MON 4660), 2,2-dichloro-1-(2,2,5-trimethyl-3-oxazolidinyl)-ethanone and 2-methoxy-N-[[4-[[(methylamino)carbonyl]amino]phenyl]sulfonyl]-benzamide.

The compounds of Formula 1 can be prepared by general methods known in the art of synthetic organic chemistry. One or more of the following methods and variations as described in Schemes 1-16 can be used to prepare the compounds of Formula 1. The definitions of (insert variables) in the compounds of Formulae 1-25 below are as defined above in the Summary of the Invention unless otherwise noted. Compounds of Formulae 1A-1D are various subsets of the compounds of Formula 1, and all substituents for Formulae 1A-1D are as defined above for Formula 1 unless otherwise noted. Compounds of Formulae 2A-2I are various subsets of the compounds of Formula 1, and all substituents for Formulae 2A-2I are as defined above for Formula 2 unless otherwise noted. Compounds of Formulae 7A-7B are various subsets of the compounds of Formula 7, and all substituents for Formulae 7A-1B are as defined above for Formula 7 unless otherwise noted.

As shown in Scheme 1 a compound of Formula 1 can be prepared by nucleophilic substitution by heating a compound of Formula 2 in a suitable solvent, such as acetonitrile, tetrahydrofuran or N,N-dimethylformamide in the presence of a base such as potassium or cesium carbonate, at temperatures ranging from 50 to 110° C., with a compound of Formula 3 (where LG is halogen or $SO_2Me$). The reaction is typically conducted at temperatures ranging from 50 to 110° C.

Scheme 1

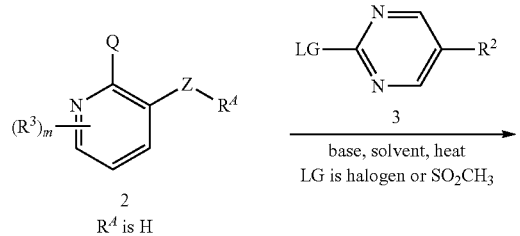

$R^A$ is H

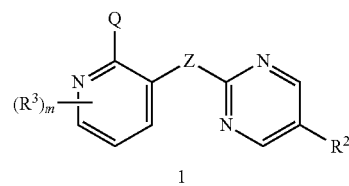

Alternatively, as shown in Scheme 2, boron compounds of Formula 5 or tin compounds of Formula 6 can be coupled with intermediates of Formula 4 under Suzuki or Stille conditions to give compounds of carbon linked compounds of Formula 1. Suzuki couplings typically are conducted in the presence of Pd(0) or Pd(II) salts, a suitable ligand, and a base. Suitable bases for this transformation include potassium carbonate or cesium carbonate, while Pd(II) salts such as $Pd(OAc)_2$ or $PdCl_2$ can be used in conjunction with ligands such as triphenylphosphine or 1,1'-bis(diphenylphosphino)ferrocene (dppf). Conditions for Suzuki couplings are well documented in the literature (see for example *Angewandte Chemie International Edition* 2006, 45, 3484 and *Tetrahedron Letters* 2002, 58(14), 2885). Boron intermediates of Formula 5 are commercially available or can be prepared from the corresponding halides or trifluoromethanesulfonates by methods known in the literature (see for example PCT Patent Publication WO 2007/043278, U.S. Pat. No. 8,080,566, *Organic Letters* 2011, 13(6), 1366 and *Organic Letters* 2012, 14(2), 600). Stille couplings typically can be conducted in the presence of Pd(0) or a Pd(II) salt, a ligand and a Cu(I) salt such as copper(I) iodide. The reaction can be run in a solvent such as dioxane, 1,2-dimethoxyethane or toluene at a temperature ranging from ambient to reflux. For conditions and reagents employed in Stille couplings see *Chemical Reviews* 2007, 107(1), 133-173.

Scheme 2

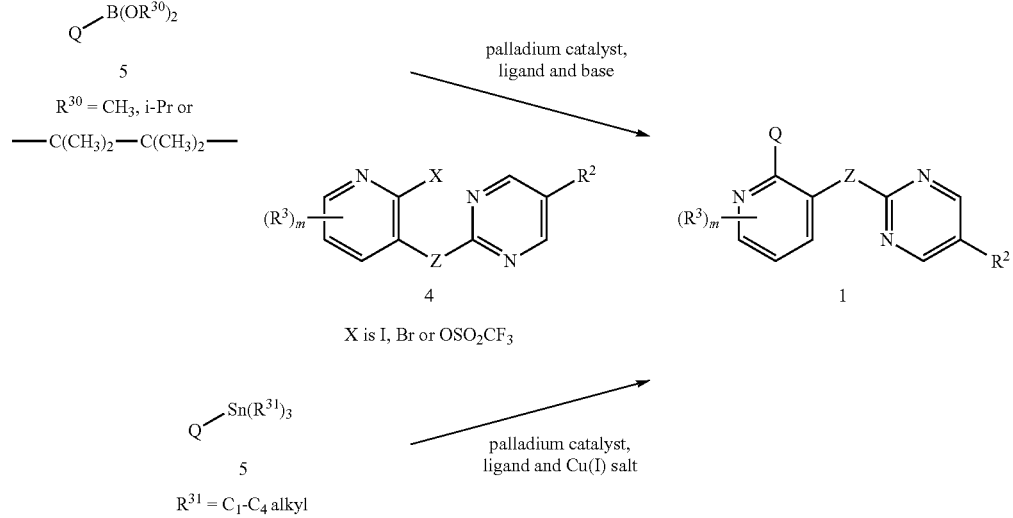

As shown in Scheme 3, a compound of Formula 2A (i.e. a compound of Formula 2 wherein Z is O, $R^A$ is H or lower alkyl and Q is a heterocycle connected via a nitrogen atom) can be prepared using a Buchwald copper(I) catalyzed carbon-nitrogen bond forming reaction in the presence of a ligand such as ethylene diamine or cyclohexane diamine by heating a compound of Formula 7 (wherein $X^1$ is I or Br) in a suitable solvent, such as toluene, 1,4-dioxanes or N,N-dimethylformamide in the presence of a base such as potassium carbonate, cesium carbonate or tribasic potassium phosphate, with a compound of Formula 8 (i.e. an aromatic 5-membered heterocycle with a free NH group). The reaction is typically conducted at about 110° C. as described for copper-catalyzed carbon-nitrogen bond formation methods using diamine ligands found in Surry and Buchwald, *Chemical Science* 2010, 1, 13-31. One skilled in the art can prepare a compound of Formula 8 by means found in *Comrehensive Heterocyclic Chemistry*, Part II, 1996, parts 2, 3 & 4, Pergamon Press, publisher, edited by Alan. R. Katritzky & Charles W. Reese and CHC, Part I, 1984 and series of *The Chemistry of Heterocyclic Compounds,* 1981, publisher John Wiley & sons and Interscience Publishers Inc, 1953.

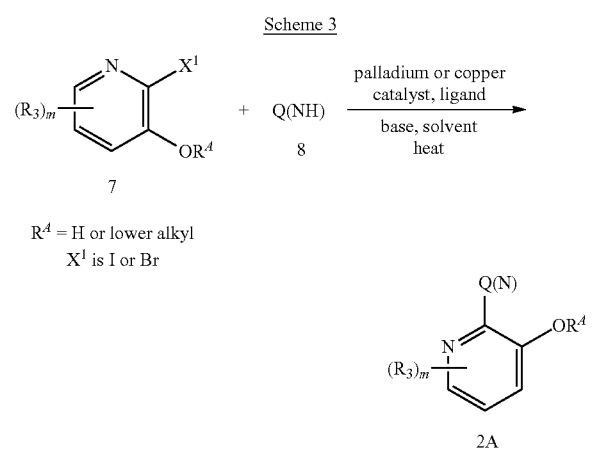

Scheme 3 wherein Q is equal to Q-7, Q-17, Q-27, Q-33, Q-34, Q-46, Q-47, Q-50 and Q-51

Phosphine ligands can also be employed for palladium-catalyzed amination reactions to prepare a compound of Formula 2A. A review of suitable ligands, bases, solvents, catalysts and substrates for use with NH-containing heterocycles (i.e. a compound of Formula 8) can be found in Surry and Buchwald, *Chemical Science* 2011, 2, 27-50 and references cited therein. In particular, conditions for pyrazoles and imidazoles with aryl or heteroaryl halides using a palladium catalyst such as $Pd_2(dba)_3$, with ligands such as 2-di-t-butylphophino-2',4',6'-triisopropylbiphenyl (i.e. t-Bu-X-Phos) or 2-di-t-butylphophino-3,4,5,6-tetramethyl-2',4', 6'-triisopropylbiphenyl (i.e. $Me_4$-t-Bu-X-Phos) with bases such as $Na^+$—O-t-Bu or $K_3PO_4$ in solvents such as toluene or 1,4-dioxane at temperatures ranging from 60 to 105° C. are described. Alternative synthetic strategies can also be found in Sorokin, *Mini-Reviews in Organic Chemistry* 2008, 5, 323-330; Bellina and Rossi, *Advanced Synthesis & Catalysis* 2010, 352, 1223-1276, and Beletskaya and Cheprakov, *Organometallics* 2012, 31, 7753-7808.

As shown in Scheme 4, a compound of Formula 2B (i.e. a compound of Formula 2 wherein Z is O, $R^A$ is H or lower alkyl and Q is a heterocycle connected via a carbon atom) can also be prepared by direct nucleophilic displacement by heating a compound of Formula 7A, (i.e. a compound of Formula 7 wherein $X^1$ is F or Cl) in a suitable solvent such as N,N-dimethylformamide, N,N-dimethylacetamide or N-methylpyrrolidinone and in the presence of a base such as potassium or cesium carbonate with a compound of Formula 5. The reaction is typically conducted at temperatures ranging from 80 to 160° C. but the transformation can be accomplished at higher or lower temperatures depending on the nature of the $R^3$ substituents and $X^1$.

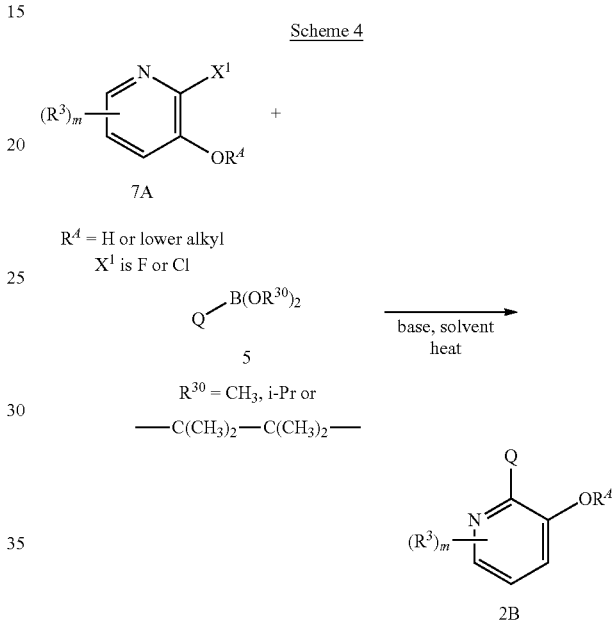

Scheme 4

As shown in Scheme 5, a compound of Formula 2D (i.e. a compound of Formula 2 where Z is O and $R^A$ is H) can be prepared by deprotection of a compound of Formula 2C (i.e. a compound of Formula 2A wherein Z is O; and $R^A$ is $CH_3$ or —C(═O)$CH_3$) with a suitable deprotecting agent. Suitable methoxy (i.e. when $R^A$ is $CH_3$) deprotecting reagents such as $BBr_3$, $AlCl_3$ and HBr in acetic acid can be used in the presence of solvents such as toluene, dichloromethane and dichloroethane at a temperature of from −80 to 120° C. Suitable acetoxy (i.e. when $R^A$ is —C(═O)$CH_3$) deprotecting agents include potassium carbonate in methanol or ammonium acetate in aqueous methanol at room temperature can be used as discussed in Das, et al., *Tetrahedron* 2003, 59, 1049-1054 and methods cited therein. Alternatively, a compound of Formula 2C can be combined with Amberlyst 15© in methanol (as discussed in Das, et al. *Tet. Lett.* 2003, 44, 5465-5468) or combined with sodium acetate in ethanol (as discussed in Narender, T., et al. *Synthetic Communications* 2009, 39(11), 1949-1956) to obtain a compound of Formula 2D. Other useful phenolic protecting groups suitable for use in preparing a compound of Formula 2D can be found in Greene, T. W.; Wuts, P. G. M. *Protective Groups in Organic Synthesis,* 4th ed.; Wiley: Hoboken, N.J., 1991.

Scheme 5

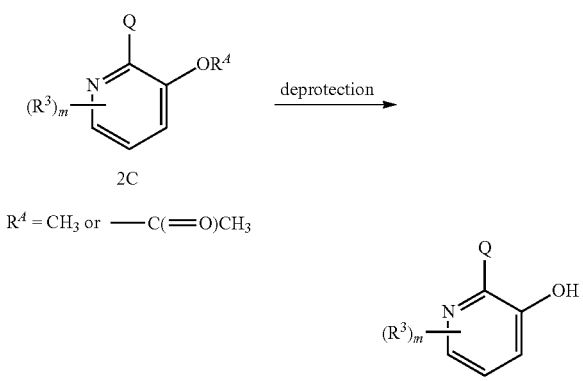

An intermediate of Formula 2C can be prepared as shown in Scheme 6 from an intermediate of Formula 9 by a variety of methods known to one skilled in the art. Compounds of Formula 2C can be accessed by coupling precursors of Formula 9 wherein J is Br, Cl, I or trifluoromethanesulfonate with boronate or trialkyltin group-containing heterocycles (i.e compounds of Formula 5 or Formula 6 using the Suzuki conditions or the Stille conditions of Scheme 2).

Alternatively, compounds of Formula 9 wherein J is a boronate or trialkyltin group may be coupled with halogen-substituted heterocycles Q-X$^2$ wherein X$^2$ is Br or I, using the methods shown in Scheme 2 to afford compounds of Formula 2C. The skilled chemist will realize that with the prudent choice of groups X$^2$ and J in reactions involving compounds of Formula 9 and Q-X$^2$ can synthesize the intermediate 2C utilizing various cross coupling procedures such as Kumada coupling, Hiyama coupling or Negishi coupling described in "Metal-Catalyzed Cross-Coupling Reactions", Eds. A. de Meijere and F. Diederich, Wiley-VCH, Weinheim, 2004, vols 1 and 2.

When J in Formula 9 is an alkene, alkyne, oxime, nitrile or ketone, various Q heterocycles can be prepared using methods described in Katritsky, *Advances in Heterocyclic Chemistry*, Vol. 1-104, Elsevier. In cases where regioisomeric mixtures are produced, the desired product can be isolated using routing separation techniques known in the art.

Scheme 6

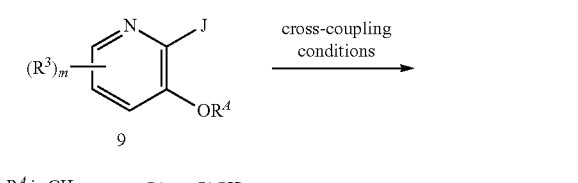

As shown in Scheme 7, a compound of Formula 7B can be prepared by coupling of phenols of Formula 10 with a compound of Formula 3 under the nucleophilic substitution conditions described in Scheme 1.

Scheme 7

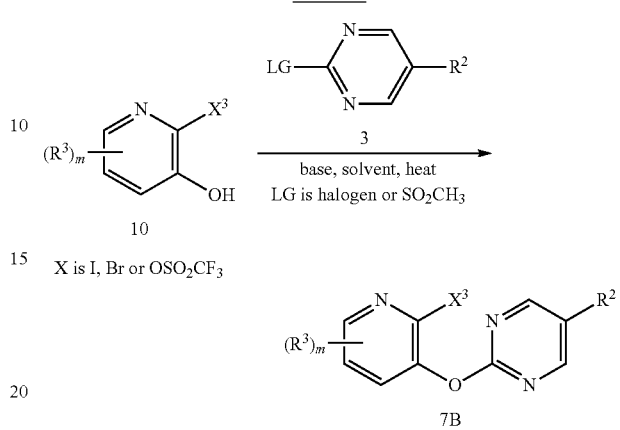

Chemistry based on "C—H activation" can also be used to prepare a compound of Formula 2E (i.e. a compound of Formula 2 wherein Z is O; R$^4$ is —C(O)CH$_3$) as shown in Scheme 8 utilizing palladium(II) acetate and (diacetoxyiodo)benzene. Compounds of Formula 2E can be converted into compounds of Formula 2D by hydrolysis using aqueous acid or base. A compound of Formula 2D can subsequently be converted via methods disclosed in Scheme 1 to provide a compound of Formula 1A (i.e. a compound of Formula 1 wherein Z is O). These methods are detailed in reviews of selective activation of C—H bonds in *Chemical Reviews* 2010, 110, 575-1211 and references cited therein. Methods for "C—H activation" can also be found in Wencel-Delord et al., *Nature Chemistry* 2013, 5, 369-375 and a series of reviews of "C—H activation" in *Accounts of Chemical Research* 2012, 45, 777-958 and references cited therein.

Scheme 8

Similarly, chemistry based on "C—H activation" can be used to prepare a compound of Formulae 2F (i.e. a compound of Formula 2 wherein Z is S) as shown in Scheme 9. A compound of Formula 11 can first be converted to a compound of Formula 12 (wherein X$^4$ is Br or I) by utilizing a stepwise introduction of substituents using "C—H activation".

Iodides and bromides of Formula 12 can then be further functionalized by copper mediated cross-coupling with thio-urea as described in Qi, Junsheng, *Chin. J. Chem.* 2010, 28, 1441-1443 to provide the aryl thiol after acidic deprotection. Palladium catalyzed cross-coupling reactions of aryl halides can give protected thiols that can, in turn, be deprotected under either acidic conditions or basic conditions (e.g. cesium fluoride) to provide a compound of Formula 2F. These conditions are discussed in Organ, Michael G., *Angew. Chem. Int. Ed.* 2012, 51, 3314-3322 and the references cited therein. Also, relevant conditions can be found in Takashiro Itoh, *J. Org. Chem.* 2006, 71, 2203-2206. A compound of Formula 2F can then be converted via methods disclosed in Scheme 1 to provide a compound of Formula 1.

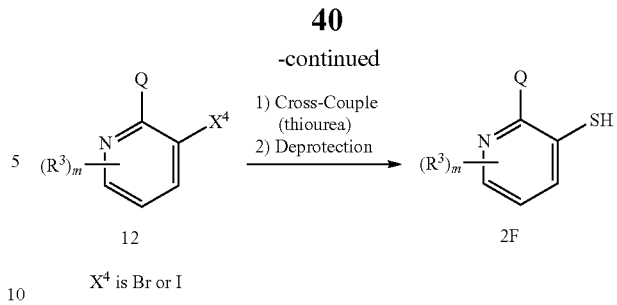

$X^4$ is Br or I

In Scheme 10, isoxazoles of Formulae 2G and 2H (i.e. a compound of Formula 2 wherein Z is O, $R^A$ is $CH_3$, Q is Q-18 and Q-20 and $R^{1a}$ and $R^{1b}$ are substituents on Q) can be synthesized beginning with compounds of Formula 13 or 14. A compound of Formula 13 can be reacted with ester 15 using a base such as sodium methoxide or sodium hydride in a solvent such as tetrahydrofuran to afford a compound of Formula 17. Conversely a compound of Formula 14 can be reacted with a compound of Formula 16 under similar conditions to afford a compound of Formula 17. This type of reaction is commonly referred to as a 'Claisen Condensation' and well known to those skilled in the art. Reaction of a compound of Formula 17 with hydroxylamine hydrochloride in solvents such as ethanol, N,N-dimethylformamide, or tetrahdrofuran under neutral, acidic (example of acids: trifluoroacetic acid, hydrochloric acid, sulfuric acid) or basic (examples of bases: sodium hydroxide, sodium acetate, pyridine) to give varying mixtures of 2G and 2H dependent upon the nature of $R^{1a}$ and $R^{1b}$.

Scheme 9

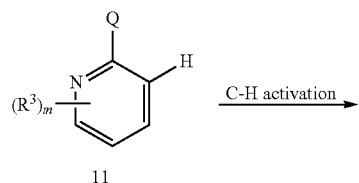

Scheme 10

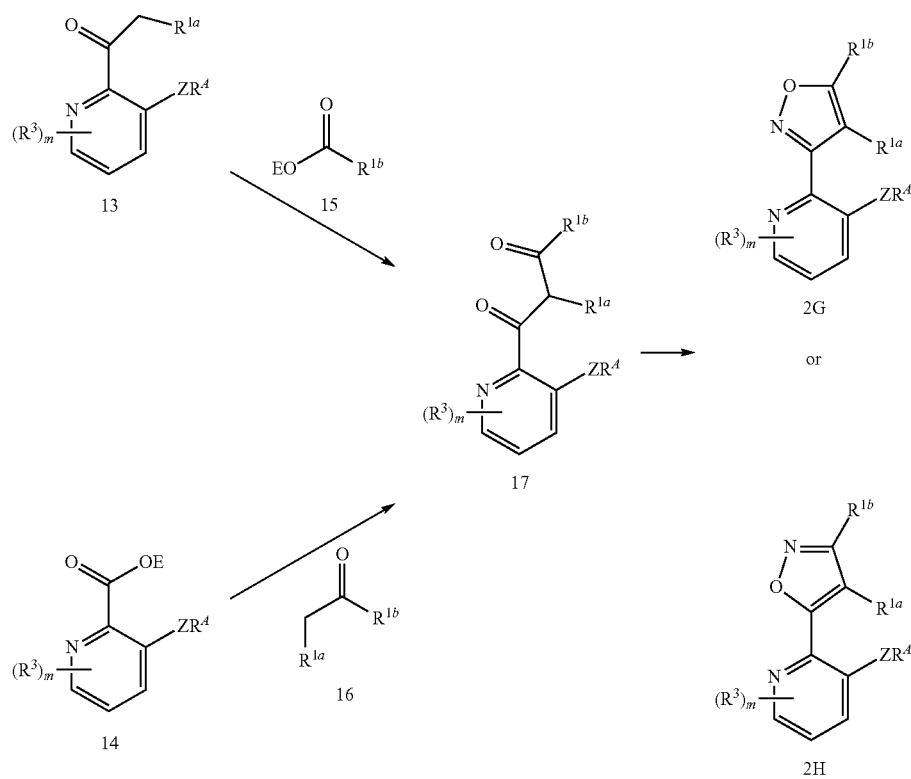

wherein $R^A$ is $CH_3$ and E is $CH_3$ or $CH_2CH_3$

In Scheme 11, the phenol, 2D is reacted with N,N-dimethyl thiocarbamoyl chloride in N,N-dimethylformamide in the presence of a strong tertiary amine base such as 1,4-diazabicyclo[2.2.2]octane or N-methylmorpholine for acidic phenols (for less-acidic phenols, prior deprotonation with sodium hydride may be advantageous) to form the O-aryl N,N-dimethylthiocarbamate of Formula 18. Newman-Kwart rearrangement of a compound of Formula 18 at temperatures ranging from 200 to 300° C. provides the intermediate S-aryl dimethylthiocarbamate of Formula 19. A one-pot deprotection of a compound of Formula 19 is readily achieved using 10% aqueous sodium hydroxide or methanolic potassium hydroxide to afford the corresponding aryl thiol. Subsequent reaction with a compound of Formula 3 at or slightly above room temperature provides the product 1B (i.e. a compound of Formula 1 wherein Z is S). Methods for Newman-Kwart rearrangements are found in Lloyd-Jones, Guy C., *Synthesis* 2008, 661-689.

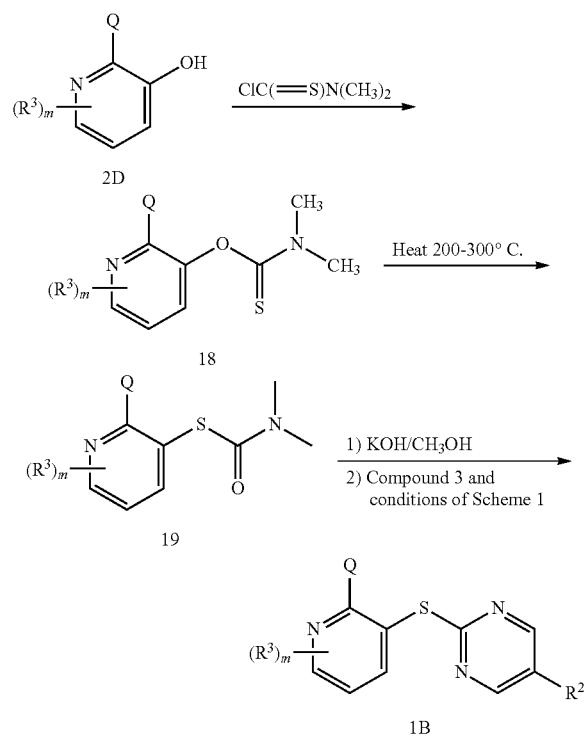

Functionalization of the Q group of Compounds of Formula 1 or intermediates of Formula 2 may also be accomplished by means of electrophilic substitution. Reagents capable of electrophilic substitution such as N-halosuccinimides, sulfuryl halides and elemental halogens can be used in compatible solvents such as N,N-dimethylformamide or acetonitrile at temperatures from 20 to 120° C. to introduce substituents at reactive positions of the Q group.

Functionalization of the Q group may also be accomplished by means of suitable cross-coupling methods as described in V. Snieckus et al., *Angew. Chem. Int. Ed.* 2012, 51, 5062-5086 or *Accounts of Chemical Research* 2008, 41, 11, 1439-1564 and references cited therein. These methods involve selection of an appropriate catalyst and reagent system for converting a $R^1$ halogen substituent. For palladium-catalyzed cross coupling reactions suitable for use with these types of Q groups see Gribble and Li Eds., *Palladium in Heterocyclic Chemistry* Volume 1, Pergamon Press, 2000, Gribble and Li, Eds., *Palladium in Heterocyclic Chemistry* Volume 2, Pergamon Press, 2007 and deMeijere and Diederich Eds., *Metal-Catalyzed Cross-Coupling Reactions*, Second Edition, John Wiley and Sons, 2004.

Products of Formula 2I (a compound of Formula 2 wherein Q is Q-47) can be prepared by the methods shown in Scheme 12. Phenyl hydrazines of Formula 20 can be reacted with glyoxal in acetic acid followed by hydroxyl amine in ethanol to form arylhydrazone oxime intermediates of Formula 21. Reaction of a compound of Formula 21 in pyridine with a copper salt such as copper sulphate provides the 2-aryltriazole-1-oxide intermediates of Formula 22. Treatment of a compound of Formula 22 with trimethyloxonium tetrafluoroborate yields a 1-methoxy-2-phenyltriazolium salts that can react with $R^1$ nucleophiles (for example halides, cyanides or alkoxides) to produce a compound of Formula 2I, (i.e. a compound of Formula 2 wherein Z is O and $R^4$ is a suitable protecting group such as benzyl or $CH_3$). This route can also be used for substituted dicarbonyl compounds or their monooximes in place of glyoxal which result in compounds of Formula 22 where $R^1$ can be various alkyls after reduction of the N-oxide. For specific examples of this sequence with a variety of dicarbonyl compounds and nucleophiles, see M. Begtrup in *J. Chem. Society, Perkin Trans. I* 1981, 503-513 and *Bull. Soc. Chim. Belg.* 1997, 106, 717-727.

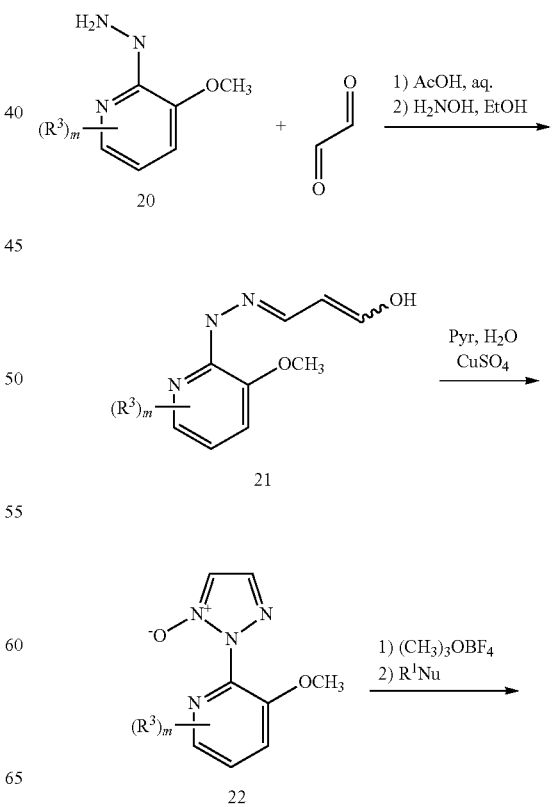

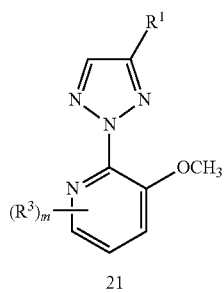

As shown in Scheme 13 compounds of Formula 1C (a compound of Formula 1 wherein Q is Q-46) can be prepared by the coupling of an alkyne with an azide of Formula 23. This type of reaction is commonly referred to as 'click chemistry' and well known to those skilled in the art. A review of suitable conditions and catalysts for the coupling of alkynes with azides (i.e. a compound of Formula 23) can be found in Meldal and Tomoe in *Chemial Reviews* 2008, 108, 2952-3015 and references cited therein. Suitable conditions generally include a copper catalyst with ligands such as halides and ascorbate in a variety of organic solvents such as tert-butanol, methanol, dimethylsulfoxide, dimethyl formamide in addition to water. The regioselectivitiy of this coupling can be dependent upon the nature of $R^1$ however this can be controlled with the choice of reaction conditions such as metalating a terminal alkyne. Also note that the two $R^1$ groups on the alkyne need not be identical. For an example see Krasinski, Fokin, and Sharpless in *Organic Letters*, 2004, 6, 1237-1240.

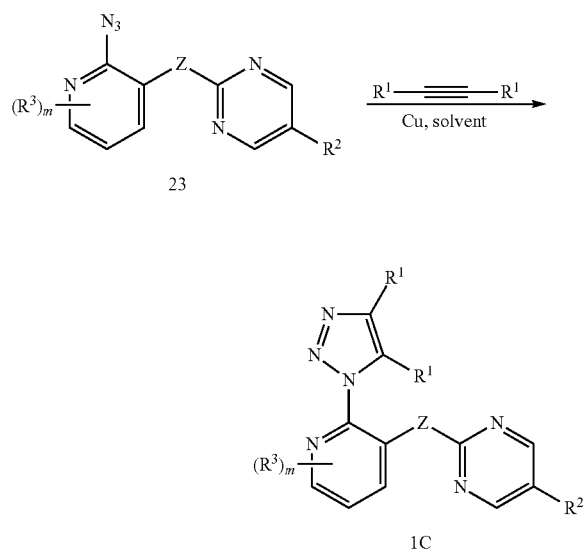

Scheme 13

As shown in Scheme 14, a compound of Formula 23 can be prepared from a compound of Formula 24 using the same methods as described in Scheme 1.

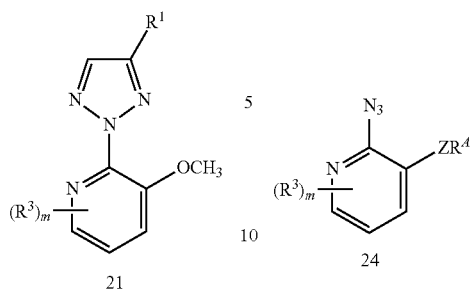

Scheme 14

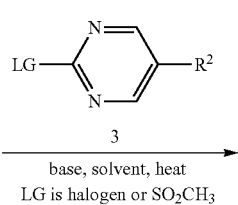

As shown in Scheme 15 compounds of Formula 24 can be prepared by diazotisation of an amine of Formula 25 followed by substitution with azide using methods well known to those skilled in the art. Descriptions of how this transformation can be achieve are described in Wu, Zhao, Lan, Cao, Liu, Jinag, and Li in *The Journal of Organic Chemistry* 2012, 77, 4261-4270 or in Barral, Moorhouse, and Moses in *Organic Letters* 2007, 9, 1809-1811. Examples of suitable reagents for diazotization include sodium nitrite and tert-butyl nitrite, and suitable examples of azide sources include sodium azide and trimethylsilyl azide.

Scheme 15

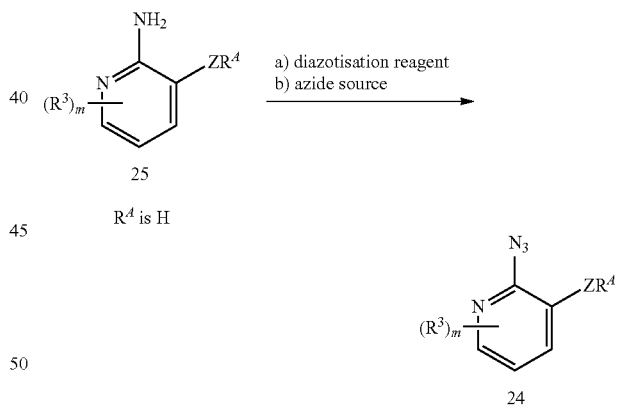

As shown in Scheme 16 compounds of Formula 1 can be oxidized to provide the pyridine N-oxide compounds of Formula 1D) using methods well known to those skilled in the art (see, for example, Smith, M. B.; March, J. *March's Advanced Organic Chemistry*, 6th ed; John Wiley & Sons: Hoboken, N.J. and references therein). Examples of oxidants that can be used to achieve this transformation include peroxyacids, urea-$H_2O_2$ in solvents such as dichloromethane, methanol, tetrahydrofuran and acetonitrile. Alternatively oxidant-catalyst combinations can also be used to achieve for example, combination of ruthenium catalysts with oxidants such as $O_2$ or peroxides in solvents such as dichloromethane, methanol, tetrahydrofuran, acetonitrile, and water.

Scheme 16

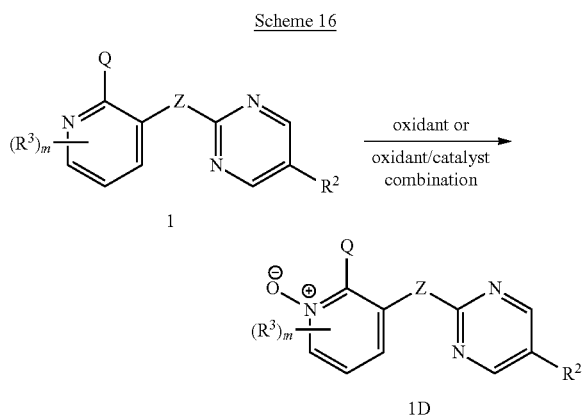

It is recognized by one skilled in the art that various functional groups can be converted into others to provide different compounds of Formula 1. For a valuable resource that illustrates the interconversion of functional groups in a simple and straightforward fashion, see Larock, R. C., *Comprehensive Organic Transformations: A Guide to Functional Group Preparations*, 2nd Ed., Wiley-VCH, New York, 1999. For example, intermediates for the preparation of compounds of Formula 1 may contain aromatic nitro groups, which can be reduced to amino groups, and then be converted via reactions well known in the art such as the Sandmeyer reaction, to various halides, providing compounds of Formula 1. The above reactions can also in many cases be performed in alternate order It is recognized that some reagents and reaction conditions described above for preparing compounds of Formula 1 may not be compatible with certain functionalities present in the intermediates. In these instances, the incorporation of protection/deprotection sequences or functional group interconversions into the synthesis will aid in obtaining the desired products. The use and choice of the protecting groups will be apparent to one skilled in chemical synthesis (see, for example, Greene, T. W.; Wuts, P. G. M. *Protective Groups in Organic Synthesis*, 2nd ed.; Wiley: New York, 1991). One skilled in the art will recognize that, in some cases, after the introduction of a given reagent as depicted in any individual scheme, it may be necessary to perform additional routine synthetic steps not described in detail to complete the synthesis of compounds of Formula 1. One skilled in the art will also recognize that it may be necessary to perform a combination of the steps illustrated in the above schemes in an order other than that implied by the particular presented to prepare the compounds of Formula 1.

One skilled in the art will also recognize that compounds of Formula 1 and the intermediates described herein can be subjected to various electrophilic, nucleophilic, radical, organometallic, oxidation, and reduction reactions to add substituents or modify existing substituents.

Without further elaboration, it is believed that one skilled in the art using the preceding description can utilize the present invention to its fullest extent. The following non-limiting Examples are illustrative of the invention. Steps in the following Examples illustrate a procedure for each step in an overall synthetic transformation, and the starting material for each step may not have necessarily been prepared by a particular preparative run whose procedure is described in other Examples or Steps. Percentages are by weight except for chromatographic solvent mixtures or where otherwise indicated. Parts and percentages for chromatographic solvent mixtures are by volume unless otherwise indicated. $^1$H NMR spectra are reported in ppm downfield from tetramethylsilane; "s" means singlet, "d" means doublet, "t" means triplet, "q" means quartet, "m" means multiplet, "dd" means doublet of doublets, "dt" means doublet of triplets, and "br s" means broad singlet. Mass spectra (MS) are reported as the molecular weight of the highest isotopic abundance parent ion (M+1) formed by addition of H+ (molecular weight of 1) to the molecule, or (M−1) formed by the loss of H+ (molecular weight of 1) from the molecule, observed by using liquid chromatography coupled to a mass spectrometer (LCMS) using either atmospheric pressure chemical ionization (AP+) where "amu" stands for unified atomic mass units.

Example 1

Preparation of 5-chloro-2-[[2-[5-(difluoromethyl)-3-isoxazolyl]-3-pyridinyl]oxy]pyrimidine (Compound 6) and 5-chloro-2-[[2-[5-(difluoromethyl)-3-isoxazolyl]-1-oxido-3-pyridinyl]oxy]pyrimidine (Compound 8)

Step A: Preparation of 3-(3-fluoro-2-pyridinyl)-5-isoxazolemethanol

To a solution of 3-fluoropyridine-2-carbaldehyde (0.50 g, 4.0 mmol) in ethanol (6 mL) was added hydroxylamine hydrochloride (0.42 g, 6.0 mmol) followed by sodium acetate (0.66 g, 8.0 mmol) and the reaction stirred for 30 min at room temperature. The reaction was partitioned between ethyl acetate and water, the organic phase was dried with magnesium sulfate and concentrated under vacuum to provide the desired product (0.40 g) which was taken on directly in the next step. To a solution of 3-fluoropyridine-2-carbaldehyde oxime (10.0 g, 71.4 mmol) in ethyl acetate (100 mL) at 0° C. was added N-chlorosuccinamide (18.2 g, 214 mmol). The mixture was stirred for 1 hr. Then propargylic alcohol (14.3 g, 107.1 mmol) and sodium bicarbonate (6.12 g, 107.1 mmol) were added and the reaction stirred at room temperature for 16 hours. The reaction mixture was partitioned with water, and the organic phase was washed with water and saturated aqueous sodium chloride. The organic phase was dried with magnesium sulfate and concentrated under vacuum. The residue was purified by chromatography on silica gel, eluting with 20% ethyl acetate in petroleum ether to afford the title compound (7.0 g).

$^1$H NMR (400 MHz, CDCl$_3$) δ 8.59-8.54 (m, 1H), 7.58 (t, 1H), 7.42 (dt, 1H), 6.90 (s, 1H), 4.88 (d, 2H), 2.18 (br t, 1H). MS (M+H)=195

Step B: Preparation of 3-(3-fluoro-2-pyridinyl)-5-isoxazolecarboxaldehyde

To a solution of 3-(3-fluoro-2-pyridinyl)-5-isoxazolemethanol (i.e. the product of Step A) (0.20 g, 1.0 mmol) in anhydrous dichloromethane (10 mL) was added Dess Martin Periodinane (1,1,1-triacetoxy-1,1-dihydro-1,2-benziodoxol-3(1H)-one) (0.52 g, 1.2 mmol) and the reaction stirred at room temperature for 2 hours. The reaction was partitioned with water and washed with a saturated solution of sodium bicarbonate. The organic phase was dried with magnesium sulfate and concentrated under vacuum. The residue was purified by chromatography on silica gel, eluting with 20% ethyl acetate in petroleum ether to afford the title compound (0.1 g).

¹H NMR (300 MHz, DMSO-d6) δ 10.01 (s, 1H), 8.66 (br d, 1H), 8.07-7.97 (m, 1H), 7.86 (s, 1H), 7.71 (dt, 1H).

Step C: Preparation of 3-(3-methoxy-2-pyridinyl)-5-isoxazolecarboxaldehyde

To a solution of 3-(3-fluoro-2-pyridinyl)-5-isoxazolecarboxaldehyde (i.e. the product of Step B) (0.50 g, 2.6 mmol) in methanol (10 mL) was added sodium methoxide in methanol solution (0.70 g, 13.0 mmol) and the reaction was heated to 90° C. for 7 hours. The reaction was partitioned between water and ethyl acetate, the organic phase was separated, dried with magnesium sulfate, and concentrated under vacuum. The residue was purified by chromatography on silica gel, eluting with 50% ethyl acetate in petroleum ether to afford the title compound (0.30 g).
¹H NMR (400 MHz, DMSO-d6) δ 9.98 (s, 1H), 8.34 (dd, 1H), 7.79-7.76 (m, 1H) 7.76-7.71 (m, 1H), 7.61-7.55 (m, 1H), 3.94 (s, 3H). MS (M+H)=205

Step D: Preparation of 2-[5-(difluoromethyl)-3-isoxazolyl]-3-methoxypyridine

To a solution of 3-(3-methoxy-2-pyridinyl)-5-isoxazolecarboxaldehyde (i.e. the product of Step C) (0.20 g, 0.97 mmol) in anhydrous dichloromethane (6.0 mL) was added diethylaminosulfur trifluoride (0.31 g, 1.95 mmol) at 0° C. and the reaction was allowed to warm to room temperature over 45 minutes. The reaction was partitioned between water and dichloromethane, the organic phase was collected, dried with magnesium sulfate, and concentrated under vacuum. The residue was purified by chromatography on silica gel, eluting with 50% ethyl acetate in petroleum ether to afford the title compound (40 mg).
¹H NMR (400 MHz, CDCl₃) δ 8.40-8.33 (m, 1H), 7.40 (d, 2H), 7.25-7.21 (m, 1H), 6.99-6.65 (m, 1H), 3.99 (s, 3H). MS (M+H)=227

Step E: Preparation of 2-[5-(difluoromethyl)-3-isoxazolyl]-3-pyridinol

To a solution of 2-[5-(difluoromethyl)-3-isoxazolyl]-3-methoxypyridine (i.e. the product of Step D) (80 mg, 0.35 mmol) in anhydrous dichloromethane (6.0 mL) at 0° C. was added a 1 molar solution of boron tribromide (0.44 g, 1.8 mmol) and the reaction was allowed to warm to room temperature over 3 hours. The reaction was treated with ice, followed by partitioning between water and dichloromethane. The organic phase was collected, dried with magnesium sulfate, and concentrated under vacuum. The residue was purified by chromatography on silica gel, eluting with 20% ethyl acetate in petroleum ether to afford the title compound (60 mg).
¹H NMR (400 MHz, CDCl₃) δ 9.02 (s, 1H), 8.30 (dd, 1H), 7.47-7.43 (m, 1H), 7.38 (s, 1H), 7.33 (dd, 1H), 6.96-6.71 (s, 1H). MS (M+H)=213

Step F: Preparation of 5-chloro-2-[[2-[5-(difluoromethyl)-3-isoxazolyl]-3-pyridinyl]oxy]pyrimidine To a solution of 2-[5-(difluoromethyl)-3-isoxazolyl]-3-pyridinol (i.e. the product of Step E) (240 mg, 0.926 mmol) in dimethylformamide (5.0 mL) was added 5-chloro-2-methylsulfonyl-pyrimidine (i.e. 5-chloro-2-(methylsulfonyl)-pyrimidine) (260 mg, 1.39 mmol) and cesium carbonate (636 mg, 1.80 mmol) at 0° C., and the reaction was allowed to warm to room temperature over 45 minutes. The reaction was partitioned between water and ethyl acetate, the organic phase was collected and further washed with saturated aqueous sodium chloride. The organic phase was dried with magnesium sulfate, and concentrated under vacuum. The residue was purified by preparative high pressure liquid chromatography (silica gel column), eluting with 20% ethyl acetate in petroleum ether to afford the title compound, a compound of the present invention, as a solid (120 mg).
¹H NMR (400 MHz, CDCl₃) δ 8.72-8.65 (m, 1H), 8.45 (s, 2H), 7.70 (dd, 1H), 7.53 (dd, 1H), 7.25 (br s, 1H), 6.92-6.58 (m, 1H). MS (M+H)=325

Step G: Preparation of 5-chloro-2-[[2-[5-(difluoromethyl)-3-isoxazolyl]-1-oxido-3-pyridinyl]oxy] pyrimidine To a solution of 5-chloro-2-[[2-[5-(difluoromethyl)-3-isoxazolyl]-3-pyridinyl]oxy]-pyrimidine (i.e. the product of Step F) (20 mg, 0.060 mmol) in anhydrous dichloromethane (3 mL) was added m-chloroperoxybenzoic acid (11 mg, 0.087 mmol) at 0° C., and the reaction was allowed to warm to room temperature for 48 hours. The reaction was partitioned between water and ethyl acetate, the organic phase was collected and further washed with a saturated solution of sodium bicarbonate. The organic phase was dried with magnesium sulfate, and concentrated under vacuum. The residue was washed with pentane and diethyl ether to afford the title compound, a compound of the present invention, as a solid (10 mg).
¹H NMR (400 MHz, CDCl₃) δ 8.47 (s, 2H), 8.34-8.30 (m, 1H), 7.46-7.26 (m, 3H), 6.89-6.61 (m, 1H). MS (M+H)=341

Example 2

Preparation of 2-[[2-(4-bromo-1H-pyrazol-1-yl)-3-pyridinyl]oxy]-5-chloro-pyrimidine (Compound 1)

Step A: Preparation of 2-(4-bromo-1H-pyrazol-1-yl)-3-methoxypyridine

To a solution of 2-bromo-3-methoxy-pyridine (2.0 g, 10.63 mmol) and 4-bromopyrazole (1.72 g, 11.70 mmol) in dimethylsulfoxide (20 mL) was added K₂CO₃ (4.42 g, 31.91 mmol), CuI (0.40 g, 2.12 mmol) and L-proline (0.62 g, 5.31 mmol). The mixture was stirred at 100° C. for 36 h under a nitrogen atmosphere. The reaction mixture was cooled, diluted with water (200 mL) and extracted with ethyl acetate (3×200 mL). The combined organic phases were washed with water and saturated aqueous sodium chloride, dried over Na₂SO₄, filtered and concentrated under reduced pressure. The resulting residue was purified by medium pressure liquid chromatography on silica gel eluted with 0 to 25% ethyl acetate in hexanes to yield the title compound (900 mg) as a pale brown solid.
¹H NMR (400 MHz, CDCl₃) δ 8.26 (s, 1H), 8.18 (d, 1H), 7.75 (s, 1H), 7.43 (dd, 1H), 7.32-7.29 (m, 1H), 3.96 (s, 3H). mp=84-87° C.

Step B: Preparation of 2-(4-bromo-1H-pyrazol-1-yl)-3-pyridinol

To a solution of 2-(4-bromo-1H-pyrazol-1-yl)-3-methoxypyridine (i.e. the product of Step A) (0.9 g, 3.54 mmol) in dichloromethane (10 mL) was added borontribromide (1.77 g, 7.08 mmol) at 0° C. The reaction mixture was stirred at ambient temperature for 15 h. The reaction mixture was then poured into ice-cold saturated NaHCO₃ solution and extracted with dichloromethane (3×50 mL). The combined organic phases were washed with saturated aqueous sodium chloride and dried over anhydrous Na₂SO₄ and concentrated under reduced pressure. The crude reaction product was washed with pentane and diethyl ether to afford the title compound (0.45 g) as an off white solid.

$^1$H NMR (400 MHz, CDCl$_3$) δ 11.08 (brs, 1H), 8.65 (s, 1H), 7.93 (dd, 1H), 7.69 (s, 1H), 7.40 (dd, 1H), 7.17-7.14 (m, 1H). mp=91-93° C.

Step C: Preparation of 2-[[2-(4-bromo-1H-pyrazol-1-yl)-3-pyridinyl]oxy]-5-chloro-pyrimidine To a solution of 2-(4-bromo-1H-pyrazol-1-yl)pyridine-3-ol (i.e. the product of Step B) (0.35 g, 1.45 mmol) in N,N-dimethylformamide (5.0 mL) was added 2,5-dichloropyrimidine (0.22 g, 1.45 mmol) and potassium carbonate (0.60 g, 4.37 mmol). The reaction mixture was stirred at 70° C. for 3 h. The reaction mixture was cooled, poured in water (50 mL) and extracted with ethyl acetate (3×50 mL). The combined organic phases were washed with water followed by saturated aqueous sodium chloride, dried over anhydrous Na$_2$SO$_4$ and concentrated under reduced pressure. The resulting crude product was purified by medium pressure liquid chromatography on silica gel eluted with 0 to 35% ethyl acetate in hexanes to yield the title compound, a compound of the present invention, (140 mg) as an off white solid.

$^1$H NMR (400 MHz, CDCl$_3$) δ 8.50-8.40 (m, 4H), 7.72 (d, J=8.0, 1H), 7.40 (brs, 2H). mp=129-131° C.

Example 3

Preparation of 5-chloro-2-[(5-chloro[2,3'-bipyridin]-2'-yl)oxy]pyrimidine (Compound 12)

Step A: Preparation of 5-chloro-2'-methoxy-2,3'-bipyridine

To a nitrogen degassed solution of 3-methoxy-2-(tributylstannyl)-pyridine (0.34 g, 0.86 mmol) in toluene (5.0 mL) was added 2,5-dichloropyridine (0.14 g, 0.95 mmol), copper bromide (0.009 g, 0.06 mmol, 0.7 equiv), and tetrakis(triphenylphosphine)palladium (0.050 g, 0.043 mmol). The solution was heated to 100° C. under a nitrogen atmosphere for 18 h. The reaction mixture was cooled to ambient tamerature and the solvent was removed under vacuum. The reustlting residue was purified by silica gel chromatography eluting with an ethyl acetate in hexanes (0 to 100%). Subsequent acid/base extraction removed further impurities to afford the title compound (0.056 g).

$^1$H NMR (500 MHz, CDCl$_3$) δ 8.71-8.76 (m, 1H), 8.36-8.40 (m, 1H), 7.84-7.90 (m, 1H), 7.76 (m, 1H), 7.30-7.38 (m, 2H), 3.88-3.91 (m, 3H).

Step B: Preparation of 5'-chloro-[2,2'-bipyridin]-3-ol

To a solution of 5-chloro-2'-methoxy-2,3'-bipyridine (i.e. the product obtained in Step A, 0.056 g, 0.25 mmol) in dichloromethane (3 mL) was added 0.25 mL of a 1 M boron tribromide solution in dichloromethane. The reaction mixture was stirred at ambient temperature for 18 h. The reaction mixture was partitioned with saturated sodium bicarbonate and the organic phase was dried with MgSO$_4$ and concentrated under vacuum. The resulting residue was dissolved in ethyl acetate and extracted into 1 N sodium hydroxide. The aqueous phase was separated and neutralized with 1 N aqueous hydrochloric acid, and the precipitate was extracted into ethyl acetate. The organic phase was dried with MgSO$_4$ and concentrated under vacuum to afford the title compound (0.030 g).

$^1$H NMR (500 MHz, CDCl$_3$) δ 13.19-13.40 (bs, 1H), 8.58 (dd, 1H), 8.50 (dd, 1H) 8.21 (dd, 1H), 7.89 (dd, 1H), 7.34 (dd, 1H), 7.23-7.28 (m, 1H).

Step C: Preparation of 5-chloro-2-[(5-chloro[2,3'-bipyridin]-2'-yl)oxy]pyrimidine To a solution of 5'-chloro-[2,2'-bipyridin]-3-ol (i.e. the product of Step B, 0.030 g, 0.14 mmol) in N,N-dimethylformamide (2.0 mL) was added 5-chloro-2-(methylsulfonyl)-pyrimidine (0.042 g, 0.22 mmol) and potassium carbonate (0.021 g, 0.15 mmol) and the reaction stirred at ambient temperature for 18 h. The solvent was removed from the reaction mixture under vacuum and the resulting residue purified by silica gel chromatography eluting with a methanol in dichloromethane (0 to 30%), followed by a ethyl acetate in hexanes (0 to 30%) to provide the title compound, a compound of the invention (0.0085 g).

$^1$H NMR (500 MHz, CDCl$_3$) δ 8.63-8.69 (m, 1H), 8.42 (s, 2H), 8.31-8.36 (m, 1H) 8.03-8.11 (m, 1H), 7.69-7.74 (m, 1H), 7.65 (s, 1H), 7.44-7.49 (m, 1H); MS [M+H]$^+$=319

By the procedures described herein together with methods known in the art, the following compounds of Tables 1 to 778 can be prepared. The following abbreviations are used in the Tables which follow: t means tertiary, s means secondary, n means normal, i means iso, c means cyclo, Me means methyl, Et means ethyl, Pr means propyl, Bu means butyl, i-Pr means isopropyl, Bu means butyl, c-Pr cyclopropyl, c-Bu means cyclobutyl, Ph means phenyl, OMe means methoxy, OEt means ethoxy, SMe means methylthio, SEt means ethylthio, NHMe methylamino, —CN means cyano, Py means pyridinyl, —NO$_2$ means nitro, tzl meand triazol, pzl means pyrazol, izl means imidazole, odzl means oxadiazol, tdzl means thiadiazol and SO$_2$Me means methylsulfonyl.

TABLE 1

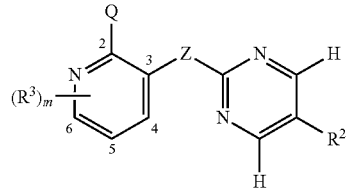

R$^2$ = Cl; Z = O; and R$^3$ = H (m = 0);

| Q | Q | Q |
|---|---|---|
| 3-CF$_3$-1H-pyrazol-1-yl | 3-Me-1H-pyrazol-1-yl | 3-F-1H-pyrazol-1-yl |
| 3-Br-1H-pyrazol-1-yl | 4-CF$_3$-1H-pyrazol-1-yl | 4-Me-1H-pyrazol-1-yl |
| 4-F-1H-pyrazol-1-yl | 4-Br-1H-pyrazol-1-yl | 5-CF$_3$-1H-pyrazol-1-yl |

TABLE 1-continued

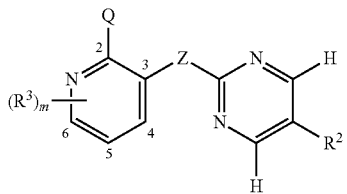

$R^2$ = Cl; Z = O; and $R^3$ = H (m = 0);

| Q | Q | Q |
|---|---|---|
| 5-Me-1H-pyrazol-1-yl | 5-F-1H-pyrazol-1-yl | 5-Br-1H-pyrazol-1-yl |
| 3-CHF$_2$-1H-pyrazol-1-yl | 3-Et-1H-pyrazol-1-yl | 3-Cl-1H-pyrazol-1-yl |
| 3-I-1H-pyrazol-1-yl | 4-CHF$_2$-1H-pyrazol-1-yl | 4-Et-1H-pyrazol-1-yl |
| 4-Cl-1H-pyrazol-1-yl | 4-I-1H-pyrazol-1-yl | 5-CHF$_2$-1H-pyrazol-1-yl |
| 5-Et-1H-pyrazol-1-yl | 5-Cl-1H-pyrazol-1-yl | 3-I-1H-pyrazol-1-yl |
| 3-OMe-1H-pyrazol-1-yl | 3-CN-1H-pyrazol-1-yl | 3-OCF$_3$-1H-pyrazol-1-yl |
| 3-OCHF$_2$-1H-pyrazol-1-yl | 4-OMe-1H-pyrazol-1-yl | 4-CN-1H-pyrazol-1-yl |
| 4-OCF$_3$-1H-pyrazol-1-yl | 4-OCHF$_2$-1H-pyrazol-1-yl | 5-OCF$_3$-1H-pyrazol-1-yl |
| 5-CN-1H-pyrazol-1-yl | 5-OCF$_3$-1H-pyrazol-1-yl | 5-OCHF$_2$-1H-pyrazol-1-yl |
| 3-C(=O)MeO-1H-pyrazol-1-yl | 3-Ph-1H-pyrazol-1-yl | 3,5-di-Me-1H-pyrazol-1-yl |
| 3,5-di-F-1H-pyrazol-1-yl | 4-C(=O)MeO-1H-pyrazol-1-yl | 4-Ph-1H-pyrazol-1-yl |
| 3,5-di-CF$_3$-1H-pyrazol-1-yl | 3,5-di-Cl-1H-pyrazol-1-yl | 5-C(=O)MeO-1H-pyrazol-1-yl |
| 5-Ph-1H-pyrazol-1-yl | 3,5-di-CHF$_2$-1H-pyrazol-1-yl | 3,5-di-Br-1H-pyrazol-1-yl |
| 3-CF$_3$-5-Me-1H-pyrazol-1-yl | 3,4-di-Me-1H-pyrazol-1-yl | 3,4-di-CF$_3$-1H-pyrazol-1-yl |
| 3,4-di-Br-1H-pyrazol-1-yl | 3,4-di-Cl-1H-pyrazol-1-yl | 1H-pyrazol-1-yl |
| 3-Me-1H-[1,2,4]triazol-1-yl | 3-CF$_3$-1H-[1,2,4]triazol-1-yl | 3-CHF$_2$-1H-[1,2,4]triazol-1-yl |
| 3-F-1H-[1,2,4]triazol-1-yl | 3-Cl-1H-[1,2,4]triazol-1-yl | 3-Br-1H-[1,2,4]triazol-1-yl |
| 3,5-di-Cl-1H-[1,2,4]triazol-1-yl | 3,5-di-Br-1H-[1,2,4]triazol-1-yl | 3-Ph-1H-[1,2,4]triazol-1-yl |
| 1H-[1,2,4]triazol-1-yl | 4-Me-2H-[1,2,3]triazol-2-yl | 4-CF$_3$-2H-[1,2,3]triazol-2-yl |
| 4-CHF$_2$-2H-[1,2,3]triazol-2-yl | 4-F-2H-[1,2,3]triazol-2-yl | 4-Cl-2H-[1,2,3]triazol-2-yl |
| 4-Br-2H-[1,2,3]triazol-2-yl | 4-Ph-2H-[1,2,3]triazol-2-yl | 4,5-di-Me-2H-[1,2,3]triazol-2-yl |
| 4,5-di-CF$_3$-2H-[1,2,3]triazol-2-yl | 4,5-di-Cl-2H-[1,2,3]triazol-2-yl | 4,5-di-Br-2H-[1,2,3]triazol-2-yl |
| 2H-[1,2,3]triazol-2-yl | 4-Me-1H-[1,2,3]triazol-1-yl | 4-CF$_3$-1H-[1,2,3]triazol-1-yl |
| 4-CHF$_2$-1H-[1,2,3]triazol-1-yl | 4-F-1H-[1,2,3]triazol-1-yl | 4-Cl-1H-[1,2,3]triazol-1-yl |
| 4-Br-1H-[1,2,3]triazol-1-yl | 4-Ph-1H-[1,2,3]triazol-1-yl | 1H-[1,2,3]triazol-1-yl |
| 3-Me-1H-pyrrol-1-yl | 3-CF$_3$-1H-pyrrol-1-yl | 3-CHF$_2$-1H-pyrrol-1-yl |
| 3,4-di-Me-1H-pyrrol-1-yl | 2,4-di-Me-1H-pyrrol-1-yl | 3,4-di-CF$_3$-1H-pyrrol-1-yl |
| 2,4-di-CF$_3$-1H-pyrrol-1-yl | 3,4-di-Br-1H-pyrrol-1-yl | 3,4-di-Cl-1H-pyrrol-1-yl |
| 4-CHO-1H-pyrazol-1-yl | 4-CF$_2$CF$_3$-1H-pyrazol-1-yl | 4-OCF$_2$CF$_2$H-1H-pyrazol-1-yl |
| 4-CH$_2$CF$_3$-1H-pyrazol-1-yl | 4-OCH$_2$CF$_3$-1H-pyrazol-1-yl | 4-n-Pr-1H-pyrazol-1-yl |
| 4-i-Pr-1H-pyrazol-1-yl | 4-c-Pr-1H-pyrazol-1-yl | 4-Ethynyl-1H-pyrazol-1-yl |
| 4-Vinyl-1H-pyrazol-1-yl | 4-Allyl-1H-pyrazol-1-yl | 4-CH$_2$F-1H-pyrazol-1-yl |
| 4-SF$_5$-1H-pyrazol-1-yl | 4-OCH$_2$CCH-1H-pyrazol-1-yl | 4-SCF$_3$-1H-pyrazol-1-yl |
| 4-SCHF$_2$-1H-pyrazol-1-yl | 4-SOMe-1H-pyrazol-1-yl | 4-SO$_2$Me-1H-pyrazol-1-yl |
| 4-SO$_2$CF$_3$-1H-pyrazol-1-yl | 4-CH$_2$OCH$_3$-1H-pyrazol-1-yl | 4-OCH$_2$CHCH$_2$-1H-pyrazol-1-yl |
| 4-CH$_2$SCH$_3$-1H-pyrazol-1-yl | 4-CF$_3$-1H-imidazol-1-yl | 4-F-1H-imidazol-1-yl |
| 4-Cl-1H-imidazol-1-yl | 4-Br-1H-imidazol-1-yl | 4-I-1H-imidazol-1-yl |
| 4-Me-1H-imidazol-1-yl | 4-Et-1H-imidazol-1-yl | 4-CHF$_2$-1H-imidazol-1-yl |
| 4-CHO-1H-imidazol-1-yl | 4-CH$_2$CF$_3$-1H-imidazol-1-yl | 4-OCF$_3$-1H-imidazol-1-yl |
| Isoxazol-5-yl | 4-Me-isoxazol-5-yl | 5-CHO-isoxazol-3-yl |
| 3-F-isoxazol-5-yl | 4-Et-isoxazol-5-yl | 5-CN-isoxazol-3-yl |
| 3-Cl-isoxazol-5-yl | 4-CF$_3$-isoxazol-5-yl | 5-CH$_2$CN-isoxazol-3-yl |
| 3-Br-isoxazol-5-yl | 4-CHF$_2$-isoxazol-5-yl | 5-OMe-isoxazol-3-yl |
| 3-I-isoxazol-5-yl | 4-CHO-isoxazol-5-yl | 5-OCF$_3$-isoxazol-3-yl |
| 3-Me-isoxazol-5-yl | 4-CN-isoxazol-5-yl | 5-Ph-isoxazol-3-yl |
| 3-Et-isoxazol-5-yl | 4-OMe-isoxazol-5-yl | 4-F-isoxazol-3-yl |
| 3-CF$_3$-isoxazol-5-yl | 4-OCF$_3$-isoxazol-5-yl | 4-Cl-isoxazol-3-yl |
| 3-CHF$_2$-isoxazol-5-yl | 4-Ph-isoxazol-5-yl | 4-Br-isoxazol-3-yl |
| 3-CHO-isoxazol-5-yl | isoxazol-3-yl | 4-I-isoxazol-3-yl |
| 3-CN-isoxazol-5-yl | 5-F-isoxazol-3-yl | 4-Me-isoxazol-3-yl |
| 3-OMe-isoxazol-5-yl | 5-Cl-isoxazol-3-yl | 4-Et-isoxazol-3-yl |
| 3-OCF$_3$-isoxazol-5-yl | 5-Br-isoxazol-3-yl | 4-CF$_3$-isoxazol-3-yl |
| 3-Ph-isoxazol-5-yl | 5-I-isoxazol-3-yl | 4-CHF$_2$-isoxazol-3-yl |
| 4-F-isoxazol-5-yl | 5-Me-isoxazol-3-yl | 4-CHO-isoxazol-3-yl |
| 4-Cl-isoxazol-5-3/1 | 5-Et-isoxazol-3-yl | 4-CN-isoxazol-3-yl |
| 4-Br-isoxazol-5-yl | 5-CF$_3$-isoxazol-3-yl | 4-OMe-isoxazol-3-yl |
| 4-I-isoxazol-5-yl | 5-CHF$_2$-isoxazol-3-yl | 4-OCF$_3$-isoxazol-3-yl |
| 4-Ph-isoxazol-3-yl | 5-CHF$_2$-isothiazol-3-yl | 5-Br-isoxazol-4-yl |
| Isothiazol-5-yl | 5-CHO-isothiazol-3-yl | 5-I-isoxazol-4-yl |
| 3-F-isothiazol-5-yl | 5-CN-isothiazol-3-yl | 5-Me-isoxazol-4-yl |
| 3-Cl-isothiazol-5-yl | 5-CH$_2$CN-isothiazol-3-yl | 5-Et-isoxazol-4-yl |
| 3-Br-isothiazol-5-yl | 5-OMe-isothiazol-3-yl | 5-CF$_3$-isoxazol-4-yl |
| 3-I-isothiazol-5-yl | 5-OCF$_3$-isothiazol-3-yl | 5-CHF$_2$-isoxazol-4-yl |
| 3-Me-isothiazol-5-yl | 5-Ph-isothiazol-3-yl | 5-CHO-isoxazol-4-yl |
| 3-Et-isothiazol-5-yl | 4-F-isothiazol-3-yl | 5-CN-isoxazol-4-yl |
| 3-CF$_3$-isothiazol-5-yl | 4-Cl-isothiazol-3-yl | 5-OMe-isoxazol-4-yl |

TABLE 1-continued

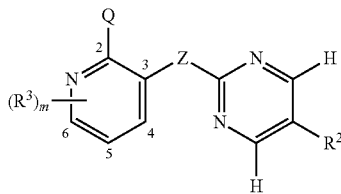

$R^2 = Cl; Z = O;$ and $R^3 = H$ (m = 0);

| Q | Q | Q |
|---|---|---|
| 3-CHF$_2$-isothiazol-5-yl | 4-Br-isothiazol-3-yl | 5-OCF$_3$-isoxazol-4-yl |
| 3-CHO-isothiazol-5-yl | 4-I-isothiazol-3-yl | 5-Ph-isoxazol-4-yl |
| 3-CN-isothiazol-5-yl | 4-Me-isothiazol-3-yl | Isothiazol-4-yl |
| 3-OMe-isothiazol-5-yl | 4-Et-isothiazol-3-yl | 3-F-isothiazol-4-yl |
| 3-OCF$_3$-isothiazol-5-yl | 4-CF$_3$-isothiazol-3-yl | 3-Cl-isothiazol-4-yl |
| 3-Ph-isothiazol-5-yl | 4-CHF$_2$-isothiazol-3-yl | 3-Br-isothiazol-4-yl |
| 4-F-isothiazol-5-yl | 4-CHO-isothiazol-3-yl | 3-I-isothiazol-4-yl |
| 4-Cl-isothiazol-5-yl | 4-CN-isothiazol-3-yl | 3-Me-isothiazol-4-yl |
| 4-Br-isothiazol-5-yl | 4-OMe-isothiazol-3-yl | 3-Et-isothiazol-4-yl |
| 4-I-isothiazol-5-yl | 4-OCF$_3$-isothiazol-3-yl | 3-CF$_3$-isothiazol-4-yl |
| 4-Me-isothiazol-5-yl | 4-Ph-isothiazol-3-yl | 3-CHF$_2$-isothiazol-4-yl |
| 4-Et-isothiazol-5-yl | Isoxazol-4-yl | 3-CHO-isothiazol-4-yl |
| 4-CF$_3$-isothiazol-5-yl | 3-F-isoxazol-4-yl | 3-CN-isothiazol-4-yl |
| 4-CHF$_2$-isothiazol-5-yl | 3-Cl-isoxazol-4-yl | 3-OMe-isothiazol-4-yl |
| 4-CHO-isothiazol-5-yl | 3-Br-isoxazol-4-yl | 3-OCF$_3$-isothiazol-4-yl |
| 4-CN-isothiazol-5-yl | 3-I-isoxazol-4-yl | 3-Ph-isothiazol-4-yl |
| 4-OMe-isothiazol-5-yl | 3-Me-isoxazol-4-yl | 5-F-isothiazol-4-yl |
| 4-OCF$_3$-isothiazol-5-yl | 3-Et-isoxazol-4-yl | 5-Cl-isothiazol-4-yl |
| 4-Ph-isothiazol-5-yl | 3-CF$_3$-isoxazol-4-yl | 5-Br-isothiazol-4-yl |
| Isothiazol-3-yl | 3-CHF$_2$-isoxazol-4-yl | 5-I-isothiazol-4-yl |
| 5-F-isothiazol-3-yl | 3-CHO-isoxazol-4-yl | 5-Me-isothiazol-4-yl |
| 5-Cl-isothiazol-3-yl | 3-CN-isoxazol-4-yl | 5-Et-isothiazol-4-yl |
| 5-Br-isothiazol-3-yl | 3-OMe-isoxazol-4-yl | 5-CF$_3$-isothiazol-4-yl |
| 5-I-isothiazol-3-yl | 3-OCF$_3$-isoxazol-4-yl | 5-CHF$_2$-isothiazol-4-yl |
| 5-Me-isothiazol-3-yl | 3-Ph-isoxazol-4-yl | 5-CHO-isothiazol-4-yl |
| 5-Et-isothiazol-3-yl | 5-F-isoxazol-4-yl | 5-CN-isothiazol-4-yl |
| 5-CF$_3$-isothiazol-3-yl | 5-Cl-isoxazol-4-yl | 5-OMe-isothiazol-4-yl |
| 5-OCF$_3$-isothiazol-4-yl | 5-Et-thiazol-2-yl | 4-Me-oxazol-5-yl |
| 5-Ph-isothiazol-4-yl | 5-CF$_3$-thiazol-2-yl | 4-CF$_3$-oxazol-5-yl |
| oxazol-2-yl | 5-CHF$_2$-thiazol-2-yl | 4-CHF$_2$-oxazol-5-yl |
| 5-F-oxazol-2-yl | 5-CHO-thiazol-2-yl | 4-CN-oxazol-5-yl |
| 5-Cl-oxazol-2-yl | 5-CN-thiazol-2-yl | 4-OMe-oxazol-5-yl |
| 5-Br-oxazol-2-yl | 5-CH$_2$CN-thiazol-2-yl | 4-OCF$_3$-oxazol-5-yl |
| 5-I-oxazol-2-yl | 5-OMe-thiazol-2-yl | 4-Ph-oxazol-5-yl |
| 5-Me-oxazol-2-yl | 5-OCF$_3$-thiazol-2-yl | Thiazol-5-yl |
| 5-Et-oxazol-2-yl | 5-Ph-thiazol-2-yl | 2-F-thiazol-5-yl |
| 5-CF$_3$-oxazol-2-yl | 4-F-thiazol-2-yl | 2-Cl-thiazol-5-yl |
| 5-CHF$_2$-oxazol-2-yl | 4-Cl-thiazol-2-yl | 2-Br-thiazol-5-yl |
| 5-CHO-oxazol-2-yl | 4-Br-thiazol-2-yl | 2-Me-thiazol-5-yl |
| 5-CN-oxazol-2-yl | 4-I-thiazol-2-yl | 2-CF$_3$-thiazol-5-yl |
| 5-CH$_2$CN-oxazol-2-yl | 4-Me-thiazol-2-yl | 2-CHF$_2$-thiazol-5-yl |
| 5-OMe-oxazol-2-yl | 4-Et-thiazol-2-yl | 2-CN-thiazol-5-yl |
| 5-OCF$_3$-oxazol-2-yl | 4-CF$_3$-thiazol-2-yl | 2-OMe-thiazol-5-yl |
| 5-Ph-oxazol-2-yl | 4-CHF$_2$-thiazol-2-yl | 2-OCF$_3$-thiazol-5-yl |
| 4-F-oxazol-2-yl | 4-CHO-thiazol-2-yl | 2-Ph-thiazol-5-yl |
| 4-Cl-oxazol-2-yl | 4-CN-thiazol-2-yl | 4-F-thiazol-5-yl |
| 4-Br-oxazol-2-yl | 4-OMe-thiazol-2-yl | 4-Cl-thiazol-5-yl |
| 4-I-oxazol-2-yl | 4-OCF$_3$-thiazol-2-yl | 4-Br-thiazol-5-yl |
| 4-Me-oxazol-2-yl | 4-Ph-thiazol-2-yl | 4-Me-thiazol-5-yl |
| 4-Et-oxazol-2-yl | Oxazol-5-yl | 4-CF$_3$-thiazol-5-yl |
| 4-CF$_3$-oxazol-2-yl | 2-F-oxazol-5-yl | 4-CHF$_2$-thiazol-5-yl |
| 4-CHF$_2$-oxazol-2-yl | 2-Cl-oxazol-5-yl | 4-CN-thiazol-5-yl |
| 4-CHO-oxazol-2-yl | 2-Br-oxazol-5-yl | 4-OMe-thiazol-5-yl |
| 4-CN-oxazol-2-yl | 2-Me-oxazol-5-yl | 4-OCF$_3$-thiazol-5-yl |
| 4-OMe-oxazol-2-yl | 2-CF$_3$-oxazol-5-yl | 4-Ph-thiazol-5-yl |
| 4-OCF$_3$-oxazol-2-yl | 2-CHF$_2$-oxazol-5-yl | Oxazol-4-yl |
| 4-Ph-oxazol-2-yl | 2-CN-oxazol-5-yl | 2-F-oxazol-4-yl |
| Thiazol-2-yl | 2-OMe-oxazol-5-yl | 2-Cl-oxazol-4-yl |
| 5-F-thiazol-2-yl | 2-OCF$_3$-oxazol-5-yl | 2-Br-oxazol-4-yl |
| 5-Cl-thiazol-2-yl | 2-Ph-oxazol-5-yl | 2-Me-oxazol-4-yl |
| 5-Br-thiazol-2-yl | 4-F-oxazol-5-yl | 2-CF$_3$-oxazol-4-yl |
| 5-I-thiazol-2-yl | 4-Cl-oxazol-5-yl | 2-CHF$_2$-oxazol-4-yl |
| 5-Me-thiazol-2-yl | 4-Br-oxazol-5-yl | 2-CN-oxazol-4-yl |
| 2-OMe-oxazol-4-yl | 4-F-1-Me-1H-izl-2-yl | 5-CF$_3$-1-Me-1H-izl-4-yl |
| 2-OCF$_3$-oxazol-4-yl | 4-Cl-1-Me-1H-izl-2-yl | 5-CHF$_2$-1-Me-1H-izl-4-yl |
| 2-Ph-oxazol-4-yl | 4-Br-1-Me-1H-izl-2-yl | 5-CN-1-Me-1H-izl-4-yl |

TABLE 1-continued

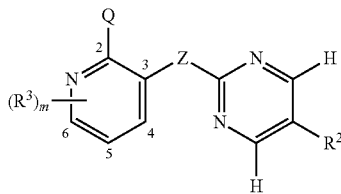

$R^2 = Cl$; $Z = O$; and $R^3 = H$ (m = 0);

| Q | Q | Q |
|---|---|---|
| 5-F-oxazol-4-yl | 1,4-di-Me-1H-izl-2-yl | 5-OMe-1-Me-1H-izl-4-yl |
| 5-Cl-oxazol-4-yl | 4-CF$_3$-1-Me-1H-izl-2-yl | 5-OCF$_3$-1-Me-1H-izl-4-yl |
| 5-Br-oxazol-4-yl | 4-CHF$_2$-1-Me-1H-izl-2-yl | 5-Ph-1-Me-1H-izl-4-yl |
| 5-Me-oxazol-4-yl | 4-CN-1-Me-1H-izl-2-yl | 1H-izl-5-yl |
| 5-CF$_3$-oxazol-4-yl | 4-OMe-1-Me-1H-izl-2-yl | 1-Me-1H-izl-5-yl |
| 5-CHF$_2$-oxazol-4-yl | 4-OCF$_3$-1-Me-1H-izl-2-yl | 2-F-1-Me-1H-izl-5-yl |
| 5-CN-oxazol-4-yl | 4-Ph-1-Me-1H-izl-2-yl | 2-Cl-1-Me-1H-izl-5-yl |
| 5-OMe-oxazol-4-yl | 5-F-1-Me-1H-izl-2-yl | 2-Br-1-Me-1H-izl-5-yl |
| 5-OCF$_3$-oxazol-4-yl | 5-Cl-1-Me-1H-izl-2-yl | 1,2-di-Me-1H-izl-5-yl |
| 5-Ph-oxazol-4-yl | 5-Br-1-Me-1H-izl-2-yl | 2-CF$_3$-1-Me-1H-izl-5-yl |
| Thiazol-4-yl | 1,5-di-Me-1H-izl-2-yl | 2-CHF$_2$-1-Me-1H-izl-5-yl |
| 2-F-thiazol-4-yl | 5-CF$_3$-1-Me-1H-izl-2-yl | 2-CN-1-Me-1H-izl-5-yl |
| 2-Cl-thiazol-4-yl | 5-CHF$_2$-1-Me-1H-izl-2-yl | 2-OMe-1-Me-1H-izl-5-yl |
| 2-Br-thiazol-4-yl | 5-CN-1-Me-1H-izl-2-yl | 2-OCF$_3$-1-Me-1H-izl-5-yl |
| 2-Me-thiazol-4-yl | 5-OMe-1-Me-1H-izl-2-yl | 2-Ph-1-Me-1H-izl-5-yl |
| 2-CF$_3$-thiazol-4-yl | 5-OCF$_3$-1-Me-1H-izl-2-yl | 4-F-1-Me-1H-izl-5-yl |
| 2-CHF$_2$-thiazol-4-yl | 5-Ph-1-Me-1H-izl-2-yl | 4-Cl-1-Me-1H-izl-5-yl |
| 2-CN-thiazol-4-yl | 1H-izl-4-yl | 4-Br-1-Me-1H-izl-5-yl |
| 2-OMe-thiazol-4-yl | 1-Me-1H-izl-4-yl | 1,4-di-Me-1H-izl-5-yl |
| 2-OCF$_3$-thiazol-4-yl | 2-F-1-Me-1H-izl-4-yl | 4-CF$_3$-1-Me-1H-izl-5-yl |
| 2-Ph-thiazol-4-yl | 2-Cl-1-Me-1H-izl-4-yl | 4-CHF$_2$-1-Me-1H-izl-5-yl |
| 5-F-thiazol-4-yl | 2-Br-1-Me-1H-izl-4-yl | 4-CN-1-Me-1H-izl-5-yl |
| 5-Cl-thiazol-4-yl | 1,2-di-Me-1H-izl-4-yl | 4-OMe-1-Me-1H-izl-5-yl |
| 5-Br-thiazol-4-yl | 2-CF$_3$-1-Me-1H-izl-4-yl | 4-OCF$_3$-1-Me-1H-izl-5-yl |
| 5-Me-thiazol-4-yl | 2-CHF$_2$-1-Me-1H-izl-4-yl | 4-Ph-1-Me-1H-izl-5-yl |
| 5-CF$_3$-thiazol-4-yl | 2-CN-1-Me-1H-izl-4-yl | 1H-pzl-3-yl |
| 5-CHF$_2$-thiazol-4-yl | 2-OMe-1-Me-1H-izl-4-yl | 1-Me-1H-pzl-3-yl |
| 5-CN-thiazol-4-yl | 2-OCF$_3$-1-Me-1H-izl-4-yl | 4-F-1-Me-1H-pzl-3-yl |
| 5-OMe-thiazol-4-yl | 2-Ph-1-Me-1H-izl-4-yl | 4-Cl-1-Me-1H-pzl-3-yl |
| 5-OCF$_3$-thiazol-4-yl | 5-F-1-Me-1H-izl-4-yl | 4-Br-1-Me-1H-pzl-3-yl |
| 5-Ph-thiazol-4-yl | 5-Cl-1-Me-1H-izl-4-yl | 1,4-di-Me-1H-pzl-3-yl |
| 1H-izl-2-yl | 5-Br-1-Me-1H-izl-4-yl | 4-CF$_3$-1-Me-1H-pzl-3-yl |
| 1-Me-1H-izl-2-yl | 1,5-di-Me-1H-izl-4-yl | 4-CHF$_2$-1-Me-1H-pzl-3-yl |
| 4-CN-1-Me-1H-pzl-3-yl | 1H-pzl-5-yl | 2-CHF$_2$[1,3,4]odzl-5-yl |
| 4-OMe-1-Me-1H-pzl-3-yl | 1-Me-1H-pzl-5-yl | 2-CN-[1,3,4]odzl-5-yl |
| 4-OCF$_3$-1-Me-1H-pzl-3-yl | 3-F-1-Me-1H-pzl-5-yl | 2-OMe-[1,3,4]odzl-5-yl |
| 4-Ph-1-Me-1H-pzl-3-yl | 3-Cl-1-Me-1H-pzl-5-yl | 2-OCF$_3$[1,3,4]odzl-5-yl |
| 5-F-1-Me-1H-pzl-3-yl | 3-Br-1-Me-1H-pzl-5-yl | [1,3,4]tdzl-2-yl |
| 5-Cl-1-Me-1H-pzl-3-yl | 1,3-di-Me-1H-pzl-5-yl | 2-F-[1,3,4]tdzl-5-yl |
| 5-Br-1-Me-1H-pzl-3-yl | 3-CF$_3$-1-Me-1H-pzl-5-yl | 2-Cl-[1,3,4]tdzl-5-yl |
| 1,5-di-Me-1H-pzl-3-yl | 3-CHF$_2$-1-Me-1H-pzl-5-yl | 2-Br-[1,3,4]tdzl-5-yl |
| 5-CF$_3$-1-Me-1H-pzl-3-yl | 3-CN-1-Me-1H-pzl-5-yl | 2-Me-[1,3,4]tdzl-5-yl |
| 5-CHF$_2$-1-Me-1H-pzl-3-yl | 3-OMe-1-Me-1H-pzl-5-yl | 2-CF$_3$-[1,3,4]tdzl-5-yl |
| 5-CN-1-Me-1H-pzl-3-yl | 3-OCF$_3$-1-Me-1H-pzl-5-yl | 2-CHF$_2$-[1,3,4]tdzl-5-yl |
| 5-OMe-1-Me-1H-pzl-3-yl | 3-Ph-1-Me-1H-pzl-5-yl | 2-CN-[1,3,4]tdzl-5-yl |
| 5-OCF$_3$-1-Me-1H-pzl-3-yl | 4-F-1-Me-1H-pzl-5-yl | 2-OMe-[1,3,4]tdzl-5-yl |
| 5-Ph-1-Me-1H-pzl-3-yl | 4-Cl-1-Me-1H-pzl-5-yl | 2-OCF$_3$-[1,3,4]tdzl-5-yl |
| 1H-pzl-4-yl | 4-Br-1-Me-1H-pzl-5-yl | 4H-[1,2,4]tzl-3-yl |
| 1-Me-1H-pzl-4-yl | 1,4-di-Me-1H-pzl-5-yl | 4-Me-4H-[1,2,4]tzl-3-yl |
| 3-F-1-Me-1H-pzl-4-yl | 4-CF$_3$-1-Me-1H-pzl-5-yl | 3-F-4-Me-4H-[1,2,4]tzl-5-yl |
| 3-Cl-1-Me-1H-pzl-4-yl | 4-CHF$_2$-1-Me-1H-pzl-5-yl | 3-Cl-4-Me-4H-[1,2,4]tzl-5-yl |
| 3-Br-1-Me-1H-pzl-4-yl | 4-CN-1-Me-1H-pzl-5-yl | 3-Br-4-Me-4H-[1,2,4]tzl-5-yl |
| 1,3-di-Me-1H-pzl-4-yl | 4-OMe-1-Me-1H-pzl-5-yl | 3,4-di-Me-4H-[1,2,4]tzl-5-yl |
| 3-CF$_3$-1-Me-1H-pzl-4-yl | 4-OCF$_3$-1-Me-1H-pzl-5-yl | 3-CF$_3$-4-Me-4H-[1,2,4]tzl-5-yl |
| 3-CHF$_2$-1-Me-1H-pzl-4-yl | 4-Ph-1-Me-1H-pzl-5-yl | 3-CHF$_2$-4-Me-4-[1,2,4]tzl-5yl |
| 3-CN-1-Me-1H-pzl-4-yl | Thiophene-2-yl | 3-CN-4-Me-4H-[1,2,4]tzl-5-yl |
| 3-OMe-1-Me-1H-pzl-4-yl | Thiophene-3-yl | 3-OMe-4-Me-4H-[1,2,4]tzl-5-yl |
| 3-OCF$_3$-1-Me-1H-pzl-4-yl | Furan-2-yl | 3-OCF$_3$-4-Me-4H-[1,2,4]tzl-5yl |
| 3-Ph-1-Me-1H-pzl-4-yl | Furan-3-yl | 3-Ph-4-Me-4H-[1,2,4]tzl-5-yl |
| 5-F-1-Me-1H-pzl-4-yl | 1H-pyrrol-2-yl | 1H-[1,2,4]tzl-3-yl |
| 5-Cl-1-Me-1H-pzl-4-yl | 1-Me-1H-pyrrol-2-yl | 1-Me-1H-[1,2,4]tzl-3-yl |
| 5-Br-1-Me-1H-pzl-4-yl | 1H-pyrrol-3-yl | 5-F-1-Me-1H-[1,2,4]tzl-3-yl |
| 1,5-di-Me-1H-pzl-4-yl | 1-Me-1H-pyrrol-3-yl | 5-Cl-1-Me-1H-[1,2,4]tzl-3-yl |
| 5-CF$_3$-1-Me-1H-pzl-4-yl | [1,3,4]odzl-2-yl | 5-Br-1-Me-1H-[1,2,4]tzl-3-yl |
| 5-CHF$_2$-1-Me-1H-pzl-4-yl | 2-F[1,3,4]odzl-5-yl | 1,5-di-Me-1H-[1,2,4]tzl-3-yl |
| 5-CN-1-Me-1H-pzl-4-yl | 2-Cl1[,3,4]odzl-5-yl | 5-CF$_3$-1-Me-1H-[1,2,4]tzl-3-yl |

TABLE 1-continued

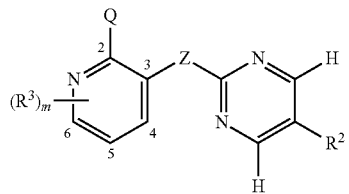

$R^2$ = Cl; Z = O; and $R^3$ = H (m = 0);

| Q | Q | Q |
|---|---|---|
| 5-OMe-1-Me-1H-pzl-4-yl | 2-Br[1,3,4]odzl-5-yl | 5-CHF$_2$-1-Me-1H-[1,2,4]tzl-3yl |
| 5-OCF$_3$-1-Me-1H-pzl-4-yl | 2-Me[1,3,4]odzl-5-yl | 5-CN-1-Me-1H-[1,2,4]tzl-3-yl |
| 5-Ph-1-Me-1H-pzl-4-yl | 2-CF$_3$[1,3,4]odzl-5-yl | 5-OMe-1-Me-1H-[1,2,4]tzl-3-yl |
| 5-OCF$_3$-1-Me-1H-[1,2,4]tzl-3yl | [1,2,4]tdzl-5-yl | 5-Br[1,2,3]odzl-4-yl |
| 5-Ph-1-Me-1H-[1,2,4]tzl-3-yl | 3-F-[1,2,4]tdzl-5-yl | 5-Me-[1,2,3]odzl-4-yl |
| 1H-[1,2,4]tzl-5-yl | 3-Cl-[1,2,4]tdzl-5-yl | 5-CF$_3$-[1,2,3]odzl-4-yl |
| 1-Me-1H-[1,2,4]tzl-5-yl | 3-Br-[1,2,4]tdzl-5-yl | 5-CHF$_2$-[1,2,3]odzl-4-yl |
| 3-F-1-Me-1H-[1,2,4]tzl-5-yl | 3-Me-[1,2,4]tdzl-5-yl | 5-CN-[1,2,3]odzl-4-yl |
| 3-Cl-1-Me-1H-[1,2,4]tzl-5-yl | 3-CF$_3$-[1,2,4]tdzl-5-yl | 5-OMe-[1,2,3]odzl-4-yl |
| 3-Br-1-Me-1H-[1,2,4]tzl-5-yl | 3-CHF$_2$-[1,2,4]tdzl-5-yl | 5-OCF$_3$-[1,2,3]odzl-4-yl |
| 1,3-di-Me-1H-[1,2,4]tzl-5-yl | 3-CN-[1,2,4]tdzl-5-yl | 5-Ph-[1,2,3]odzl-4-yl |
| 3-CF$_3$-1-Me-1H-[1,2,4]tzl-5-yl | 3-OMe-[1,2,4]tdzl-5-yl | [1,2,3]tdzl-5-yl |
| 3-CHF$_2$-1-Me-1H-[1,2,4]tzl-5yl | 3-OCF$_3$-[1,2,4]tdzl-5-yl | 4-F-[1,2,3]tdzl-5-yl |
| 3-CN-1-Me-1H-[1,2,4]tzl-5-yl | 3-Ph-[1,2,4]tdzl-5-yl | 4-Cl-[1,2,3]tdzl-5-yl |
| 3-OMe-1-Me-1H-[1,2,4]tzl-5-yl | [1,2,4]tdzl-3-yl | 4-Br-[1,2,3]tdzl-5-yl |
| 3-OCF$_3$-1-Me-1H-[1,2,4]tzl-5yl | 5-F-[1,2,4]tdzl-3-yl | 4-Me-[1,2,3]tdzl-5-yl |
| 3-Ph-1-Me-1H--[1,2,4]tzl-5-yl | 5-Cl-[1,2,4]tdzl-3-yl | 4-CF$_3$-[1,2,3]tdzl-5-yl |
| [1,2,4]odzl-5-yl | 5-Br-[1,2,4]tdzl-3-yl | 4-CHF$_2$-[1,2,3]tdzl-5-yl |
| 3-F-[1,2,4]odzl-5-yl | 5-Me-[1,2,4]tdzl-3-yl | 4-CN-[1,2,3]tdzl-5-yl |
| 3-Cl-[1,2,4]odzl-5-yl | 5-CF$_3$-[1,2,4]tdzl-3-yl | 4-OMe-[1,2,3]tdzl-5-yl |
| 3-Br-[1,2,4]odzl-5-yl | 5-CHF$_2$-[1,2,4]tdzl-3-yl | 4-OCF$_3$-[1,2,3]tdzl-5-yl |
| 3-Me-[1,2,4]odzl-5-yl | 5-CN-[1,2,4]tdzl-3-yl | 4-Ph-[1,2,3]tdzl-5-yl |
| 3-CF$_3$-[1,2,4]odzl-5-yl | 5-OMe-[1,2,4]tdzl-3-yl | [1,2,3]tdzl-4-yl |
| 3-CHF$_2$-[1,2,4]lodzl-5-yl | 5-OCF$_3$-[1,2,4]tdzl-3-yl | 5-F-[1,2,3]tdzl-4-yl |
| 3-CN-[1,2,4]odzl-5-yl | 5-Ph-[1,2,4]tdzl-3-yl | 5-Cl-[1,2,3]tdzl-4-yl |
| 3-OMe-[1,2,4]odzl-5-yl | [1,2,3]odzl-5-yl | 5-Br-[1,2,3]tdzl-4-yl |
| 3-OCF$_3$-[1,2,4]lodzl-5-yl | 4-F-[1,2,3]odzl-5-yl | 5-Me-[1,2,3]tdzl-4-yl |
| 3-Ph-[1,2,4]odzl-5-yl | 4-Cl-[1,2,3]odzl-5-yl | 5-CF$_3$[1,2,3]tdzl-4-yl |
| [1,2,4]odzl-3-yl | 4-Br-[1,2,3]odzl-5-yl | 5-CHF$_2$-[1,2,3]tdzl-4-yl |
| 5-F-[1,2,4]odzl-3-yl | 4-Me-[1,2,3]odzl-5-yl | 5-CN-[1,2,3]tdzl-4-yl |
| 5-Cl-[1,2,4]odzl-3-yl | 4-CF$_3$-[1,2,3]odzl-5-yl | 5-OMe-[1,2,3]tdzl-4-yl |
| 5-Br-[1,2,4]odzl-3-yl | 4-CHF$_2$-[1,2,3]odzl-5-yl | 5-OCF$_3$-[1,2,3]tdzl-4-yl |
| 5-Me-[1,2,4]odzl-3-yl | 4-CN-[1,2,3]odzl-5-yl | 5-Ph-[1,2,3]tdzl-4-yl |
| 5-CF$_3$-[1,2,4]odzl-3-yl | 4-OMe-[1,2,3]odzl-5-yl | 3H-[1,2,4]tzl-3-yl |
| 5-CHF$_2$-[1,2,4]odzl-3-yl | 4-OCF$_3$-[1,2,3]odzl-5-yl | 5-F-3H-[1,2,4]tzl-3-yl |
| 5-CN-[1,2,4]odzl-3-yl | 4-Ph-[1,2,3]odzl-5-yl | 5-Cl-3H-[1,2,4]tzl-3-yl |
| 5-OMe-[1,2,4]odzl-3-yl | [1,2,3]odzl-4-yl | 5-Br-3H-[1,2,4]tzl-3-yl |
| 5-OCF$_3$-[1,2,4]odzl-3-yl | 5-F-[1,2,3]odzl-4-yl | 5-Me-3H-[1,2,4]tzl-3-yl |
| 5-Ph-[1,2,4]odzl-3-yl | 5-Cl-[1,2,3]odzl-4-yl | 5-CF$_3$-3H-[1,2,4]tzl-3-yl |
| 5-CHF$_2$-3H-[1,2,4]tzl-3-yl | 4-OCF$_3$-1H-[1,2,3]tzl-5-yl | 3-I-pyridin-2-yl |
| 5-CN-3H-[1,2,4]tzl-3-yl | 4-Ph-1H-[1,2,3]tzl-5-yl | 3-Me-pyridin-2-yl |
| 5-OMe-3H-[1,2,4]tzl-3-yl | 5-F-pyridin-2-yl | 3-Et-pyridin-2-yl |
| 5-OCF$_3$-3H-[1,2,4]tzl-3-yl | 5-Cl-pyridin-2-yl | 3-CF$_3$-pyridin-2-yl |
| 5-Ph-3H-[1,2,4]tzl-3-yl | 5-Br-pyridin-2-yl | 3-CHF$_2$-pyridin-2-yl |
| 1H-[1,2,3]tzl-4-yl | 5-I-pyridin-2-yl | 3-CHO-pyridin-2-yl |
| 5-F-1H-[1,2,3]tzl-4-yl | 5-Me-pyridin-2-yl | 3-CN-pyridin-2-yl |
| 5-Cl-1H-[1,2,3]tzl-4-yl | 5-Et-pyridin-2-yl | 3-OMe-pyridin-2-yl |
| 5-Br-1H-[1,2,3]tzl-4-yl | 5-CF$_3$-pyridin-2-yl | 3-OCF$_3$-pyridin-2-yl |
| 5-Me-1H-[1,2,3]tzl-4-yl | 5-CHF$_2$-pyridin-2-yl | 3-N(Me)$_2$-pyridin-2-yl |
| 5-CF$_3$-1H-[1,2,3]tzl-4-yl | 5-CHO-pyridin-2-yl | 3-Ph-pyridin-2-yl |
| 5-CHF$_2$-1H-[1,2,3]tzl-4-yl | 5-CN-pyridin-2-yl | 5,6-di-Cl-pyridin-2-yl |
| 5-CN-1H-[1,2,3]tzl-4-yl | 5-OMe-pyridin-2-yl | 6-F-pyridin-3-yl |
| 5-OMe-1H-[1,2,3]tzl-4-yl | 5-OCF$_3$-pyridin-2-yl | 6-Cl-pyridin-3-yl |
| 5-OCF$_3$-1H-[1,2,3]tzl-4-yl | 5-N(Me)$_2$-pyridin-2-yl | 6-Br-pyridin-3-yl |
| 5-Ph-1H-[1,2,3]tzl-4-yl | 5-Ph-pyridin-2-yl | 6-I-pyridin-3-yl |
| 2H-[1,2,3]tzl-4-yl | 3,5-di-Cl-pyridin-2-yl | 6-Me-pyridin-3-yl |
| 4-F-2H-[1,2,3]tzl-5-yl | 3-Me-5-Cl-pyridin-2-yl | 6-Et-pyridin-3-yl |
| 4-Cl-2H-[1,2,3]tzl-5-yl | 3-CN-5-Cl-pyridin-2-yl | 6-CF$_3$-pyridin-3-yl |
| 4-Br-2H-[1,2,3]tzl-5-yl | 6-F-pyridin-2-yl | 6-CHF$_2$-pyridin-3-yl |
| 4-Me-2H-[1,2,3]tzl-5-yl | 6-Cl-pyridin-2-yl | 6-CHO-pyridin-3-yl |
| 4-CF$_3$-2H-[1,2,3]tzl-5-yl | 6-Br-pyridin-2-yl | 6-CN-pyridin-3-yl |
| 4-CHF$_2$-2H-[1,2,3]tzl-5-yl | 6-I-pyridin-2-yl | 6-OMe-pyridin-3-yl |
| 4-CN-2H-[1,2,3]tzl-5-yl | 6-Me-pyridin-2-yl | 6-OCF$_3$-pyridin-3-yl |
| 4-OMe-2H-[1,2,3]tzl-5-yl | 6-Et-pyridin-2-yl | 6-N(Me)$_2$-pyridin-3-yl |
| 4-OCF$_3$-2H-[1,2,3]tzl-5-yl | 6-CF$_3$-pyridin-2-yl | 6-Ph-pyridin-3-yl |
| 4-Ph-2H-[1,2,3]tzl-5-yl | 6-CHF$_2$-pyridin-2-yl | 4,6-di-Cl-pyridin-3-yl |

TABLE 1-continued

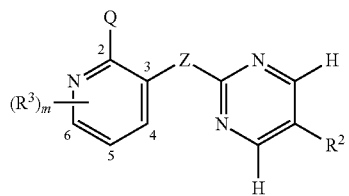

R² = Cl; Z = O; and R³ = H (m = 0);

| Q | Q | Q |
|---|---|---|
| 1H-[1,2,3]tzl-5-yl | 6-CHO-pyridin-2-yl | 4-CN-6-Cl-pyridin-3-yl |
| 4-F-1H-[1,2,3]tzl-5-yl | 6-CN-pyridin-2-yl | 3-F-pyridin-4-yl |
| 4-Cl-1H-[1,2,3]tzl-5-yl | 6-OMe-pyridin-2-yl | 3-Cl-pyridin-4-yl |
| 4-Br-1H-[1,2,3]tzl-5-yl | 6-OCF₃-pyridin-2-yl | 3-Br-pyridin-4-yl |
| 4-Me-1H-[1,2,3]tzl-5-yl | 6-N(Me)₂-pyridin-2-yl | 3-I-pyridin-4-yl |
| 4-CF₃-1H-[1,2,3]tzl-5-yl | 6-Ph-pyridin-2-yl | 3-Me-pyridin-4-yl |
| 4-CHF₂-1H-[1,2,3]tzl-5-yl | 3-F-pyridin-2-yl | 3-Et-pyridin-4-yl |
| 4-CN-1H-[1,2,3]tzl-5-yl | 3-Cl-pyridin-2-yl | 3-CF₃-pyridin-4-yl |
| 4-OMe-1H-[1,2,3]tzl-5-yl | 3-Br-pyridin-2-yl | 3-CHF₂-pyridin-4-yl |
| 3-CHO-pyridin-4-yl | 6-OCF₃-pyridazin-4-yl | 2-Br-pyrimidin-5-yl |
| 3-CN-pyridin-4-yl | 6-N(Me)₂-pyridazin-4-yl | 2-I-pyrimidin-5-yl |
| 3-OMe-pyridin-4-yl | 6-Ph-pyridazin-4-yl | 2-Me-pyrimidin-5-yl |
| 3-OCF₃-pyridin-4-yl | 4-Cl-pyridazin-4-yl | 2-Et-pyrimidin-5-yl |
| 3-N(Me)₂-pyridin-4-yl | 4-CN-pyridazin-4-yl | 2-CF₃-pyrimidin-5-yl |
| 3-Ph-pyridin-4-yl | 5-F-pyridazin-4-yl | 2-CHF₂-pyrimidin-5-yl |
| 3,5-di-Me-pyridin-4-yl | 5-Cl-pyridazin-2-yl | 2-CHO-pyrimidin-5-yl |
| 3,5-di-Cl-pyridin-4-yl | 5-Br-pyridazin-2-yl | 2-CN-pyrimidin-5-yl |
| 6-F-pyridazin-3-yl | 5-I-pyridazin-2-yl | 2-OMe-pyrimidin-5-yl |
| 6-Cl-pyridazin-3-yl | 5-Me-pyridazin-2-yl | 2-OCF₃-pyrimidin-5-yl |
| 6-Br-pyridazin-3-yl | 5-Et-pyridazin-2-yl | 2-N(Me)₂-pyrimidin-5-yl |
| 6-I-pyridazin-3-yl | 5-CF₃-pyridazin-2-yl | 2-Ph-pyrimidin-5-yl |
| 6-Me-pyridazin-3-yl | 5-CHF₂-pyridazin-2-yl | 3-Cl-pyrazin-2-yl |
| 6-Et-pyridazin-3-yl | 5-CHO-pyridazin-2-yl | 3-CN-pyrazin-2-yl |
| 6-CF₃-pyridazin-3-yl | 5-CN-pyridazin-2-yl | 3-OMe-pyrazin-2-yl |
| 6-CHF₂-pyridazin-3-yl | 5-OMe-pyridazin-2-yl | 3-Cl-[1,2,4]triazin-6-yl |
| 6-CHO-pyridazin-3-yl | 5-OCF₃-pyridazin-2-yl | 3-CN-[1,2,4]triazin-6-yl |
| 6-CN-pyridazin-3-yl | 5-N(Me)₂-pyridazin-2-yl | 3-OMe-[1,2,4]triazin-6-yl |
| 6-OMe-pyridazin-3-yl | 5-Ph-pyridazin-2-yl | 3-CF₃-[1,2,4]triazin-6-yl |
| 6-OCF₃-pyridazin-3-yl | 5-F-pyrimidin-4-yl | 6-Cl-[1,2,4]triazin-5-yl |
| 6-N(Me)₂-pyridazin-3-yl | 5-Cl-pyrimidin-4-yl | 6-Me-[1,2,4]triazin-5-yl |
| 6-Ph-pyridazin-3-yl | 5-Br-pyrimidin-4-yl | 6-OMe-[1,2,4]triazin-5-yl |
| 4-Cl-pyridazin-3-yl | 5-I-pyrimidin-4-yl | 6-CN-[1,2,4]triazin-5-yl |
| 4-CN-pyridazin-3-yl | 5-Me-pyrimidin-4-yl | 6-Cl-[1,2,4]triazin-3-yl |
| 6-F-pyridazin-4-yl | 5-Et-pyrimidin-4-yl | 6-Me-[1,2,4]triazin-3-yl |
| 6-Cl-pyridazin-4-yl | 5-CF₃-pyrimidin-4-yl | 6-OMe-[1,2,4]triazin-3-yl |
| 6-Br-pyridazin-4-yl | 5-CHF₂-pyrimidin-4-yl | 6-CN-[1,2,4]triazin-3-yl |
| 6-I-pyridazin-4-yl | 5-CHO-pyrimidin-4-yl | 4-Cl-[1,3,5]triazin-2-yl |
| 6-Me-pyridazin-4-yl | 5-CN-pyrimidin-4-yl | 2-Me-pyrimidin-5-yl |
| 6-Et-pyridazin-4-yl | 5-OMe-pyrimidin-4-yl | 4-OMe-1H-imidazol-1-yl |
| 6-CF₃-pyridazin-4-yl | 5-OCF₃-pyrimidin-4-yl | |
| 6-CHF₂-pyridazin-4-yl | 5-N(Me)₂-pyrimidin-4-yl | |
| 6-CHO-pyridazin-4-yl | 5-Ph-pyrimidin-4-yl | |
| 6-CN-pyridazin-4-yl | 2-F-pyrimidin-5-yl | |
| 6-OMe-pyridazin-4-yl | 2-Cl-pyrimidin-5-yl | |

The present disclosure also includes Tables 2 through 778. Each Table is constructed in the same manner as Table 1 above, except that the row heading in Table 1 (i.e. "R²=Cl; Z=O; and R³=H (m=0).") is replaced with the respective row heading shown below.

| Table | Header Row |
|---|---|
| 2 | R² = F, Z = O, R³ = H (m = 0) |
| 3 | R² = F, Z = O, R³ = 4-F |
| 4 | R² = F, Z = O, R³ = 4-Cl |
| 5 | R² = F, Z = O, R³ = 4-Br |
| 6 | R² = F, Z = O, R³ = 4-I |
| 7 | R² = F, Z = O, R³ = 4-CN |
| 8 | R² = F, Z = O, R³ = 4-NO₂ |
| 9 | R² = F, Z = O, R³ = 4-OMe |
| 10 | R² = F, Z = O, R³ = 4-OCF₃ |
| 11 | R² = F, Z = O, R³ = 4-CF₃ |
| 12 | R² = F, Z = O, R³ = 4-CHF₂ |
| 13 | R² = F, Z = O, R³ = 4-CH₂F |
| 14 | R² = F, Z = O, R³ = 4-CHO |
| 15 | R² = F, Z = O, R³ = 4-Me |
| 16 | R² = F, Z = O, R³ = 4-Et |
| 17 | R² = F, Z = O, R³ = 4-Ethynyl |
| 18 | R² = F, Z = O, R³ = 4-Ethenyl |
| 19 | R² = F, Z = O, R³ = 4-SO₂Me |
| 20 | R² = F, Z = O, R³ = 4-OAc |
| 21 | R² = F, Z = O, R³ = 4-c-Pr |
| 22 | R² = F, Z = O, R³ = 4-i-Pr |
| 23 | R² = F, Z = O, R³ = 4-Ph |

-continued

| Table | Header Row |
|---|---|
| 24 | $R^2$ = F, Z = O, $R^3$ = 5-F |
| 25 | $R^2$ = F, Z = O, $R^3$ = 5-Cl |
| 26 | $R^2$ = F, Z = O, $R^3$ = 5-Br |
| 27 | $R^2$ = F, Z = O, $R^3$ = 5-I |
| 28 | $R^2$ = F, Z = O, $R^3$ = 5-CN |
| 29 | $R^2$ = F, Z = O, $R^3$ = 5-NO$_2$ |
| 30 | $R^2$ = F, Z = O, $R^3$ = 5-OMe |
| 31 | $R^2$ = F, Z = O, $R^3$ = 5-OCF$_3$ |
| 32 | $R^2$ = F, Z = O, $R^3$ = 5-CF$_3$ |
| 33 | $R^2$ = F, Z = O, $R^3$ = 5-CHF$_2$ |
| 34 | $R^2$ = F, Z = O, $R^3$ = 5-CH$_2$F |
| 35 | $R^2$ = F, Z = O, $R^3$ = 5-CHO |
| 36 | $R^2$ = F, Z = O, $R^3$ = 5-Me |
| 37 | $R^2$ = F, Z = O, $R^3$ = 5-Et |
| 38 | $R^2$ = F, Z = O, $R^3$ = 5-Ethynyl |
| 39 | $R^2$ = F, Z = O, $R^3$ = 5-Ethenyl |
| 40 | $R^2$ = F, Z = O, $R^3$ = 5-SO$_2$Me |
| 41 | $R^2$ = F, Z = O, $R^3$ = 5-OAc |
| 42 | $R^2$ = F, Z = O, $R^3$ = 5-c-Pr |
| 43 | $R^2$ = F, Z = O, $R^3$ = 5-i-Pr |
| 44 | $R^2$ = F, Z = O, $R^3$ = 5-Ph |
| 45 | $R^2$ = F, Z = O, $R^3$ = 6-F |
| 46 | $R^2$ = F, Z = O, $R^3$ = 6-Cl |
| 47 | $R^2$ = F, Z = O, $R^3$ = 6-Br |
| 48 | $R^2$ = F, Z = O, $R^3$ = 6-I |
| 49 | $R^2$ = F, Z = O, $R^3$ = 6-CN |
| 50 | $R^2$ = F, Z = O, $R^3$ = 6-NO$_2$ |
| 51 | $R^2$ = F, Z = O, $R^3$ = 6-OMe |
| 52 | $R^2$ = F, Z = O, $R^3$ = 6-OCF$_3$ |
| 53 | $R^2$ = F, Z = O, $R^3$ = 6-CF$_3$ |
| 54 | $R^2$ = F, Z = O, $R^3$ = 6-CHF$_2$ |
| 55 | $R^2$ = F, Z = O, $R^3$ = 6-CH$_2$F |
| 56 | $R^2$ = F, Z = O, $R^3$ = 6-CHO |
| 57 | $R^2$ = F, Z = O, $R^3$ = 6-Me |
| 58 | $R^2$ = F, Z = O, $R^3$ = 6-Et |
| 59 | $R^2$ = F, Z = O, $R^3$ = 6-Ethynyl |
| 60 | $R^2$ = F, Z = O, $R^3$ = 6-Ethenyl |
| 61 | $R^2$ = F, Z = O, $R^3$ = 6-SO$_2$Me |
| 62 | $R^2$ = F, Z = O, $R^3$ = 6-OAc |
| 63 | $R^2$ = F, Z = O, $R^3$ = 6-c-Pr |
| 64 | $R^2$ = F, Z = O, $R^3$ = 6-i-Pr |
| 65 | $R^2$ = F, Z = O, $R^3$ = 6-Ph |
| 66 | $R^2$ = F, Z = O, $R^3$ = 4,5-di-F |
| 67 | $R^2$ = F, Z = O, $R^3$ = 4,5-di-Cl |
| 68 | $R^2$ = F, Z = O, $R^3$ = 4,5-di-Br |
| 69 | $R^2$ = F, Z = O, $R^3$ = 4,5-di-CN |
| 70 | $R^2$ = F, Z = O, $R^3$ = 4,5-di-Me |
| 71 | $R^2$ = F, Z = O, $R^3$ = 4,5-di-OMe |
| 72 | $R^2$ = F, Z = O, $R^3$ = 4,5-di-CF$_3$ |
| 73 | $R^2$ = Br, Z = O, $R^3$ = 4-F |
| 74 | $R^2$ = Br, Z = O, $R^3$ = 4-Cl |
| 75 | $R^2$ = Br, Z = O, $R^3$ = 4-Br |
| 76 | $R^2$ = Br, Z = O, $R^3$ = 4-I |
| 77 | $R^2$ = Br, Z = O, $R^3$ = 4-CN |
| 78 | $R^2$ = Br, Z = O, $R^3$ = 4-NO$_2$ |
| 79 | $R^2$ = Br, Z = O, $R^3$ = 4-OMe |
| 80 | $R^2$ = Br, Z = O, $R^3$ = 4-OCF$_3$ |
| 81 | $R^2$ = Br, Z = O, $R^3$ = 4-CF$_3$ |
| 82 | $R^2$ = Br, Z = O, $R^3$ = 4-CHF$_2$ |
| 83 | $R^2$ = Br, Z = O, $R^3$ = 4-CH$_2$F |
| 84 | $R^2$ = Br, Z = O, $R^3$ = 4-CHO |
| 85 | $R^2$ = Br, Z = O, $R^3$ = 4-Me |
| 86 | $R^2$ = Br, Z = O, $R^3$ = 4-Et |
| 87 | $R^2$ = Br, Z = O, $R^3$ = 4-Ethynyl |
| 88 | $R^2$ = Br, Z = O, $R^3$ = 4-Ethenyl |
| 89 | $R^2$ = Br, Z = O, $R^3$ = 4-SO$_2$Me |
| 90 | $R^2$ = Br, Z = O, $R^3$ = 4-OAc |
| 91 | $R^2$ = Br, Z = O, $R^3$ = 4-c-Pr |
| 92 | $R^2$ = Br, Z = O, $R^3$ = 4-i-Pr |
| 93 | $R^2$ = Br, Z = O, $R^3$ = 4-Ph |
| 94 | $R^2$ = Br, Z = O, $R^3$ = 5-F |
| 95 | $R^2$ = Br, Z = O, $R^3$ = 5-Cl |
| 96 | $R^2$ = Br, Z = O, $R^3$ = 5-Br |
| 97 | $R^2$ = Br, Z = O, $R^3$ = 5-I |
| 98 | $R^2$ = Br, Z = O, $R^3$ = 5-CN |
| 99 | $R^2$ = Br, Z = O, $R^3$ = 5-NO$_2$ |
| 100 | $R^2$ = Br, Z = O, $R^3$ = 5-OMe |
| 101 | $R^2$ = Br, Z = O, $R^3$ = 5-OCF$_3$ |
| 102 | $R^2$ = Br, Z = O, $R^3$ = 5-CF$_3$ |
| 103 | $R^2$ = Br, Z = O, $R^3$ = 5-CHF$_2$ |
| 104 | $R^2$ = Br, Z = O, $R^3$ = 5-CH$_2$F |
| 105 | $R^2$ = Br, Z = O, $R^3$ = 5-CHO |
| 106 | $R^2$ = Br, Z = O, $R^3$ = 5-Me |
| 107 | $R^2$ = Br, Z = O, $R^3$ = 5-Et |
| 108 | $R^2$ = Br, Z = O, $R^3$ = 5-Ethynyl |
| 109 | $R^2$ = Br, Z = O, $R^3$ = 5-Ethenyl |
| 110 | $R^2$ = Br, Z = O, $R^3$ = 5-SO$_2$Me |
| 111 | $R^2$ = Br, Z = O, $R^3$ = 5-OAc |
| 112 | $R^2$ = Br, Z = O, $R^3$ = 5-c-Pr |
| 113 | $R^2$ = Br, Z = O, $R^3$ = 5-i-Pr |
| 114 | $R^2$ = Br, Z = O, $R^3$ = 5-Ph |
| 115 | $R^2$ = Br, Z = O, $R^3$ = 6-F |
| 116 | $R^2$ = Br, Z = O, $R^3$ = 6-Cl |
| 117 | $R^2$ = Br, Z = O, $R^3$ = 6-Br |
| 118 | $R^2$ = Br, Z = O, $R^3$ = 6-I |
| 119 | $R^2$ = Br, Z = O, $R^3$ = 6-CN |
| 120 | $R^2$ = Br, Z = O, $R^3$ = 6-NO$_2$ |
| 121 | $R^2$ = Br, Z = O, $R^3$ = 6-OMe |
| 122 | $R^2$ = Br, Z = O, $R^3$ = 6-OCF$_3$ |
| 123 | $R^2$ = Br, Z = O, $R^3$ = 6-CF$_3$ |
| 124 | $R^2$ = Br, Z = O, $R^3$ = 6-CHF$_2$ |
| 125 | $R^2$ = Br, Z = O, $R^3$ = 6-CH$_2$F |
| 126 | $R^2$ = Br, Z = O, $R^3$ = 6-CHO |
| 127 | $R^2$ = Br, Z = O, $R^3$ = 6-Me |
| 128 | $R^2$ = Br, Z = O, $R^3$ = 6-Et |
| 129 | $R^2$ = Br, Z = O, $R^3$ = 6-Ethynyl |
| 130 | $R^2$ = Br, Z = O, $R^3$ = 6-Ethenyl |
| 131 | $R^2$ = Br, Z = O, $R^3$ = 6-SO$_2$Me |
| 132 | $R^2$ = Br, Z = O, $R^3$ = 6-OAc |
| 133 | $R^2$ = Br, Z = O, $R^3$ = 6-c-Pr |
| 134 | $R^2$ = Br, Z = O, $R^3$ = 6-i-Pr |
| 135 | $R^2$ = Br, Z = O, $R^3$ = 6-Ph |
| 136 | $R^2$ = Br, Z = O, $R^3$ = 4,5-di-F |
| 137 | $R^2$ = Br, Z = O, $R^3$ = 4,5-di-Cl |
| 138 | $R^2$ = Br, Z = O, $R^3$ = 4,5-di-Br |
| 139 | $R^2$ = Br, Z = O, $R^3$ = 4,5-di-CN |
| 140 | $R^2$ = Br, Z = O, $R^3$ = 4,5-di-OMe |
| 141 | $R^2$ = Br, Z = O, $R^3$ = 4,5-di-CF$_3$ |
| 142 | $R^2$ = Cl, Z = O, $R^3$ = H (m = 0) |
| 143 | $R^2$ = Cl, Z = O, $R^3$ = 4-F |
| 144 | $R^2$ = Cl, Z = O, $R^3$ = 4-Cl |
| 145 | $R^2$ = Cl, Z = O, $R^3$ = 4-Br |
| 146 | $R^2$ = Cl, Z = O, $R^3$ = 4-I |
| 147 | $R^2$ = Cl, Z = O, $R^3$ = 4-CN |
| 148 | $R^2$ = Cl, Z = O, $R^3$ = 4-NO$_2$ |
| 149 | $R^2$ = Cl, Z = O, $R^3$ = 4-OMe |
| 150 | $R^2$ = Cl, Z = O, $R^3$ = 4-OCF$_3$ |
| 151 | $R^2$ = Cl, Z = O, $R^3$ = 4-CF$_3$ |
| 152 | $R^2$ = Cl, Z = O, $R^3$ = 4-CHF$_2$ |
| 153 | $R^2$ = Cl, Z = O, $R^3$ = 4-CH$_2$F |
| 154 | $R^2$ = Cl, Z = O, $R^3$ = 4-CHO |
| 155 | $R^2$ = Cl, Z = O, $R^3$ = 4-Me |
| 156 | $R^2$ = Cl, Z = O, $R^3$ = 4-Et |
| 157 | $R^2$ = Cl, Z = O, $R^3$ = 4-Ethynyl |
| 158 | $R^2$ = Cl, Z = O, $R^3$ = 4-Ethenyl |
| 159 | $R^2$ = Cl, Z = O, $R^3$ = 4-SO$_2$Me |
| 160 | $R^2$ = Cl, Z = O, $R^3$ = 4-OAc |
| 161 | $R^2$ = Cl, Z = O, $R^3$ = 4-c-Pr |
| 162 | $R^2$ = Cl, Z = O, $R^3$ = 4-i-Pr |
| 163 | $R^2$ = Cl, Z = O, $R^3$ = 4-Ph |
| 164 | $R^2$ = Cl, Z = O, $R^3$ = 5-F |
| 165 | $R^2$ = Cl, Z = O, $R^3$ = 5-Cl |
| 166 | $R^2$ = Cl, Z = O, $R^3$ = 5-Br |
| 167 | $R^2$ = Cl, Z = O, $R^3$ = 5-I |
| 168 | $R^2$ = Cl, Z = O, $R^3$ = 5-CN |
| 169 | $R^2$ = Cl, Z = O, $R^3$ = 5-NO$_2$ |
| 170 | $R^2$ = Cl, Z = O, $R^3$ = 5-OMe |
| 171 | $R^2$ = Cl, Z = O, $R^3$ = 5-OCF$_3$ |
| 172 | $R^2$ = Cl, Z = O, $R^3$ = 5-CF$_3$ |
| 173 | $R^2$ = Cl, Z = O, $R^3$ = 5-CHF$_2$ |
| 174 | $R^2$ = Cl, Z = O, $R^3$ = 5-CH$_2$F |
| 175 | $R^2$ = Cl, Z = O, $R^3$ = 5-CHO |
| 176 | $R^2$ = Cl, Z = O, $R^3$ = 5-Me |
| 177 | $R^2$ = Cl, Z = O, $R^3$ = 5-Et |

| Table | Header Row |
|---|---|
| 178 | $R^2$ = Cl, Z = O, $R^3$ = 5-Ethynyl |
| 179 | $R^2$ = Cl, Z = O, $R^3$ = 5-Ethenyl |
| 180 | $R^2$ = Cl, Z = O, $R^3$ = 5-SO$_2$Me |
| 181 | $R^2$ = Cl, Z = O, $R^3$ = 5-OAc |
| 182 | $R^2$ = Cl, Z = O, $R^3$ = 5-c-Pr |
| 183 | $R^2$ = Cl, Z = O, $R^3$ = 5-i-Pr |
| 184 | $R^2$ = Cl, Z = O, $R^3$ = 5-Ph |
| 185 | $R^2$ = Cl, Z = O, $R^3$ = 6-F |
| 186 | $R^2$ = Cl, Z = O, $R^3$ = 6-Cl |
| 187 | $R^2$ = Cl, Z = O, $R^3$ = 6-Br |
| 188 | $R^2$ = Cl, Z = O, $R^3$ = 6-I |
| 189 | $R^2$ = Cl, Z = O, $R^3$ = 6-CN |
| 190 | $R^2$ = Cl, Z = O, $R^3$ = 6-NO$_2$ |
| 191 | $R^2$ = Cl, Z = O, $R^3$ = 6-OMe |
| 192 | $R^2$ = Cl, Z = O, $R^3$ = 6-OCF$_3$ |
| 193 | $R^2$ = Cl, Z = O, $R^3$ = 6-CF$_3$ |
| 194 | $R^2$ = Cl, Z = O, $R^3$ = 6-CHF$_2$ |
| 195 | $R^2$ = Cl, Z = O, $R^3$ = 6-CH$_2$F |
| 196 | $R^2$ = Cl, Z = O, $R^3$ = 6-CHO |
| 197 | $R^2$ = Cl, Z = O, $R^3$ = 6-Me |
| 198 | $R^2$ = Cl, Z = O, $R^3$ = 6-Et |
| 199 | $R^2$ = Cl, Z = O, $R^3$ = 6-Ethynyl |
| 200 | $R^2$ = Cl, Z = O, $R^3$ = 6-Ethenyl |
| 201 | $R^2$ = Cl, Z = O, $R^3$ = 6-SO$_2$Me |
| 202 | $R^2$ = Cl, Z = O, $R^3$ = 6-OAc |
| 203 | $R^2$ = Cl, Z = O, $R^3$ = 6-c-Pr |
| 204 | $R^2$ = Cl, Z = O, $R^3$ = 6-i-Pr |
| 205 | $R^2$ = Cl, Z = O, $R^3$ = 6-Ph |
| 206 | $R^2$ = Cl, Z = O, $R^3$ = 4,5-di-F |
| 207 | $R^2$ = Cl, Z = O, $R^3$ = 4,5-di-Cl |
| 208 | $R^2$ = Cl, Z = O, $R^3$ = 4,5-di-Br |
| 209 | $R^2$ = Cl, Z = O, $R^3$ = 4,5-di-CN |
| 210 | $R^2$ = Cl, Z = O, $R^3$ = 4,5-di-Me |
| 211 | $R^2$ = Cl, Z = O, $R^3$ = 4,5-di-OMe |
| 212 | $R^2$ = Cl, Z = O, $R^3$ = 4,5-di-CF$_3$ |
| 213 | $R^2$ = I, Z = O, $R^3$ = H (m = 0) |
| 214 | $R^2$ = I, Z = O, $R^3$ = 4-F |
| 215 | $R^2$ = I, Z = O, $R^3$ = 4-Cl |
| 216 | $R^2$ = I, Z = O, $R^3$ = 4-Br |
| 217 | $R^2$ = I, Z = O, $R^3$ = 4-I |
| 218 | $R^2$ = I, Z = O, $R^3$ = 4-CN |
| 219 | $R^2$ = I, Z = O, $R^3$ = 4-NO$_2$ |
| 220 | $R^2$ = I, Z = O, $R^3$ = 4-OMe |
| 221 | $R^2$ = I, Z = O, $R^3$ = 4-OCF$_3$ |
| 222 | $R^2$ = I, Z = O, $R^3$ = 4-CF$_3$ |
| 223 | $R^2$ = I, Z = O, $R^3$ = 4-CHF$_2$ |
| 224 | $R^2$ = I, Z = O, $R^3$ = 4-CH$_2$F |
| 225 | $R^2$ = I, Z = O, $R^3$ = 4-CHO |
| 226 | $R^2$ = I, Z = O, $R^3$ = 4-Me |
| 227 | $R^2$ = I, Z = O, $R^3$ = 4-Et |
| 228 | $R^2$ = I, Z = O, $R^3$ = 4-Ethynyl |
| 229 | $R^2$ = I, Z = O, $R^3$ = 4-Ethenyl |
| 230 | $R^2$ = I, Z = O, $R^3$ = 4-SO$_2$Me |
| 231 | $R^2$ = I, Z = O, $R^3$ = 4-OAc |
| 232 | $R^2$ = I, Z = O, $R^3$ = 4-c-Pr |
| 233 | $R^2$ = I, Z = O, $R^3$ = 4-i-Pr |
| 234 | $R^2$ = I, Z = O, $R^3$ = 4-Ph |
| 235 | $R^2$ = I, Z = O, $R^3$ = 5-F |
| 236 | $R^2$ = I, Z = O, $R^3$ = 5-Cl |
| 237 | $R^2$ = I, Z = O, $R^3$ = 5-Br |
| 238 | $R^2$ = I, Z = O, $R^3$ = 5-I |
| 239 | $R^2$ = I, Z = O, $R^3$ = 5-CN |
| 240 | $R^2$ = I, Z = O, $R^3$ = 5-NO$_2$ |
| 241 | $R^2$ = I, Z = O, $R^3$ = 5-OMe |
| 242 | $R^2$ = I, Z = O, $R^3$ = 5-OCF$_3$ |
| 243 | $R^2$ = I, Z = O, $R^3$ = 5-CF$_3$ |
| 244 | $R^2$ = I, Z = O, $R^3$ = 5-CHF$_2$ |
| 245 | $R^2$ = I, Z = O, $R^3$ = 5-CH$_2$F |
| 246 | $R^2$ = I, Z = O, $R^3$ = 5-CHO |
| 247 | $R^2$ = I, Z = O, $R^3$ = 5-Me |
| 248 | $R^2$ = I, Z = O, $R^3$ = 5-Et |
| 249 | $R^2$ = I, Z = O, $R^3$ = 5-Ethynyl |
| 250 | $R^2$ = I, Z = O, $R^3$ = 5-Ethenyl |
| 251 | $R^2$ = I, Z = O, $R^3$ = 5-SO$_2$Me |
| 252 | $R^2$ = I, Z = O, $R^3$ = 5-OAc |
| 253 | $R^2$ = I, Z = O, $R^3$ = 5-c-Pr |
| 254 | $R^2$ = I, Z = O, $R^3$ = 5-i-Pr |
| 255 | $R^2$ = I, Z = O, $R^3$ = 5-Ph |
| 256 | $R^2$ = I, Z = O, $R^3$ = 6-F |
| 257 | $R^2$ = I, Z = O, $R^3$ = 6-Cl |
| 258 | $R^2$ = I, Z = O, $R^3$ = 6-Br |
| 259 | $R^2$ = I, Z = O, $R^3$ = 6-I |
| 260 | $R^2$ = I, Z = O, $R^3$ = 6-CN |
| 261 | $R^2$ = I, Z = O, $R^3$ = 6-NO$_2$ |
| 262 | $R^2$ = I, Z = O, $R^3$ = 6-OMe |
| 263 | $R^2$ = I, Z = O, $R^3$ = 6-OCF$_3$ |
| 264 | $R^2$ = I, Z = O, $R^3$ = 6-CF$_3$ |
| 265 | $R^2$ = I, Z = O, $R^3$ = 6-CHF$_2$ |
| 266 | $R^2$ = I, Z = O, $R^3$ = 6-CH$_2$F |
| 267 | $R^2$ = I, Z = O, $R^3$ = 6-CHO |
| 268 | $R^2$ = I, Z = O, $R^3$ = 6-Me |
| 269 | $R^2$ = I, Z = O, $R^3$ = 6-Et |
| 270 | $R^2$ = I, Z = O, $R^3$ = 6-Ethynyl |
| 271 | $R^2$ = I, Z = O, $R^3$ = 6-Ethenyl |
| 272 | $R^2$ = I, Z = O, $R^3$ = 6-SO$_2$Me |
| 273 | $R^2$ = I, Z = O, $R^3$ = 6-OAc |
| 274 | $R^2$ = I, Z = O, $R^3$ = 6-c-Pr |
| 275 | $R^2$ = I, Z = O, $R^3$ = 6-i-Pr |
| 276 | $R^2$ = I, Z = O, $R^3$ = 6-Ph |
| 277 | $R^2$ = I, Z = O, $R^3$ = 4,5-di-F |
| 278 | $R^2$ = I, Z = O, $R^3$ = 4,5-di-Cl |
| 279 | $R^2$ = I, Z = O, $R^3$ = 4,5-di-Br |
| 280 | $R^2$ = I, Z = O, $R^3$ = 4,5-di-CN |
| 281 | $R^2$ = I, Z = O, $R^3$ = 4,5-di-Me |
| 282 | $R^2$ = I, Z = O, $R^3$ = 4,5-di-OMe |
| 283 | $R^2$ = I, Z = O, $R^3$ = 4,5-di-CF$_3$ |
| 284 | $R^2$ = Me, Z = O, $R^3$ = 4-F |
| 285 | $R^2$ = Me, Z = O, $R^3$ = 4-Cl |
| 286 | $R^2$ = Me, Z = O, $R^3$ = 4-Br |
| 287 | $R^2$ = Me, Z = O, $R^3$ = 4-I |
| 288 | $R^2$ = Me, Z = O, $R^3$ = 4-CN |
| 289 | $R^2$ = Me, Z = O, $R^3$ = 4-NO$_2$ |
| 290 | $R^2$ = Me, Z = O, $R^3$ = 4-OMe |
| 291 | $R^2$ = Me, Z = O, $R^3$ = 4-OCF$_3$ |
| 292 | $R^2$ = Me, Z = O, $R^3$ = 4-CF$_3$ |
| 293 | $R^2$ = Me, Z = O, $R^3$ = 4-CHF$_2$ |
| 294 | $R^2$ = Me, Z = O, $R^3$ = 4-CH$_2$F |
| 295 | $R^2$ = Me, Z = O, $R^3$ = 4-CHO |
| 296 | $R^2$ = Me, Z = O, $R^3$ = 4-Me |
| 297 | $R^2$ = Me, Z = O, $R^3$ = 4-Et |
| 298 | $R^2$ = Me, Z = O, $R^3$ = 4-Ethynyl |
| 299 | $R^2$ = Me, Z = O, $R^3$ = 4-Ethenyl |
| 300 | $R^2$ = Me, Z = O, $R^3$ = 4-SO$_2$Me |
| 301 | $R^2$ = Me, Z = O, $R^3$ = 4-OAc |
| 302 | $R^2$ = Me, Z = O, $R^3$ = 4-c-Pr |
| 303 | $R^2$ = Me, Z = O, $R^3$ = 4-i-Pr |
| 304 | $R^2$ = Me, Z = O, $R^3$ = 4-Ph |
| 305 | $R^2$ = Me, Z = O, $R^3$ = 5-F |
| 306 | $R^2$ = Me, Z = O, $R^3$ = 5-Cl |
| 307 | $R^2$ = Me, Z = O, $R^3$ = 5-Br |
| 308 | $R^2$ = Me, Z = O, $R^3$ = 5-I |
| 309 | $R^2$ = Me, Z = O, $R^3$ = 5-CN |
| 310 | $R^2$ = Me, Z = O, $R^3$ = 5-NO$_2$ |
| 311 | $R^2$ = Me, Z = O, $R^3$ = 5-OMe |
| 312 | $R^2$ = Me, Z = O, $R^3$ = 5-OCF$_3$ |
| 313 | $R^2$ = Me, Z = O, $R^3$ = 5-CF$_3$ |
| 314 | $R^2$ = Me, Z = O, $R^3$ = 5-CHF$_2$ |
| 315 | $R^2$ = Me, Z = O, $R^3$ = 5-CH$_2$F |
| 316 | $R^2$ = Me, Z = O, $R^3$ = 5-CHO |
| 317 | $R^2$ = Me, Z = O, $R^3$ = 5-Me |
| 318 | $R^2$ = Me, Z = O, $R^3$ = 5-Et |
| 319 | $R^2$ = Me, Z = O, $R^3$ = 5-Ethynyl |
| 320 | $R^2$ = Me, Z = O, $R^3$ = 5-Ethenyl |
| 321 | $R^2$ = Me, Z = O, $R^3$ = 5-SO$_2$Me |
| 322 | $R^2$ = Me, Z = O, $R^3$ = 5-OAc |
| 323 | $R^2$ = Me, Z = O, $R^3$ = 5-c-Pr |
| 324 | $R^2$ = Me, Z = O, $R^3$ = 5-i-Pr |
| 325 | $R^2$ = Me, Z = O, $R^3$ = 5-Ph |
| 326 | $R^2$ = Me, Z = O, $R^3$ = 6-F |
| 327 | $R^2$ = Me, Z = O, $R^3$ = 6-Cl |
| 328 | $R^2$ = Me, Z = O, $R^3$ = 6-Br |
| 329 | $R^2$ = Me, Z = O, $R^3$ = 6-I |
| 330 | $R^2$ = Me, Z = O, $R^3$ = 6-CN |
| 331 | $R^2$ = Me, Z = O, $R^3$ = 6-NO$_2$ |

| Table | Header Row |
|---|---|
| 332 | $R^2$ = Me, Z = O, $R^3$ = 6-OMe |
| 333 | $R^2$ = Me, Z = O, $R^3$ = 6-OCF$_3$ |
| 334 | $R^2$ = Me, Z = O, $R^3$ = 6-CF$_3$ |
| 335 | $R^2$ = Me, Z = O, $R^3$ = 6-CHF$_2$ |
| 336 | $R^2$ = Me, Z = O, $R^3$ = 6-CH$_2$F |
| 337 | $R^2$ = Me, Z = O, $R^3$ = 6-CHO |
| 338 | $R^2$ = Me, Z = O, $R^3$ = 6-Me |
| 339 | $R^2$ = Me, Z = O, $R^3$ = 6-Et |
| 340 | $R^2$ = Me, Z = O, $R^3$ = 6-Ethynyl |
| 341 | $R^2$ = Me, Z = O, $R^3$ = 6-Ethenyl |
| 342 | $R^2$ = Me, Z = O, $R^3$ = 6-SO$_2$Me |
| 343 | $R^2$ = Me, Z = O, $R^3$ = 6-OAc |
| 344 | $R^2$ = Me, Z = O, $R^3$ = 6-c-Pr |
| 345 | $R^2$ = Me, Z = O, $R^3$ = 6-i-Pr |
| 346 | $R^2$ = Me, Z = O, $R^3$ = 6-Ph |
| 347 | $R^2$ = Me, Z = O, $R^3$ = 4,5-di-F |
| 348 | $R^2$ = Me, Z = O, $R^3$ = 4,5-di-Cl |
| 349 | $R^2$ = Me, Z = O, $R^3$ = 4,5-di-Br |
| 350 | $R^2$ = Me, Z = O, $R^3$ = 4,5-di-CN |
| 351 | $R^2$ = Me, Z = O, $R^3$ = 4,5-di-Me |
| 352 | $R^2$ = Me, Z = O, $R^3$ = 4,5-di-OMe |
| 353 | $R^2$ = Me, Z = O, $R^3$ = 4,5-di-CF$_3$ |
| 354 | $R^2$ = CN, Z = O, $R^3$ = H (m = 0) |
| 355 | $R^2$ = CN, Z = O, $R^3$ = 4-F |
| 356 | $R^2$ = CN, Z = O, $R^3$ = 4-Cl |
| 357 | $R^2$ = CN, Z = O, $R^3$ = 4-Br |
| 358 | $R^2$ = CN, Z = O, $R^3$ = 4-I |
| 359 | $R^2$ = CN, Z = O, $R^3$ = 4-CN |
| 360 | $R^2$ = CN, Z = O, $R^3$ = 4-NO$_2$ |
| 361 | $R^2$ = CN, Z = O, $R^3$ = 4-OMe |
| 362 | $R^2$ = CN, Z = O, $R^3$ = 4-OCF$_3$ |
| 363 | $R^2$ = CN, Z = O, $R^3$ = 4-CF$_3$ |
| 364 | $R^2$ = CN, Z = O, $R^3$ = 4-CHF$_2$ |
| 365 | $R^2$ = CN, Z = O, $R^3$ = 4-CH$_2$F |
| 366 | $R^2$ = CN, Z = O, $R^3$ = 4-CHO |
| 367 | $R^2$ = CN, Z = O, $R^3$ = 4-Me |
| 368 | $R^2$ = CN, Z = O, $R^3$ = 4-Et |
| 369 | $R^2$ = CN, Z = O, $R^3$ = 4-Ethynyl |
| 370 | $R^2$ = CN, Z = O, $R^3$ = 4-Ethenyl |
| 371 | $R^2$ = CN, Z = O, $R^3$ = 4-SO$_2$Me |
| 372 | $R^2$ = CN, Z = O, $R^3$ = 4-OAc |
| 373 | $R^2$ = CN, Z = O, $R^3$ = 4-c-Pr |
| 374 | $R^2$ = CN, Z = O, $R^3$ = 4-i-Pr |
| 375 | $R^2$ = CN, Z = O, $R^3$ = 4-Ph |
| 376 | $R^2$ = CN, Z = O, $R^3$ = 5-F |
| 377 | $R^2$ = CN, Z = O, $R^3$ = 5-Cl |
| 378 | $R^2$ = CN, Z = O, $R^3$ = 5-Br |
| 379 | $R^2$ = CN, Z = O, $R^3$ = 5-I |
| 380 | $R^2$ = CN, Z = O, $R^3$ = 5-CN |
| 381 | $R^2$ = CN, Z = O, $R^3$ = 5-NO$_2$ |
| 382 | $R^2$ = CN, Z = O, $R^3$ = 5-OMe |
| 383 | $R^2$ = CN, Z = O, $R^3$ = 5-OCF$_3$ |
| 384 | $R^2$ = CN, Z = O, $R^3$ = 5-CF$_3$ |
| 385 | $R^2$ = CN, Z = O, $R^3$ = 5-CHF$_2$ |
| 386 | $R^2$ = CN, Z = O, $R^3$ = 5-CH$_2$F |
| 387 | $R^2$ = CN, Z = O, $R^3$ = 5-CHO |
| 388 | $R^2$ = CN, Z = O, $R^3$ = 5-Me |
| 389 | $R^2$ = CN, Z = O, $R^3$ = 5-Et |
| 390 | $R^2$ = CN, Z = O, $R^3$ = 5-Ethynyl |
| 391 | $R^2$ = CN, Z = O, $R^3$ = 5-Ethenyl |
| 392 | $R^2$ = CN, Z = O, $R^3$ = 5-SO$_2$Me |
| 393 | $R^2$ = CN, Z = O, $R^3$ = 5-OAc |
| 394 | $R^2$ = CN, Z = O, $R^3$ = 5-c-Pr |
| 395 | $R^2$ = CN, Z = O, $R^3$ = 5-i-Pr |
| 396 | $R^2$ = CN, Z = O, $R^3$ = 5-Ph |
| 397 | $R^2$ = CN, Z = O, $R^3$ = 6-F |
| 398 | $R^2$ = CN, Z = O, $R^3$ = 6-Cl |
| 399 | $R^2$ = CN, Z = O, $R^3$ = 6-Br |
| 400 | $R^2$ = CN, Z = O, $R^3$ = 6-I |
| 401 | $R^2$ = CN, Z = O, $R^3$ = 6-CN |
| 402 | $R^2$ = CN, Z = O, $R^3$ = 6-NO$_2$ |
| 403 | $R^2$ = CN, Z = O, $R^3$ = 6-OMe |
| 404 | $R^2$ = CN, Z = O, $R^3$ = 6-OCF$_3$ |
| 405 | $R^2$ = CN, Z = O, $R^3$ = 6-CF$_3$ |
| 406 | $R^2$ = CN, Z = O, $R^3$ = 6-CHF$_2$ |
| 407 | $R^2$ = CN, Z = O, $R^3$ = 6-CH$_2$F |
| 408 | $R^2$ = CN, Z = O, $R^3$ = 6-CHO |
| 409 | $R^2$ = CN, Z = O, $R^3$ = 6-Me |
| 410 | $R^2$ = CN, Z = O, $R^3$ = 6-Et |
| 411 | $R^2$ = CN, Z = O, $R^3$ = 6-Ethynyl |
| 412 | $R^2$ = CN, Z = O, $R^3$ = 6-Ethenyl |
| 413 | $R^2$ = CN, Z = O, $R^3$ = 6-SO$_2$Me |
| 414 | $R^2$ = CN, Z = O, $R^3$ = 6-OAc |
| 415 | $R^2$ = CN, Z = O, $R^3$ = 6-c-Pr |
| 416 | $R^2$ = CN, Z = O, $R^3$ = 6-i-Pr |
| 417 | $R^2$ = CN, Z = O, $R^3$ = 6-Ph |
| 418 | $R^2$ = CN, Z = O, $R^3$ = 4,5-di-F |
| 419 | $R^2$ = CN, Z = O, $R^3$ = 4,5-di-Cl |
| 420 | $R^2$ = CN, Z = O, $R^3$ = 4,5-di-Br |
| 421 | $R^2$ = CN, Z = O, $R^3$ = 4,5-di-CN |
| 422 | $R^2$ = CN, Z = O, $R^3$ = 4,5-di-Me |
| 423 | $R^2$ = CN, Z = O, $R^3$ = 4,5-di-OMe |
| 424 | $R^2$ = CN, Z = O, $R^3$ = 4,5-di-CF$_3$ |
| 425 | $R^2$ = NO$_2$, Z = O, $R^3$ = H (m = 0) |
| 426 | $R^2$ = NO$_2$, Z = O, $R^3$ = 4-F |
| 427 | $R^2$ = NO$_2$, Z = O, $R^3$ = 4-Cl |
| 428 | $R^2$ = NO$_2$, Z = O, $R^3$ = 4-Br |
| 429 | $R^2$ = NO$_2$, Z = O, $R^3$ = 4-I |
| 430 | $R^2$ = NO$_2$, Z = O, $R^3$ = 4-CN |
| 431 | $R^2$ = NO$_2$, Z = O, $R^3$ = 4-NO$_2$ |
| 432 | $R^2$ = NO$_2$, Z = O, $R^3$ = 4-OMe |
| 433 | $R^2$ = NO$_2$, Z = O, $R^3$ = 4-OCF$_3$ |
| 434 | $R^2$ = NO$_2$, Z = O, $R^3$ = 4-CF$_3$ |
| 435 | $R^2$ = NO$_2$, Z = O, $R^3$ = 4-CHF$_2$ |
| 436 | $R^2$ = NO$_2$, Z = O, $R^3$ = 4-CH$_2$F |
| 437 | $R^2$ = NO$_2$, Z = O, $R^3$ = 4-CHO |
| 438 | $R^2$ = NO$_2$, Z = O, $R^3$ = 4-Me |
| 439 | $R^2$ = NO$_2$, Z = O, $R^3$ = 4-Et |
| 440 | $R^2$ = NO$_2$, Z = O, $R^3$ = 4-Ethynyl |
| 441 | $R^2$ = NO$_2$, Z = O, $R^3$ = 4-Ethenyl |
| 442 | $R^2$ = NO$_2$, Z = O, $R^3$ = 4-SO$_2$Me |
| 443 | $R^2$ = NO$_2$, Z = O, $R^3$ = 4-OAc |
| 444 | $R^2$ = NO$_2$, Z = O, $R^3$ = 4-c-Pr |
| 445 | $R^2$ = NO$_2$, Z = O, $R^3$ = 4-i-Pr |
| 446 | $R^2$ = NO$_2$, Z = O, $R^3$ = 4-Ph |
| 447 | $R^2$ = NO$_2$, Z = O, $R^3$ = 5-F |
| 448 | $R^2$ = NO$_2$, Z = O, $R^3$ = 5-Cl |
| 449 | $R^2$ = NO$_2$, Z = O, $R^3$ = 5-Br |
| 450 | $R^2$ = NO$_2$, Z = O, $R^3$ = 5-I |
| 451 | $R^2$ = NO$_2$, Z = O, $R^3$ = 5-CN |
| 452 | $R^2$ = NO$_2$, Z = O, $R^3$ = 5-NO$_2$ |
| 453 | $R^2$ = NO$_2$, Z = O, $R^3$ = 5-OMe |
| 454 | $R^2$ = NO$_2$, Z = O, $R^3$ = 5-OCF$_3$ |
| 455 | $R^2$ = NO$_2$, Z = O, $R^3$ = 5-CF$_3$ |
| 456 | $R^2$ = NO$_2$, Z = O, $R^3$ = 5-CHF$_2$ |
| 457 | $R^2$ = NO$_2$, Z = O, $R^3$ = 5-CH$_2$F |
| 458 | $R^2$ = NO$_2$, Z = O, $R^3$ = 5-CHO |
| 459 | $R^2$ = NO$_2$, Z = O, $R^3$ = 5-Me |
| 460 | $R^2$ = NO$_2$, Z = O, $R^3$ = 5-Et |
| 461 | $R^2$ = NO$_2$, Z = O, $R^3$ = 5-Ethynyl |
| 462 | $R^2$ = NO$_2$, Z = O, $R^3$ = 5-Ethenyl |
| 463 | $R^2$ = NO$_2$, Z = O, $R^3$ = 5-SO$_2$Me |
| 464 | $R^2$ = NO$_2$, Z = O, $R^3$ = 5-OAc |
| 465 | $R^2$ = NO$_2$, Z = O, $R^3$ = 5-c-Pr |
| 466 | $R^2$ = NO$_2$, Z = O, $R^3$ = 5-i-Pr |
| 467 | $R^2$ = NO$_2$, Z = O, $R^3$ = 5-Ph |
| 468 | $R^2$ = NO$_2$, Z = O, $R^3$ = 6-F |
| 469 | $R^2$ = NO$_2$, Z = O, $R^3$ = 6-Cl |
| 470 | $R^2$ = NO$_2$, Z = O, $R^3$ = 6-Br |
| 471 | $R^2$ = NO$_2$, Z = O, $R^3$ = 6-I |
| 472 | $R^2$ = NO$_2$, Z = O, $R^3$ = 6-CN |
| 473 | $R^2$ = NO$_2$, Z = O, $R^3$ = 6-NO$_2$ |
| 474 | $R^2$ = NO$_2$, Z = O, $R^3$ = 6-OMe |
| 475 | $R^2$ = NO$_2$, Z = O, $R^3$ = 6-OCF$_3$ |
| 476 | $R^2$ = NO$_2$, Z = O, $R^3$ = 6-CF$_3$ |
| 477 | $R^2$ = NO$_2$, Z = O, $R^3$ = 6-CHF$_2$ |
| 478 | $R^2$ = NO$_2$, Z = O, $R^3$ = 6-CH$_2$F |
| 479 | $R^2$ = NO$_2$, Z = O, $R^3$ = 6-CHO |
| 480 | $R^2$ = NO$_2$, Z = O, $R^3$ = 6-Me |
| 481 | $R^2$ = NO$_2$, Z = O, $R^3$ = 6-Et |
| 482 | $R^2$ = NO$_2$, Z = O, $R^3$ = 6-Ethynyl |
| 483 | $R^2$ = NO$_2$, Z = O, $R^3$ = 6-Ethenyl |
| 484 | $R^2$ = NO$_2$, Z = O, $R^3$ = 6-SO$_2$Me |
| 485 | $R^2$ = NO$_2$, Z = O, $R^3$ = 6-OAc |

| Table | Header Row |
|---|---|
| 486 | $R^2 = NO_2$, $Z = O$, $R^3 = 6$-c-Pr |
| 487 | $R^2 = NO_2$, $Z = O$, $R^3 = 6$-i-Pr |
| 488 | $R^2 = NO_2$, $Z = O$, $R^3 = 6$-Ph |
| 489 | $R^2 = NO_2$, $Z = O$, $R^3 = 4,5$-di-F |
| 490 | $R^2 = NO_2$, $Z = O$, $R^3 = 4,5$-di-Cl |
| 491 | $R^2 = NO_2$, $Z = O$, $R^3 = 4,5$-di-Br |
| 492 | $R^2 = NO_2$, $Z = O$, $R^3 = 4,5$-di-CN |
| 493 | $R^2 = NO_2$, $Z = O$, $R^3 = 4,5$-di-Me |
| 494 | $R^2 = NO_2$, $Z = O$, $R^3 = 4,5$-di-OMe |
| 495 | $R^2 = NO_2$, $Z = O$, $R^3 = 4,5$-di-CF_3$ |
| 496 | $R^2 = OMe$, $Z = O$, $R^3 = H$ ($m = 0$) |
| 497 | $R^2 = OMe$, $Z = O$, $R^3 = 4$-F |
| 498 | $R^2 = OMe$, $Z = O$, $R^3 = 4$-Cl |
| 499 | $R^2 = OMe$, $Z = O$, $R^3 = 4$-Br |
| 500 | $R^2 = OMe$, $Z = O$, $R^3 = 4$-I |
| 501 | $R^2 = OMe$, $Z = O$, $R^3 = 4$-CN |
| 502 | $R^2 = OMe$, $Z = O$, $R^3 = 4$-NO_2$ |
| 503 | $R^2 = OMe$, $Z = O$, $R^3 = 4$-OMe |
| 504 | $R^2 = OMe$, $Z = O$, $R^3 = 4$-OCF_3$ |
| 505 | $R^2 = OMe$, $Z = O$, $R^3 = 4$-CF_3$ |
| 506 | $R^2 = OMe$, $Z = O$, $R^3 = 4$-CHF_2$ |
| 507 | $R^2 = OMe$, $Z = O$, $R^3 = 4$-CH_2F$ |
| 508 | $R^2 = OMe$, $Z = O$, $R^3 = 4$-CHO |
| 509 | $R^2 = OMe$, $Z = O$, $R^3 = 4$-Me |
| 510 | $R^2 = OMe$, $Z = O$, $R^3 = 4$-Et |
| 511 | $R^2 = OMe$, $Z = O$, $R^3 = 4$-Ethynyl |
| 512 | $R^2 = OMe$, $Z = O$, $R^3 = 4$-Ethenyl |
| 513 | $R^2 = OMe$, $Z = O$, $R^3 = 4$-SO_2Me |
| 514 | $R^2 = OMe$, $Z = O$, $R^3 = 4$-OAc |
| 515 | $R^2 = OMe$, $Z = O$, $R^3 = 4$-c-Pr |
| 516 | $R^2 = OMe$, $Z = O$, $R^3 = 4$-i-Pr |
| 517 | $R^2 = OMe$, $Z = O$, $R^3 = 4$-Ph |
| 518 | $R^2 = OMe$, $Z = O$, $R^3 = 5$-F |
| 519 | $R^2 = OMe$, $Z = O$, $R^3 = 5$-Cl |
| 520 | $R^2 = OMe$, $Z = O$, $R^3 = 5$-Br |
| 521 | $R^2 = OMe$, $Z = O$, $R^3 = 5$-I |
| 522 | $R^2 = OMe$, $Z = O$, $R^3 = 5$-CN |
| 523 | $R^2 = OMe$, $Z = O$, $R^3 = 5$-NO_2$ |
| 524 | $R^2 = OMe$, $Z = O$, $R^3 = 5$-OMe |
| 525 | $R^2 = OMe$, $Z = O$, $R^3 = 5$-OCF_3$ |
| 526 | $R^2 = OMe$, $Z = O$, $R^3 = 5$-CF_3$ |
| 527 | $R^2 = OMe$, $Z = O$, $R^3 = 5$-CHF_2$ |
| 528 | $R^2 = OMe$, $Z = O$, $R^3 = 5$-CH_2F$ |
| 529 | $R^2 = OMe$, $Z = O$, $R^3 = 5$-CHO |
| 530 | $R^2 = OMe$, $Z = O$, $R^3 = 5$-Me |
| 531 | $R^2 = OMe$, $Z = O$, $R^3 = 5$-Et |
| 532 | $R^2 = OMe$, $Z = O$, $R^3 = 5$-Ethynyl |
| 533 | $R^2 = OMe$, $Z = O$, $R^3 = 5$-Ethenyl |
| 534 | $R^2 = OMe$, $Z = O$, $R^3 = 5$-SO_2Me |
| 535 | $R^2 = OMe$, $Z = O$, $R^3 = 5$-OAc |
| 536 | $R^2 = OMe$, $Z = O$, $R^3 = 5$-c-Pr |
| 537 | $R^2 = OMe$, $Z = O$, $R^3 = 5$-i-Pr |
| 538 | $R^2 = OMe$, $Z = O$, $R^3 = 5$-Ph |
| 539 | $R^2 = OMe$, $Z = O$, $R^3 = 6$-F |
| 540 | $R^2 = OMe$, $Z = O$, $R^3 = 6$-Cl |
| 541 | $R^2 = OMe$, $Z = O$, $R^3 = 6$-Br |
| 542 | $R^2 = OMe$, $Z = O$, $R^3 = 6$-I |
| 543 | $R^2 = OMe$, $Z = O$, $R^3 = 6$-CN |
| 544 | $R^2 = OMe$, $Z = O$, $R^3 = 6$-NO_2$ |
| 545 | $R^2 = OMe$, $Z = O$, $R^3 = 6$-OMe |
| 546 | $R^2 = OMe$, $Z = O$, $R^3 = 6$-OCF_3$ |
| 547 | $R^2 = OMe$, $Z = O$, $R^3 = 6$-CF_3$ |
| 548 | $R^2 = OMe$, $Z = O$, $R^3 = 6$-CHF_2$ |
| 549 | $R^2 = OMe$, $Z = O$, $R^3 = 6$-CH_2F$ |
| 550 | $R^2 = OMe$, $Z = O$, $R^3 = 6$-CHO |
| 551 | $R^2 = OMe$, $Z = O$, $R^3 = 6$-Me |
| 552 | $R^2 = OMe$, $Z = O$, $R^3 = 6$-Et |
| 553 | $R^2 = OMe$, $Z = O$, $R^3 = 6$-Ethynyl |
| 554 | $R^2 = OMe$, $Z = O$, $R^3 = 6$-Ethenyl |
| 555 | $R^2 = OMe$, $Z = O$, $R^3 = 6$-SO_2Me |
| 556 | $R^2 = OMe$, $Z = O$, $R^3 = 6$-OAc |
| 557 | $R^2 = OMe$, $Z = O$, $R^3 = 6$-c-Pr |
| 558 | $R^2 = OMe$, $Z = O$, $R^3 = 6$-i-Pr |
| 559 | $R^2 = OMe$, $Z = O$, $R^3 = 6$-Ph |
| 560 | $R^2 = OMe$, $Z = O$, $R^3 = 4,5$-di-F |
| 561 | $R^2 = OMe$, $Z = O$, $R^3 = 4,5$-di-Cl |
| 562 | $R^2 = OMe$, $Z = O$, $R^3 = 4,5$-di-Br |
| 563 | $R^2 = OMe$, $Z = O$, $R^3 = 4,5$-di-CN |
| 564 | $R^2 = OMe$, $Z = O$, $R^3 = 4,5$-di-Me |
| 565 | $R^2 = OMe$, $Z = O$, $R^3 = 4,5$-di-OMe |
| 566 | $R^2 = OMe$, $Z = O$, $R^3 = 4,5$-di-CF_3$ |
| 567 | $R^2 = CF_3$, $Z = O$, $R^3 = H$ ($m = 0$) |
| 568 | $R^2 = CF_3$, $Z = O$, $R^3 = 4$-F |
| 569 | $R^2 = CF_3$, $Z = O$, $R^3 = 4$-Cl |
| 570 | $R^2 = CF_3$, $Z = O$, $R^3 = 4$-Br |
| 571 | $R^2 = CF_3$, $Z = O$, $R^3 = 4$-I |
| 572 | $R^2 = CF_3$, $Z = O$, $R^3 = 4$-CN |
| 573 | $R^2 = CF_3$, $Z = O$, $R^3 = 4$-NO_2$ |
| 574 | $R^2 = CF_3$, $Z = O$, $R^3 = 4$-OMe |
| 575 | $R^2 = CF_3$, $Z = O$, $R^3 = 4$-OCF_3$ |
| 576 | $R^2 = CF_3$, $Z = O$, $R^3 = 4$-CF_3$ |
| 577 | $R^2 = CF_3$, $Z = O$, $R^3 = 4$-CHF_2$ |
| 578 | $R^2 = CF_3$, $Z = O$, $R^3 = 4$-CH_2F$ |
| 579 | $R^2 = CF_3$, $Z = O$, $R^3 = 4$-CHO |
| 580 | $R^2 = CF_3$, $Z = O$, $R^3 = 4$-Me |
| 581 | $R^2 = CF_3$, $Z = O$, $R^3 = 4$-Et |
| 582 | $R^2 = CF_3$, $Z = O$, $R^3 = 4$-Ethynyl |
| 583 | $R^2 = CF_3$, $Z = O$, $R^3 = 4$-Ethenyl |
| 584 | $R^2 = CF_3$, $Z = O$, $R^3 = 4$-SO_2Me |
| 585 | $R^2 = CF_3$, $Z = O$, $R^3 = 4$-OAc |
| 586 | $R^2 = CF_3$, $Z = O$, $R^3 = 4$-c-Pr |
| 587 | $R^2 = CF_3$, $Z = O$, $R^3 = 4$-i-Pr |
| 588 | $R^2 = CF_3$, $Z = O$, $R^3 = 4$-Ph |
| 589 | $R^2 = CF_3$, $Z = O$, $R^3 = 5$-F |
| 590 | $R^2 = CF_3$, $Z = O$, $R^3 = 5$-Cl |
| 591 | $R^2 = CF_3$, $Z = O$, $R^3 = 5$-Br |
| 592 | $R^2 = CF_3$, $Z = O$, $R^3 = 5$-I |
| 593 | $R^2 = CF_3$, $Z = O$, $R^3 = 5$-CN |
| 594 | $R^2 = CF_3$, $Z = O$, $R^3 = 5$-NO_2$ |
| 595 | $R^2 = CF_3$, $Z = O$, $R^3 = 5$-OMe |
| 596 | $R^2 = CF_3$, $Z = O$, $R^3 = 5$-OCF_3$ |
| 597 | $R^2 = CF_3$, $Z = O$, $R^3 = 5$-CF_3$ |
| 598 | $R^2 = CF_3$, $Z = O$, $R^3 = 5$-CHF_2$ |
| 599 | $R^2 = CF_3$, $Z = O$, $R^3 = 5$-CH_2F$ |
| 600 | $R^2 = CF_3$, $Z = O$, $R^3 = 5$-CHO |
| 601 | $R^2 = CF_3$, $Z = O$, $R^3 = 5$-Me |
| 602 | $R^2 = CF_3$, $Z = O$, $R^3 = 5$-Et |
| 603 | $R^2 = CF_3$, $Z = O$, $R^3 = 5$-Ethynyl |
| 604 | $R^2 = CF_3$, $Z = O$, $R^3 = 5$-Ethenyl |
| 605 | $R^2 = CF_3$, $Z = O$, $R^3 = 5$-SO_2Me |
| 606 | $R^2 = CF_3$, $Z = O$, $R^3 = 5$-OAc |
| 607 | $R^2 = CF_3$, $Z = O$, $R^3 = 5$-c-Pr |
| 608 | $R^2 = CF_3$, $Z = O$, $R^3 = 5$-i-Pr |
| 609 | $R^2 = CF_3$, $Z = O$, $R^3 = 5$-Ph |
| 610 | $R^2 = CF_3$, $Z = O$, $R^3 = 6$-F |
| 611 | $R^2 = CF_3$, $Z = O$, $R^3 = 6$-Cl |
| 612 | $R^2 = CF_3$, $Z = O$, $R^3 = 6$-Br |
| 613 | $R^2 = CF_3$, $Z = O$, $R^3 = 6$-I |
| 614 | $R^2 = CF_3$, $Z = O$, $R^3 = 6$-CN |
| 615 | $R^2 = CF_3$, $Z = O$, $R^3 = 6$-NO_2$ |
| 616 | $R^2 = CF_3$, $Z = O$, $R^3 = 6$-OMe |
| 617 | $R^2 = CF_3$, $Z = O$, $R^3 = 6$-OCF_3$ |
| 618 | $R^2 = CF_3$, $Z = O$, $R^3 = 6$-CF_3$ |
| 619 | $R^2 = CF_3$, $Z = O$, $R^3 = 6$-CHF_2$ |
| 620 | $R^2 = CF_3$, $Z = O$, $R^3 = 6$-CH_2F$ |
| 621 | $R^2 = CF_3$, $Z = O$, $R^3 = 6$-CHO |
| 622 | $R^2 = CF_3$, $Z = O$, $R^3 = 6$-Me |
| 623 | $R^2 = CF_3$, $Z = O$, $R^3 = 6$-Et |
| 624 | $R^2 = CF_3$, $Z = O$, $R^3 = 6$-Ethynyl |
| 625 | $R^2 = CF_3$, $Z = O$, $R^3 = 6$-Ethenyl |
| 626 | $R^2 = CF_3$, $Z = O$, $R^3 = 6$-SO_2Me |
| 627 | $R^2 = CF_3$, $Z = O$, $R^3 = 6$-OAc |
| 628 | $R^2 = CF_3$, $Z = O$, $R^3 = 6$-c-Pr |
| 629 | $R^2 = CF_3$, $Z = O$, $R^3 = 6$-i-Pr |
| 630 | $R^2 = CF_3$, $Z = O$, $R^3 = 6$-Ph |
| 631 | $R^2 = CF_3$, $Z = O$, $R^3 = 4,5$-di-F |
| 632 | $R^2 = CF_3$, $Z = O$, $R^3 = 4,5$-di-Cl |
| 633 | $R^2 = CF_3$, $Z = O$, $R^3 = 4,5$-di-Br |
| 634 | $R^2 = CF_3$, $Z = O$, $R^3 = 4,5$-di-CN |
| 635 | $R^2 = CF_3$, $Z = O$, $R^3 = 4,5$-di-Me |
| 636 | $R^2 = CF_3$, $Z = O$, $R^3 = 4,5$-di-OMe |
| 637 | $R^2 = CHF_2$, $Z = O$, $R^3 = H$ ($m = 0$) |
| 638 | $R^2 = CHF_2$, $Z = O$, $R^3 = 4$-F |
| 639 | $R^2 = CHF_2$, $Z = O$, $R^3 = 4$-Cl |

| Table | Header Row |
|---|---|
| 640 | $R^2 = CHF_2$, $Z = O$, $R^3 = 4\text{-Br}$ |
| 641 | $R^2 = CHF_2$, $Z = O$, $R^3 = 4\text{-I}$ |
| 642 | $R^2 = CHF_2$, $Z = O$, $R^3 = 4\text{-CN}$ |
| 643 | $R^2 = CHF_2$, $Z = O$, $R^3 = 4\text{-NO}_2$ |
| 644 | $R^2 = CHF_2$, $Z = O$, $R^3 = 4\text{-OMe}$ |
| 645 | $R^2 = CHF_2$, $Z = O$, $R^3 = 4\text{-OCF}_3$ |
| 646 | $R^2 = CHF_2$, $Z = O$, $R^3 = 4\text{-CF}_3$ |
| 647 | $R^2 = CHF_2$, $Z = O$, $R^3 = 4\text{-CHF}_2$ |
| 648 | $R^2 = CHF_2$, $Z = O$, $R^3 = 4\text{-CH}_2F$ |
| 649 | $R^2 = CHF_2$, $Z = O$, $R^3 = 4\text{-CHO}$ |
| 650 | $R^2 = CHF_2$, $Z = O$, $R^3 = 4\text{-Me}$ |
| 651 | $R^2 = CHF_2$, $Z = O$, $R^3 = 4\text{-Et}$ |
| 652 | $R^2 = CHF_2$, $Z = O$, $R^3 = 4\text{-Ethynyl}$ |
| 653 | $R^2 = CHF_2$, $Z = O$, $R^3 = 4\text{-Ethenyl}$ |
| 654 | $R^2 = CHF_2$, $Z = O$, $R^3 = 4\text{-SO}_2Me$ |
| 655 | $R^2 = CHF_2$, $Z = O$, $R^3 = 4\text{-OAc}$ |
| 656 | $R^2 = CHF_2$, $Z = O$, $R^3 = 4\text{-c-Pr}$ |
| 657 | $R^2 = CHF_2$, $Z = O$, $R^3 = 4\text{-i-Pr}$ |
| 658 | $R^2 = CHF_2$, $Z = O$, $R^3 = 4\text{-Ph}$ |
| 659 | $R^2 = CHF_2$, $Z = O$, $R^3 = 5\text{-F}$ |
| 660 | $R^2 = CHF_2$, $Z = O$, $R^3 = 5\text{-Cl}$ |
| 661 | $R^2 = CHF_2$, $Z = O$, $R^3 = 5\text{-Br}$ |
| 662 | $R^2 = CHF_2$, $Z = O$, $R^3 = 5\text{-I}$ |
| 663 | $R^2 = CHF_2$, $Z = O$, $R^3 = 5\text{-CN}$ |
| 664 | $R^2 = CHF_2$, $Z = O$, $R^3 = 5\text{-NO}_2$ |
| 665 | $R^2 = CHF_2$, $Z = O$, $R^3 = 5\text{-OMe}$ |
| 666 | $R^2 = CHF_2$, $Z = O$, $R^3 = 5\text{-OCF}_3$ |
| 667 | $R^2 = CHF_2$, $Z = O$, $R^3 = 5\text{-CF}_3$ |
| 668 | $R^2 = CHF_2$, $Z = O$, $R^3 = 5\text{-CHF}_2$ |
| 669 | $R^2 = CHF_2$, $Z = O$, $R^3 = 5\text{-CH}_2F$ |
| 670 | $R^2 = CHF_2$, $Z = O$, $R^3 = 5\text{-CHO}$ |
| 671 | $R^2 = CHF_2$, $Z = O$, $R^3 = 5\text{-Me}$ |
| 672 | $R^2 = CHF_2$, $Z = O$, $R^3 = 5\text{-Et}$ |
| 673 | $R^2 = CHF_2$, $Z = O$, $R^3 = 5\text{-Ethynyl}$ |
| 674 | $R^2 = CHF_2$, $Z = O$, $R^3 = 5\text{-Ethenyl}$ |
| 675 | $R^2 = CHF_2$, $Z = O$, $R^3 = 5\text{-SO}_2Me$ |
| 676 | $R^2 = CHF_2$, $Z = O$, $R^3 = 5\text{-OAc}$ |
| 677 | $R^2 = CHF_2$, $Z = O$, $R^3 = 5\text{-c-Pr}$ |
| 678 | $R^2 = CHF_2$, $Z = O$, $R^3 = 5\text{-i-Pr}$ |
| 679 | $R^2 = CHF_2$, $Z = O$, $R^3 = 5\text{-Ph}$ |
| 680 | $R^2 = CHF_2$, $Z = O$, $R^3 = 6\text{-F}$ |
| 681 | $R^2 = CHF_2$, $Z = O$, $R^3 = 6\text{-Cl}$ |
| 682 | $R^2 = CHF_2$, $Z = O$, $R^3 = 6\text{-Br}$ |
| 683 | $R^2 = CHF_2$, $Z = O$, $R^3 = 6\text{-I}$ |
| 684 | $R^2 = CHF_2$, $Z = O$, $R^3 = 6\text{-CN}$ |
| 685 | $R^2 = CHF_2$, $Z = O$, $R^3 = 6\text{-NO}_2$ |
| 686 | $R^2 = CHF_2$, $Z = O$, $R^3 = 6\text{-OMe}$ |
| 687 | $R^2 = CHF_2$, $Z = O$, $R^3 = 6\text{-OCF}_3$ |
| 688 | $R^2 = CHF_2$, $Z = O$, $R^3 = 6\text{-CF}_3$ |
| 689 | $R^2 = CHF_2$, $Z = O$, $R^3 = 6\text{-CHF}_2$ |
| 690 | $R^2 = CHF_2$, $Z = O$, $R^3 = 6\text{-CH}_2F$ |
| 691 | $R^2 = CHF_2$, $Z = O$, $R^3 = 6\text{-CHO}$ |
| 692 | $R^2 = CHF_2$, $Z = O$, $R^3 = 6\text{-Me}$ |
| 693 | $R^2 = CHF_2$, $Z = O$, $R^3 = 6\text{-Et}$ |
| 694 | $R^2 = CHF_2$, $Z = O$, $R^3 = 6\text{-Ethynyl}$ |
| 695 | $R^2 = CHF_2$, $Z = O$, $R^3 = 6\text{-Ethenyl}$ |
| 696 | $R^2 = CHF_2$, $Z = O$, $R^3 = 6\text{-SO}_2Me$ |
| 697 | $R^2 = CHF_2$, $Z = O$, $R^3 = 6\text{-OAc}$ |
| 698 | $R^2 = CHF_2$, $Z = O$, $R^3 = 6\text{-c-Pr}$ |
| 699 | $R^2 = CHF_2$, $Z = O$, $R^3 = 6\text{-i-Pr}$ |
| 700 | $R^2 = CHF_2$, $Z = O$, $R^3 = 6\text{-Ph}$ |
| 701 | $R^2 = CHF_2$, $Z = O$, $R^3 = 4,5\text{-di-F}$ |
| 702 | $R^2 = CHF_2$, $Z = O$, $R^3 = 4,5\text{-di-Cl}$ |
| 703 | $R^2 = CHF_2$, $Z = O$, $R^3 = 4,5\text{-di-Br}$ |
| 704 | $R^2 = CHF_2$, $Z = O$, $R^3 = 4,5\text{-di-CN}$ |
| 705 | $R^2 = CHF_2$, $Z = O$, $R^3 = 4,5\text{-di-Me}$ |
| 706 | $R^2 = CHF_2$, $Z = O$, $R^3 = 4,5\text{-di-OMe}$ |
| 707 | $R^2 = CHF_2$, $Z = O$, $R^3 = 4,5\text{-di-CF}_3$ |
| 708 | $R^2 = SO_2Me$, $Z = O$, $R^3 = H$ (m = 0) |
| 709 | $R^2 = SO_2Me$, $Z = O$, $R^3 = 4\text{-F}$ |
| 710 | $R^2 = SO_2Me$, $Z = O$, $R^3 = 4\text{-Cl}$ |
| 711 | $R^2 = SO_2Me$, $Z = O$, $R^3 = 4\text{-Br}$ |
| 712 | $R^2 = SO_2Me$, $Z = O$, $R^3 = 4\text{-I}$ |
| 713 | $R^2 = SO_2Me$, $Z = O$, $R^3 = 4\text{-CN}$ |
| 714 | $R^2 = SO_2Me$, $Z = O$, $R^3 = 4\text{-NO}_2$ |
| 715 | $R^2 = SO_2Me$, $Z = O$, $R^3 = 4\text{-OMe}$ |
| 716 | $R^2 = SO_2Me$, $Z = O$, $R^3 = 4\text{-OCF}_3$ |
| 717 | $R^2 = SO_2Me$, $Z = O$, $R^3 = 4\text{-CF}_3$ |
| 718 | $R^2 = SO_2Me$, $Z = O$, $R^3 = 4\text{-CHF}_2$ |
| 719 | $R^2 = SO_2Me$, $Z = O$, $R^3 = 4\text{-CH}_2F$ |
| 720 | $R^2 = SO_2Me$, $Z = O$, $R^3 = 4\text{-CHO}$ |
| 721 | $R^2 = SO_2Me$, $Z = O$, $R^3 = 4\text{-Me}$ |
| 722 | $R^2 = SO_2Me$, $Z = O$, $R^3 = 4\text{-Et}$ |
| 723 | $R^2 = SO_2Me$, $Z = O$, $R^3 = 4\text{-Ethynyl}$ |
| 724 | $R^2 = SO_2Me$, $Z = O$, $R^3 = 4\text{-Ethenyl}$ |
| 725 | $R^2 = SO_2Me$, $Z = O$, $R^3 = 4\text{-SO}_2Me$ |
| 726 | $R^2 = SO_2Me$, $Z = O$, $R^3 = 4\text{-OAc}$ |
| 727 | $R^2 = SO_2Me$, $Z = O$, $R^3 = 4\text{-c-Pr}$ |
| 728 | $R^2 = SO_2Me$, $Z = O$, $R^3 = 4\text{-i-Pr}$ |
| 729 | $R^2 = SO_2Me$, $Z = O$, $R^3 = 4\text{-Ph}$ |
| 730 | $R^2 = SO_2Me$, $Z = O$, $R^3 = 5\text{-F}$ |
| 731 | $R^2 = SO_2Me$, $Z = O$, $R^3 = 5\text{-Cl}$ |
| 732 | $R^2 = SO_2Me$, $Z = O$, $R^3 = 5\text{-Br}$ |
| 733 | $R^2 = SO_2Me$, $Z = O$, $R^3 = 5\text{-I}$ |
| 734 | $R^2 = SO_2Me$, $Z = O$, $R^3 = 5\text{-CN}$ |
| 735 | $R^2 = SO_2Me$, $Z = O$, $R^3 = 5\text{-NO}_2$ |
| 736 | $R^2 = SO_2Me$, $Z = O$, $R^3 = 5\text{-OMe}$ |
| 737 | $R^2 = SO_2Me$, $Z = O$, $R^3 = 5\text{-OCF}_3$ |
| 738 | $R^2 = SO_2Me$, $Z = O$, $R^3 = 5\text{-CF}_3$ |
| 739 | $R^2 = SO_2Me$, $Z = O$, $R^3 = 5\text{-CHF}_2$ |
| 740 | $R^2 = SO_2Me$, $Z = O$, $R^3 = 5\text{-CH}_2F$ |
| 741 | $R^2 = SO_2Me$, $Z = O$, $R^3 = 5\text{-CHO}$ |
| 742 | $R^2 = SO_2Me$, $Z = O$, $R^3 = 5\text{-Me}$ |
| 743 | $R^2 = SO_2Me$, $Z = O$, $R^3 = 5\text{-Et}$ |
| 744 | $R^2 = SO_2Me$, $Z = O$, $R^3 = 5\text{-Ethynyl}$ |
| 745 | $R^2 = SO_2Me$, $Z = O$, $R^3 = 5\text{-Ethenyl}$ |
| 746 | $R^2 = SO_2Me$, $Z = O$, $R^3 = 5\text{-SO}_2Me$ |
| 747 | $R^2 = SO_2Me$, $Z = O$, $R^3 = 5\text{-OAc}$ |
| 748 | $R^2 = SO_2Me$, $Z = O$, $R^3 = 5\text{-c-Pr}$ |
| 749 | $R^2 = SO_2Me$, $Z = O$, $R^3 = 5\text{-i-Pr}$ |
| 750 | $R^2 = SO_2Me$, $Z = O$, $R^3 = 5\text{-Ph}$ |
| 751 | $R^2 = SO_2Me$, $Z = O$, $R^3 = 6\text{-F}$ |
| 752 | $R^2 = SO_2Me$, $Z = O$, $R^3 = 6\text{-Cl}$ |
| 753 | $R^2 = SO_2Me$, $Z = O$, $R^3 = 6\text{-Br}$ |
| 754 | $R^2 = SO_2Me$, $Z = O$, $R^3 = 6\text{-I}$ |
| 755 | $R^2 = SO_2Me$, $Z = O$, $R^3 = 6\text{-CN}$ |
| 756 | $R^2 = SO_2Me$, $Z = O$, $R^3 = 6\text{-NO}_2$ |
| 757 | $R^2 = SO_2Me$, $Z = O$, $R^3 = 6\text{-OMe}$ |
| 758 | $R^2 = SO_2Me$, $Z = O$, $R^3 = 6\text{-OCF}_3$ |
| 759 | $R^2 = SO_2Me$, $Z = O$, $R^3 = 6\text{-CF}_3$ |
| 760 | $R^2 = SO_2Me$, $Z = O$, $R^3 = 6\text{-CHF}_2$ |
| 761 | $R^2 = SO_2Me$, $Z = O$, $R^3 = 6\text{-CH}_2F$ |
| 762 | $R^2 = SO_2Me$, $Z = O$, $R^3 = 6\text{-CHO}$ |
| 763 | $R^2 = SO_2Me$, $Z = O$, $R^3 = 6\text{-Me}$ |
| 764 | $R^2 = SO_2Me$, $Z = O$, $R^3 = 6\text{-Et}$ |
| 765 | $R^2 = SO_2Me$, $Z = O$, $R^3 = 6\text{-Ethynyl}$ |
| 766 | $R^2 = SO_2Me$, $Z = O$, $R^3 = 6\text{-Ethenyl}$ |
| 767 | $R^2 = SO_2Me$, $Z = O$, $R^3 = 6\text{-SO}_2Me$ |
| 768 | $R^2 = SO_2Me$, $Z = O$, $R^3 = 6\text{-OAc}$ |
| 769 | $R^2 = SO_2Me$, $Z = O$, $R^3 = 6\text{-c-Pr}$ |
| 770 | $R^2 = SO_2Me$, $Z = O$, $R^3 = 6\text{-i-Pr}$ |
| 771 | $R^2 = SO_2Me$, $Z = O$, $R^3 = 6\text{-Ph}$ |
| 772 | $R^2 = SO_2Me$, $Z = O$, $R^3 = 4,5\text{-di-F}$ |
| 773 | $R^2 = SO_2Me$, $Z = O$, $R^3 = 4,5\text{-di-Cl}$ |
| 774 | $R^2 = SO_2Me$, $Z = O$, $R^3 = 4,5\text{-di-Br}$ |
| 775 | $R^2 = SO_2Me$, $Z = O$, $R^3 = 4,5\text{-di-CN}$ |
| 776 | $R^2 = SO_2Me$, $Z = O$, $R^3 = 4,5\text{-di-Me}$ |
| 777 | $R^2 = SO_2Me$, $Z = O$, $R^3 = 4,5\text{-di-OMe}$ |
| 778 | $R^2 = SO_2Me$, $Z = O$, $R^3 = 4,5\text{-di-CF}_3$ |

A compound of this invention will generally be used as a herbicidal active ingredient in a composition, i.e. formulation, with at least one additional component selected from the group consisting of surfactants, solid diluents and liquid diluents, which serves as a carrier. The formulation or composition ingredients are selected to be consistent with the physical properties of the active ingredient, mode of application and environmental factors such as soil type, moisture and temperature.

Useful formulations include both liquid and solid compositions. Liquid compositions include solutions (including emulsifiable concentrates), suspensions, emulsions (including microemulsions, oil-in-water emulsions, flowable concentrates and/or suspoemulsions) and the like, which optionally can be thickened into gels. The general types of aqueous liquid compositions are soluble concentrate, suspension concentrate, capsule suspension, concentrated emulsion, microemulsion, oil-in-water emulsion, flowable concentrate and suspo-emulsion. The general types of nonaqueous liquid compositions are emulsifiable concentrate, microemulsifiable concentrate, dispersible concentrate and oil dispersion.

The general types of solid compositions are dusts, powders, granules, pellets, prills, pastilles, tablets, filled films (including seed coatings) and the like, which can be water-dispersible ("wettable") or water-soluble. Films and coatings formed from film-forming solutions or flowable suspensions are particularly useful for seed treatment. Active ingredient can be (micro)encapsulated and further formed into a suspension or solid formulation; alternatively the entire formulation of active ingredient can be encapsulated (or "overcoated"). Encapsulation can control or delay release of the active ingredient. An emulsifiable granule combines the advantages of both an emulsifiable concentrate formulation and a dry granular formulation. High-strength compositions are primarily used as intermediates for further formulation.

Sprayable formulations are typically extended in a suitable medium before spraying. Such liquid and solid formulations are formulated to be readily diluted in the spray medium, usually water, but occasionally another suitable medium like an aromatic or paraffinic hydrocarbon or vegetable oil. Spray volumes can range from about from about one to several thousand liters per hectare, but more typically are in the range from about ten to several hundred liters per hectare. Sprayable formulations can be tank mixed with water or another suitable medium for foliar treatment by aerial or ground application, or for application to the growing medium of the plant. Liquid and dry formulations can be metered directly into drip irrigation systems or metered into the furrow during planting.

The formulations will typically contain effective amounts of active ingredient, diluent and surfactant within the following approximate ranges which add up to 100 percent by weight.

| | Weight Percent | | |
|---|---|---|---|
| | Active Ingredient | Diluent | Surfactant |
| Water-Dispersible and Water-soluble Granules, Tablets and Powders | 0.001-90 | 0-99.999 | 0-15 |
| Oil Dispersions, Suspensions, Emulsions, Solutions (including Emulsifiable Concentrates) | 1-50 | 40-99 | 0-50 |
| Dusts | 1-25 | 70-99 | 0-5 |
| Granules and Pellets | 0.001-99 | 5-99.999 | 0-15 |
| High Strength Compositions | 90-99 | 0-10 | 0-2 |

Solid diluents include, for example, clays such as bentonite, montmorillonite, attapulgite and kaolin, gypsum, cellulose, titanium dioxide, zinc oxide, starch, dextrin, sugars (e.g., lactose, sucrose), silica, talc, mica, diatomaceous earth, urea, calcium carbonate, sodium carbonate and bicarbonate, and sodium sulfate. Typical solid diluents are described in Watkins et al., *Handbook of Insecticide Dust Diluents and Carriers,* 2nd Ed., Dorland Books, Caldwell, N.J.

Liquid diluents include, for example, water, N,N-dimethylalkanamides (e.g., N,N-dimethylformamide), limonene, dimethyl sulfoxide, N-alkylpyrrolidones (e.g., N-methylpyrrolidinone), alkyl phosphates (e.g., triethyl phosphate), ethylene glycol, triethylene glycol, propylene glycol, dipropylene glycol, polypropylene glycol, propylene carbonate, butylene carbonate, paraffins (e.g., white mineral oils, normal paraffins, isoparaffins), alkylbenzenes, alkylnaphthalenes, glycerine, glycerol triacetate, sorbitol, aromatic hydrocarbons, dearomatized aliphatics, alkylbenzenes, alkylnaphthalenes, ketones such as cyclohexanone, 2-heptanone, isophorone and 4-hydroxy-4-methyl-2-pentanone, acetates such as isoamyl acetate, hexyl acetate, heptyl acetate, octyl acetate, nonyl acetate, tridecyl acetate and isobornyl acetate, other esters such as alkylated lactate esters, dibasic esters, alkyl and aryl benzoates and γ-butyrolactone, and alcohols, which can be linear, branched, saturated or unsaturated, such as methanol, ethanol, n-propanol, isopropyl alcohol, n-butanol, isobutyl alcohol, n-hexanol, 2-ethylhexanol, n-octanol, decanol, isodecyl alcohol, isooctadecanol, cetyl alcohol, lauryl alcohol, tridecyl alcohol, oleyl alcohol, cyclohexanol, tetrahydrofurfuryl alcohol, diacetone alcohol, cresol and benzyl alcohol. Liquid diluents also include glycerol esters of saturated and unsaturated fatty acids (typically $C_6$-$C_{22}$), such as plant seed and fruit oils (e.g., oils of olive, castor, linseed, sesame, corn (maize), peanut, sunflower, grapeseed, safflower, cottonseed, soybean, rapeseed, coconut and palm kernel), animal-sourced fats (e.g., beef tallow, pork tallow, lard, cod liver oil, fish oil), and mixtures thereof. Liquid diluents also include alkylated fatty acids (e.g., methylated, ethylated, butylated) wherein the fatty acids may be obtained by hydrolysis of glycerol esters from plant and animal sources, and can be purified by distillation. Typical liquid diluents are described in Marsden, *Solvents Guide,* 2nd Ed., Interscience, New York, 1950.

The solid and liquid compositions of the present invention often include one or more surfactants. When added to a liquid, surfactants (also known as "surface-active agents") generally modify, most often reduce, the surface tension of the liquid. Depending on the nature of the hydrophilic and lipophilic groups in a surfactant molecule, surfactants can be useful as wetting agents, dispersants, emulsifiers or defoaming agents.

Surfactants can be classified as nonionic, anionic or cationic. Nonionic surfactants useful for the present compositions include, but are not limited to: alcohol alkoxylates such as alcohol alkoxylates based on natural and synthetic alcohols (which may be branched or linear) and prepared from the alcohols and ethylene oxide, propylene oxide, butylene oxide or mixtures thereof; amine ethoxylates, alkanolamides and ethoxylated alkanolamides; alkoxylated triglycerides such as ethoxylated soybean, castor and rapeseed oils; alkylphenol alkoxylates such as octylphenol ethoxylates, nonylphenol ethoxylates, dinonyl phenol ethoxylates and dodecyl phenol ethoxylates (prepared from the phenols and ethylene oxide, propylene oxide, butylene oxide or mixtures thereof); block polymers prepared from ethylene oxide or propylene oxide and reverse block polymers where the terminal blocks are prepared from propylene oxide; ethoxylated fatty acids; ethoxylated fatty esters and oils; ethoxylated methyl esters; ethoxylated tristyrylphenol (including those prepared from ethylene oxide, propylene oxide, butylene oxide or mixtures thereof); fatty acid esters, glycerol esters, lanolin-based derivatives, polyethoxylate esters such as polyethoxylated sorbitan fatty acid esters, polyethoxylated sorbitol fatty acid esters and polyethoxylated glycerol fatty acid esters; other sorbitan derivatives such as sorbitan esters; polymeric surfactants such as random copolymers, block copolymers, alkyd peg (polyethylene glycol) resins, graft or comb polymers and star polymers; polyethylene glycols (pegs); polyethylene glycol fatty acid esters; silicone-based surfactants; and sugar-derivatives such as sucrose esters, alkyl polyglycosides and alkyl polysaccharides.

Useful anionic surfactants include, but are not limited to: alkylaryl sulfonic acids and their salts; carboxylated alcohol or alkylphenol ethoxylates; diphenyl sulfonate derivatives; lignin and lignin derivatives such as lignosulfonates; maleic or succinic acids or their anhydrides; olefin sulfonates; phosphate esters such as phosphate esters of alcohol alkoxylates, phosphate esters of alkylphenol alkoxylates and phosphate esters of styryl phenol ethoxylates; protein-based surfactants; sarcosine derivatives; styryl phenol ether sulfate; sulfates and sulfonates of oils and fatty acids; sulfates and sulfonates of ethoxylated alkylphenols; sulfates of alcohols; sulfates of ethoxylated alcohols; sulfonates of amines and amides such as N,N-alkyltaurates; sulfonates of benzene, cumene, toluene, xylene, and dodecyl and tridecylbenzenes; sulfonates of condensed naphthalenes; sulfonates of naphthalene and alkyl naphthalene; sulfonates of fractionated petroleum; sulfosuccinamates; and sulfosuccinates and their derivatives such as dialkyl sulfosuccinate salts.

Useful cationic surfactants include, but are not limited to: amides and ethoxylated amides; amines such as N-alkyl propanediamines, tripropylenetriamines and dipropylenetetramines, and ethoxylated amines, ethoxylated diamines and propoxylated amines (prepared from the amines and ethylene oxide, propylene oxide, butylene oxide or mixtures thereof); amine salts such as amine acetates and diamine salts; quaternary ammonium salts such as quaternary salts, ethoxylated quaternary salts and diquaternary salts; and amine oxides such as alkyldimethylamine oxides and bis-(2-hydroxyethyl)-alkylamine oxides.

Also useful for the present compositions are mixtures of nonionic and anionic surfactants or mixtures of nonionic and cationic surfactants. Nonionic, anionic and cationic surfactants and their recommended uses are disclosed in a variety of published references including *McCutcheon's Emulsifiers and Detergents*, annual American and International Editions published by McCutcheon's Division, The Manufacturing Confectioner Publishing Co.; Sisely and Wood, *Encyclopedia of Surface Active Agents*, Chemical Publ. Co., Inc., New York, 1964; and A. S. Davidson and B. Milwidsky, *Synthetic Detergents*, Seventh Edition, John Wiley and Sons, New York, 1987.

Compositions of this invention may also contain formulation auxiliaries and additives, known to those skilled in the art as formulation aids (some of which may be considered to also function as solid diluents, liquid diluents or surfactants). Such formulation auxiliaries and additives may control: pH (buffers), foaming during processing (antifoams such polyorganosiloxanes), sedimentation of active ingredients (suspending agents), viscosity (thixotropic thickeners), in-container microbial growth (antimicrobials), product freezing (antifreezes), color (dyes/pigment dispersions), wash-off (film formers or stickers), evaporation (evaporation retardants), and other formulation attributes. Film formers include, for example, polyvinyl acetates, polyvinyl acetate copolymers, polyvinylpyrrolidone-vinyl acetate copolymer, polyvinyl alcohols, polyvinyl alcohol copolymers and waxes. Examples of formulation auxiliaries and additives include those listed in *McCutcheon's Volume 2: Functional Materials*, annual International and North American editions published by McCutcheon's Division, The Manufacturing Confectioner Publishing Co.; and PCT Publication WO 03/024222.

The compound of Formula 1 and any other active ingredients are typically incorporated into the present compositions by dissolving the active ingredient in a solvent or by grinding in a liquid or dry diluent. Solutions, including emulsifiable concentrates, can be prepared by simply mixing the ingredients. If the solvent of a liquid composition intended for use as an emulsifiable concentrate is water-immiscible, an emulsifier is typically added to emulsify the active-containing solvent upon dilution with water. Active ingredient slurries, with particle diameters of up to 2,000 µm can be wet milled using media mills to obtain particles with average diameters below 3 µm. Aqueous slurries can be made into finished suspension concentrates (see, for example, U.S. Pat. No. 3,060,084) or further processed by spray drying to form water-dispersible granules. Dry formulations usually require dry milling processes, which produce average particle diameters in the 2 to 10 µm range. Dusts and powders can be prepared by blending and usually grinding (such as with a hammer mill or fluid-energy mill). Granules and pellets can be prepared by spraying the active material upon preformed granular carriers or by agglomeration techniques. See Browning, "Agglomeration", *Chemical Engineering*, Dec. 4, 1967, pp 147-48, *Perry's Chemical Engineer's Handbook*, 4th Ed., McGraw-Hill, New York, 1963, pages 8-57 and following, and WO 91/13546. Pellets can be prepared as described in U.S. Pat. No. 4,172,714. Water-dispersible and water-soluble granules can be prepared as taught in U.S. Pat. Nos. 4,144,050, 3,920,442 and DE 3,246,493. Tablets can be prepared as taught in U.S. Pat. Nos. 5,180,587, 5,232,701 and 5,208,030. Films can be prepared as taught in GB 2,095,558 and U.S. Pat. No. 3,299,566.

For further information regarding the art of formulation, see T. S. Woods, "The Formulator's Toolbox—Product Forms for Modern Agriculture" in *Pesticide Chemistry and Bioscience, The Food-Environment Challenge*, T. Brooks and T. R. Roberts, Eds., Proceedings of the 9th International Congress on Pesticide Chemistry, The Royal Society of Chemistry, Cambridge, 1999, pp. 120-133. See also U.S. Pat. No. 3,235,361, Col. 6, line 16 through Col. 7, line 19 and Examples 10-41; U.S. Pat. No. 3,309,192, Col. 5, line 43 through Col. 7, line 62 and Examples 8, 12, 15, 39, 41, 52, 53, 58, 132, 138-140, 162-164, 166, 167 and 169-182; U.S. Pat. No. 2,891,855, Col. 3, line 66 through Col. 5, line 17 and Examples 1-4; Klingman, *Weed Control as a Science*, John Wiley and Sons, Inc., New York, 1961, pp 81-96; Hance et al., *Weed Control Handbook*, 8th Ed., Blackwell Scientific Publications, Oxford, 1989; and *Developments in formulation technology*, PJB Publications, Richmond, UK, 2000.

In the following Examples, all percentages are by weight and all formulations are prepared in conventional ways. Compound numbers refer to compounds in Index Tables A-B. Without further elaboration, it is believed that one skilled in the art using the preceding description can utilize the present invention to its fullest extent. The following Examples are, therefore, to be construed as merely illustrative, and not limiting of the disclosure in any way whatsoever. Percentages are by weight except where otherwise indicated.

Example A

High Strength Concentrate

| | |
|---|---|
| Compound 1 | 98.5% |
| silica aerogel | 0.5% |
| synthetic amorphous fine silica | 1.0% |

Example B

Wettable Powder

| | |
|---|---|
| Compound 1 | 65.0% |
| dodecylphenol polyethylene glycol ether | 2.0% |
| sodium ligninsulfonate | 4.0% |
| sodium silicoaluminate | 6.0% |
| montmorillonite (calcined) | 23.0% |

Example C (i) Granule

| | |
|---|---|
| Compound 1 | 10.0% |
| attapulgite granules (low volatile matter, 0.71/0.30 mm; U.S.S. No. 25-50 sieves) | 90.0% |

Example D

Extruded Pellet

| | |
|---|---|
| Compound 1 | 25.0% |
| anhydrous sodium sulfate | 10.0% |
| crude calcium ligninsulfonate | 5.0% |
| sodium alkylnaphthalenesulfonate | 1.0% |
| calcium/magnesium bentonite | 59.0% |

Example E

Emulsifiable Concentrate

| | |
|---|---|
| Compound 1 | 10.0% |
| polyoxyethylene sorbitol hexoleate | 20.0% |
| $C_6$-$C_{10}$ fatty acid methyl ester | 70.0% |

Example F

Microemulsion

| | |
|---|---|
| Compound 1 | 5.0% |
| polyvinylpyrrolidone-vinyl acetate copolymer | 30.0% |
| alkylpolyglycoside | 30.0% |
| glyceryl monooleate | 15.0% |
| water | 20.0% |

Example G

Suspension Concentrate

| | |
|---|---|
| Compound 1 | 35% |
| butyl polyoxyethylene/polypropylene block copolymer | 4.0% |
| stearic acid/polyethylene glycol copolymer | 1.0% |
| styrene acrylic polymer | 1.0% |
| xanthan gum | 0.1% |
| propylene glycol | 5.0% |
| silicone based defoamer | 0.1% |
| 1,2-benzisothiazolin-3-one | 0.1% |
| Water | 53.7% |

Example H

Emulsion in Water

| | |
|---|---|
| Compound 1 | 10.0% |
| butyl polyoxyethylene/polypropylene block copolymer | 4.0% |
| stearic acid/polyethylene glycol copolymer | 1.0% |
| styrene acrylic polymer | 1.0% |
| xanthan gum | 0.1% |
| propylene glycol | 5.0% |
| silicone based defoamer | 0.1% |
| 1,2-benzisothiazolin-3-one | 0.1% |
| aromatic petroleum based hydrocarbon | 20.0 |
| Water | 58.7% |

Example I

Oil Dispersion

| | |
|---|---|
| Compound 1 | 25% |
| polyoxyethylene sorbitol hexaoleate | 15% |
| organically modified bentonite clay | 2.5% |
| fatty acid methyl ester | 57.5% |

The present disclosure also includes Examples A through I above except "Compound 1" is separately replaced with "Compound 2", "Compound 3", "Compound 4", "Compound 5", "Compound 6", "Compound 7", "Compound 8", "Compound 9", "Compound 10", "Compound 11", "Compound 12", "Compound 13" and "Compound 14".

Test results indicate that the compounds of the present invention are highly active preemergent and/or postemergent herbicides and/or plant growth regulants. The compounds of the inention generally show highest activity for postemergence weed control (i.e. applied after weed seedlings emerge from the soil) and preemergence weed control (i.e. applied before weed seedlings emerge from the soil). Many of them have utility for broad-spectrum pre- and/or postemergence weed control in areas where complete control of all vegetation is desired such as around fuel storage tanks, industrial storage areas, parking lots, drive-in theaters, air fields, river banks, irrigation and other waterways, around billboards and highway and railroad structures. Many of the compounds of this invention, by virtue of selective metabolism in crops versus weeds, or by selective activity at the locus of physiological inhibition in crops and weeds, or by selective placement on or within the environment of a mixture of crops and weeds, are useful for the selective control of grass and broadleaf weeds within a crop/weed mixture. One skilled in the art will recognize that the preferred combination of these selectivity factors within a compound or group of compounds can readily be determined by performing routine biological and/or biochemical assays. Compounds of this invention may show tolerance to important agronomic crops including, but is not limited to, alfalfa, barley, cotton, wheat, rape, sugar beets, corn (maize), sorghum, soybeans, rice, oats, peanuts, vegetables, tomato, potato, perennial plantation crops including coffee, cocoa, oil palm, rubber, sugarcane, citrus, grapes, fruit trees, nut trees, banana, plantain, pineapple, hops, tea and forests such as eucalyptus and conifers (e.g., loblolly pine), and turf species (e.g., Kentucky bluegrass, St. Augustine grass, Kentucky fescue and Bermuda grass). Compounds of this invention can be used in crops genetically transformed or bred to incorporate resistance to herbicides, express proteins toxic to invertebrate pests (such as Bacillus thuringiensis toxin), and/or express other useful traits. Those skilled in the art will appreciate that not all compounds are equally effective against all weeds. Alternatively, the subject compounds are useful to modify plant growth.

As the compounds of the invention have preemergent and postemergent herbicidal activity, to control undesired vegetation by killing or injuring the vegetation or reducing its growth, the compounds can be usefully applied by a variety of methods involving contacting a herbicidally effective amount of a compound of the invention, or a composition comprising said compound and at least one of a surfactant, a solid diluent or a liquid diluent, to the foliage or other part of the undesired vegetation or to the environment of the undesired vegetation such as the soil or water in which the undesired vegetation is growing or which surrounds the seed or other propagule of the undesired vegetation.

A herbicidally effective amount of the compounds of this invention is determined by a number of factors. These factors include: formulation selected, method of application, amount and type of vegetation present, growing conditions, etc. In general, a herbicidally effective amount of compounds of this invention is about 0.001 to 20 kg/ha with a preferred range of about 0.004 to 1 kg/ha. One skilled in the art can easily determine the herbicidally effective amount necessary for the desired level of weed control.

In one common embodiment, a compound of the invention is applied, typically in a formulated composition, to a locus comprising desired vegetation (e.g., crops) and undesired vegetation (i.e. weeds), both of which may be seeds, seedlings and/or larger plants, in contact with a growth medium (e.g., soil). In this locus, a composition comprising a compound of the invention can be directly applied to a plant or a part thereof, particularly of the undesired vegetation, and/or to the growth medium in contact with the plant.

Plant varieties and cultivars of the desired vegetation in the locus treated with a compound of the invention can be obtained by conventional propagation and breeding methods or by genetic engineering methods. Genetically modified plants (transgenic plants) are those in which a heterologous gene (transgene) has been stably integrated into the plant's genome. A transgene that is defined by its particular location in the plant genome is called a transformation or transgenic event.

Genetically modified plant cultivars in the locus which can be treated according to the invention include those that are resistant against one or more biotic stresses (pests such as nematodes, insects, mites, fungi, etc.) or abiotic stresses (drought, cold temperature, soil salinity, etc.), or that contain other desirable characteristics. Plants can be genetically modified to exhibit traits of, for example, herbicide tolerance, insect-resistance, modified oil profiles or drought tolerance. Useful genetically modified plants containing single gene transformation events or combinations of transformation events are listed in Exhibit C. Additional information for the genetic modifications listed in Exhibit C can be obtained from publicly available databases maintained, for example, by the U.S. Department of Agriculture.

The following abbreviations, T1 through T37, are used in Exhibit C for traits. A "-" means the entry is not available; "tol." means "tolerance" and "res." means resistance.

| Trait | Description |
|---|---|
| T1 | Glyphosate tol. |
| T2 | High lauric acid oil |
| T3 | Glufosinate tol. |
| T4 | Phytate breakdown |
| T5 | Oxynil tol. |
| T6 | Disease res. |
| T7 | Insect res. |
| T9 | Modified flower color |
| T11 | ALS Herbicide tol. |
| T12 | Dicamba tol. |
| T13 | Anti-allergy |
| T14 | Salt tol. |
| T15 | Cold tol. |
| T16 | Imidazolinone herb. tol. |
| T17 | Modified alpha-amylase |
| T18 | Pollination control |
| T19 | 2,4-D tol. |
| T20 | Increased lysine |
| T21 | Drought tol. |
| T22 | Delayed ripening/senescence |
| T23 | Modified product quality |
| T24 | High cellulose |
| T25 | Modified starch/carbohydrate |
| T26 | Insect & disease resist. |
| T27 | High tryptophan |
| T28 | Erect leaves semidwarf |
| T29 | Semidwarf |
| T30 | Low iron tol. |
| T31 | Modified oil/fatty acid |
| T32 | HPPD tol. |
| T33 | High oil |
| T34 | Aryloxyalkanoate tol. |
| T35 | Mesotrione tol. |
| T36 | Reduced nicotine |
| T37 | Modified product |

Exhibit C

| Crop | Event Name | Event Code | Trait(s) | Gene(s) |
|---|---|---|---|---|
| Alfalfa | J101 | MON-00101-8 | T1 | cp4 epsps (aroA:CP4) |
| Alfalfa | J163 | MON-ØØ163-7 | T1 | cp4 epsps (aroA:CP4) |
| Canola* | 23-18-17 (Event 18) | CGN-89465-2 | T2 | te |
| Canola* | 23-198 (Event 23) | CGN-89465-2 | T2 | te |
| Canola* | 61061 | DP-Ø61Ø61-7 | T1 | gat4621 |
| Canola* | 73496 | DP-Ø73496-4 | T1 | gat4621 |
| Canola* | GT200 (RT200) | MON-89249-2 | T1 | cp4 epsps (aroA:CP4); goxv247 |
| Canola* | GT73 (RT73) | MON-ØØØ73-7 | T1 | cp4 epsps (aroA:CP4); goxv247 |
| Canola* | HCN10 (Topas 19/2) | — | T3 | bar |

| Crop | Event Name | Event Code | Trait(s) | Gene(s) |
| --- | --- | --- | --- | --- |
| Canola* | HCN28 (T45) | ACS-BNØØ8-2 | T3 | pat (syn) |
| Canola* | HCN92 (Topas 19/2) | ACS-BNØØ7-1 | T3 | bar |
| Canola* | MON88302 | MON-883Ø2-9 | T1 | cp4 epsps (aroA:CP4) |
| Canola* | MPS961 | — | T4 | phyA |
| Canola* | MPS962 | — | T4 | phyA |
| Canola* | MPS963 | — | T4 | phyA |
| Canola* | MPS964 | — | T4 | phyA |
| Canola* | MPS965 | — | T4 | phyA |
| Canola* | MS1 (B91-4) | ACS-BNØØ4-7 | T3 | bar |
| Canola* | MS8 | ACS-BNØØ5-8 | T3 | bar |
| Canola* | OXY-235 | ACS-BNØ11-5 | T5 | bxn |
| Canola* | PHY14 | — | T3 | bar |
| Canola* | PHY23 | — | T3 | bar |
| Canola* | PHY35 | — | T3 | bar |
| Canola* | PHY36 | — | T3 | bar |
| Canola* | RF1 (B93-101) | ACS-BNØØ1-4 | T3 | bar |
| Canola* | RF2 (B94-2) | ACS-BNØØ2-5 | T3 | bar |
| Canola* | RF3 | ACS-BNØØ3-6 | T3 | bar |
| Bean | EMBRAPA 5.1 | EMB-PV051-1 | T6 | ac1 (sense and antisense) |
| Brinjal # | EE-1 | — | T7 | cry1Ac |
| Cotton | 19-51a | DD-Ø1951A-7 | T11 | S4-HrA |
| Cotton | 281-24-236 | DAS-24236-5 | T3, T7 | pat (syn); cry1F |
| Cotton | 3006-210-23 | DAS-21Ø23-5 | T3, T7 | pat (syn); cry1Ac |
| Cotton | 31707 | — | T5, T7 | bxn; cry1Ac |
| Cotton | 31803 | — | T5, T7 | bxn; cry1Ac |
| Cotton | 31807 | — | T5, T7 | bxn; cry1Ac |
| Cotton | 31808 | — | T5, T7 | bxn; cry1Ac |
| Cotton | 42317 | — | T5, T7 | bxn; cry1Ac |
| Cotton | BNLA-601 | — | T7 | cry1Ac |
| Cotton | BXN10211 | BXN10211-9 | T5 | bxn; cry1Ac |
| Cotton | BXN10215 | BXN10215-4 | T5 | bxn; cry1Ac |
| Cotton | BXN10222 | BXN10222-2 | T5 | bxn; cry1Ac |
| Cotton | BXN10224 | BXN10224-4 | T5 | bxn; cry1Ac |
| Cotton | COT102 | SYN-IR102-7 | T7 | vip3A(a) |
| Cotton | COT67B | SYN-IR67B-1 | T7 | cry1Ab |
| Cotton | COT202 | — | T7 | vip3A |
| Cotton | Event 1 | — | T7 | cry1Ac |
| Cotton | GMF Cry1A | GTL-GMF311-7 | T7 | cry1Ab-Ac |
| Cotton | GHB119 | BCS-GH005-8 | T7 | cry2Ae |
| Cotton | GHB614 | BCS-GH002-5 | T1 | 2mepsps |
| Cotton | GK12 | — | T7 | cry1Ab-Ac |
| Cotton | LLCotton25 | ACS-GH001-3 | T3 | bar |
| Cotton | MLS 9124 | — | T7 | cry1C |
| Cotton | MON1076 | MON-89924-2 | T7 | cry1Ac |
| Cotton | MON1445 | MON-01445-2 | T1 | cp4 epsps (aroA:CP4) |
| Cotton | MON15985 | MON-15985-7 | T7 | cry1Ac; cry2Ab2 |
| Cotton | MON1698 | MON-89383-1 | T7 | cp4 epsps (aroA:CP4) |
| Cotton | MON531 | MON-00531-6 | T7 | cry1Ac |
| Cotton | MON757 | MON-00757-7 | T7 | cry1Ac |
| Cotton | MON88913 | MON-88913-8 | T1 | cp4 epsps (aroA:CP4) |
| Cotton | Nqwe Chi 6 Bt | — | T7 | — |
| Cotton | SKG321 | — | T7 | cry1A; CpTI |
| Cotton | T303-3 | BCS-GH003-6 | T3, T7 | cry1Ab; bar |
| Cotton | T304-40 | BCS-GH004-7 | T3, T7 | cry1Ab; bar |
| Cotton | CE43-67B | — | T7 | cry1Ab |
| Cotton | CE46-02A | — | T7 | cry1Ab |
| Cotton | CE44-69D | — | T7 | cry1Ab |
| Cotton | 1143-14A | — | T7 | cry1Ab |
| Cotton | 1143-51B | — | T7 | cry1Ab |
| Cotton | T342-142 | — | T7 | cry1Ab |
| Cotton | PV-GHGT07 (1445) | — | T1 | cp4 epsps (aroA:CP4) |
| Cotton | EE-GH3 | — | T1 | mepsps |
| Cotton | EE-GH5 | — | T7 | cry1Ab |
| Cotton | MON88701 | MON-88701-3 | T3, T12 | Modified dmo; bar |
| Cotton | OsCr11 | — | T13 | Modified Cry j |
| Flax | FP967 | CDC-FL001-2 | T11 | als |
| Lentil | RH44 | — | T16 | als |
| Maize | 3272 | SYN-E3272-5 | T17 | amy797E |
| Maize | 5307 | SYN-05307-1 | T7 | ecry3.1Ab |
| Maize | 59122 | DAS-59122-7 | T3, T7 | cry34Ab1; cry35Ab1; pat |
| Maize | 676 | PH-000676-7 | T3, T18 | pat; dam |
| Maize | 678 | PH-000678-9 | T3, T18 | pat; dam |
| Maize | 680 | PH-000680-2 | T3, T18 | pat; dam |
| Maize | 98140 | DP-098140-6 | T1, T11 | gat4621; zm-hra |
| Maize | Bt10 | — | T3, T7 | cry1Ab; pat |
| Maize | Bt176 (176) | SYN-EV176-9 | T3, T7 | cry1Ab; bar |
| Maize | BVLA430101 | — | T4 | phyA2 |

-continued

| Crop | Event Name | Event Code | Trait(s) | Gene(s) |
|---|---|---|---|---|
| Maize | CBH-351 | ACS-ZM004-3 | T3, T7 | cry9C; bar |
| Maize | DAS40278-9 | DAS40278-9 | T19 | aad-1 |
| Maize | DBT418 | DKB-89614-9 | T3, T7 | cry1Ac; pinII; bar |
| Maize | DLL25 (B16) | DKB-89790-5 | T3 | bar |
| Maize | GA21 | MON-00021-9 | T1 | mepsps |
| Maize | GG25 | — | T1 | mepsps |
| Maize | GJ11 | — | T1 | mepsps |
| Maize | Fl117 | — | T1 | mepsps |
| Maize | GAT-ZM1 | — | T3 | pat |
| Maize | LY038 | REN-00038-3 | T20 | cordapA |
| Maize | MIR162 | SYN-IR162-4 | T7 | vip3Aa20 |
| Maize | MIR604 | SYN-IR604-5 | T7 | mcry3A |
| Maize | MON801 (MON80100) | MON801 | T1, T7 | cry1Ab; cp4 epsps (aroA:CP4); goxv247 |
| Maize | MON802 | MON-80200-7 | T1, T7 | cry1Ab; cp4 epsps (aroA:CP4); goxv247 |
| Maize | MON809 | PH-MON-809-2 | T1, T7 | cry1Ab; cp4 epsps (aroA:CP4); goxv247 |
| Maize | MON810 | MON-00810-6 | T1, T7 | cry1Ab; cp4 epsps (aroA:CP4); goxv247 |
| Maize | MON832 | — | T1 | cp4 epsps (aroA:CP4); goxv247 |
| Maize | MON863 | MON-00863-5 | T7 | cry3Bb1 |
| Maize | MON87427 | MON-87427-7 | T1 | cp4 epsps (aroA:CP4) |
| Maize | MON87460 | MON-87460-4 | T21 | cspB |
| Maize | MON88017 | MON-88017-3 | T1, T7 | cry3Bb1; cp4 epsps (aroA:CP4) |
| Maize | MON89034 | MON-89034-3 | T7 | cry2Ab2; cry1A.105 |
| Maize | MS3 | ACS-ZM001-9 | T3, T18 | bar; barnase |
| Maize | MS6 | ACS-ZM005-4 | T3, T18 | bar; barnase |
| Maize | NK603 | MON-00603-6 | T1 | cp4 epsps (aroA:CP4) |
| Maize | T14 | ACS-ZM002-1 | T3 | pat (syn) |
| Maize | T25 | ACS-ZM003-2 | T3 | pat (syn) |
| Maize | TC1507 | DAS-01507-1 | T3, T7 | cry1Fa2; pat |
| Maize | TC6275 | DAS-06275-8 | T3, T7 | mocry1F; bar |
| Maize | VIP1034 | — | T3, T7 | vip3A; pat |
| Maize | 43A47 | DP-043A47-3 | T3, T7 | cry1F; cry34Ab1; cry35Ab1; pat |
| Maize | 40416 | DP-040416-8 | T3, T7 | cry1F; cry34Ab1; cry35Ab1; pat |
| Maize | 32316 | DP-032316-8 | T3, T7 | cry1F; cry34Ab1; cry35Ab1; pat |
| Maize | 4114 | DP-004114-3 | T3, T7 | cry1F; cry34Ab1; cry35Ab1; pat |
| Melon | Melon A | — | T22 | sam-k |
| Melon | Melon B | — | T22 | sam-k |
| Papaya | 55-1 | CUH-CP551-8 | T6 | prsv cp |
| Papaya | 63-1 | CUH-CP631-7 | T6 | prsv cp |
| Papaya | Huanong No. 1 | — | T6 | prsv rep |
| Papaya | X17-2 | UFL-X17CP-6 | T6 | prsv cp |
| Plum | C-5 | ARS-PLMC5-6 | T6 | ppv cp |
| Canola** | ZSR500 | — | T1 | cp4 epsps (aroA:CP4); goxv247 |
| Canola** | ZSR502 | — | T1 | cp4 epsps (aroA:CP4); goxv247 |
| Canola** | ZSR503 | — | T1 | cp4 epsps (aroA:CP4); goxv247 |
| Rice | 7Crp#242-95-7 | — | T13 | 7crp |
| Rice | 7Crp#10 | — | T13 | 7crp |
| Rice | GM Shanyou 63 | — | T7 | cry1Ab; cry1Ac |
| Rice | Huahui-1/TT51-1 | — | T7 | cry1Ab; cry1Ac |
| Rice | LLRICE06 | ACS-OS001-4 | T3 | bar |
| Rice | LLRICE601 | BCS-OS003-7 | T3 | bar |
| Rice | LLRICE62 | ACS-OS002-5 | T3 | bar |
| Rice | Tarom molaii + cry1Ab | — | T7 | cry1Ab (truncated) |
| Rice | GAT-OS2 | — | T3 | bar |
| Rice | GAT-OS3 | — | T3 | bar |
| Rice | PE-7 | — | T7 | Cry1Ac |
| Rice | 7Crp#10 | — | T13 | 7crp |
| Rice | KPD627-8 | — | T27 | OASA1D |
| Rice | KPD722-4 | — | T27 | OASA1D |
| Rice | KA317 | — | T27 | OASA1D |
| Rice | HW5 | — | T27 | OASA1D |
| Rice | HW1 | — | T27 | OASA1D |
| Rice | B-4-1-18 | — | T28 | Δ OsBRI1 |
| Rice | G-3-3-22 | — | T29 | OSGA2ox1 |
| Rice | AD77 | — | T6 | DEF |
| Rice | AD51 | — | T6 | DEF |
| Rice | AD48 | — | T6 | DEF |
| Rice | AD41 | — | T6 | DEF |
| Rice | 13pNasNa800725atAprt1 | — | T30 | HvNAS1; HvNAAT-A; APRT |
| Rice | 13pAprt1 | — | T30 | APRT |
| Rice | gHvNAS1-gHvNAAT-1 | — | T30 | HvNAS1; HvNAAT-A; HvNAAT-B |
| Rice | gHvIDS3-1 | — | T30 | HvIDS3 |
| Rice | gHvNAAT1 | — | T30 | HvNAAT-A; HvNAAT-B |
| Rice | gHvNAS1-1 | — | T30 | HvNAS1 |

-continued

| Crop | Event Name | Event Code | Trait(s) | Gene(s) |
| --- | --- | --- | --- | --- |
| Rice | NIA-OS006-4 | — | T6 | WRKY45 |
| Rice | NIA-OS005-3 | — | T6 | WRKY45 |
| Rice | NIA-OS004-2 | — | T6 | WRKY45 |
| Rice | NIA-OS003-1 | — | T6 | WRKY45 |
| Rice | NIA-OS002-9 | — | T6 | WRKY45 |
| Rice | NIA-OS001-8 | — | T6 | WRKY45 |
| Rice | OsCrl1 | — | T13 | Modified Cry j |
| Rice | 17053 | — | T1 | cp4 epsps (aroA:CP4) |
| Rice | 17314 | — | T1 | cp4 epsps (aroA:CP4) |
| Rose | WKS82/130-4-1 | IFD-52401-4 | T9 | 5AT; bp40 (f3'5'h) |
| Rose | WKS92/130-9-1 | IFD-52901-9 | T9 | 5AT; bp40 (f3'5'h) |
| Soybean | 260-05 (G94-1, G94-19, G168) | — | T9 | gm-fad2-1 (silencing locus) |
| Soybean | A2704-12 | ACS-GM005-3 | T3 | pat |
| Soybean | A2704-21 | ACS-GM004-2 | T3 | pat |
| Soybean | A5547-127 | ACS-GM006-4 | T3 | pat |
| Soybean | A5547-35 | ACS-GM008-6 | T3 | pat |
| Soybean | CV127 | BPS-CV127-9 | T16 | csr1-2 |
| Soybean | DAS68416-4 | DAS68416-4 | T3 | pat |
| Soybean | DP305423 | DP-305423-1 | T11, T31 | gm-fad2-1 (silencing locus); gm-hra |
| Soybean | DP356043 | DP-356043-5 | T1, T31 | gm-fad2-1 (silencing locus); gat4601 |
| Soybean | FG72 | MST-FG072-3 | T32, T1 | 2mepsps; hppdPF W336 |
| Soybean | GTS 40-3-2 (40-3-2) | MON-04032-6 | T1 | cp4 epsps (aroA:CP4) |
| Soybean | GU262 | ACS-GM003-1 | T3 | pat |
| Soybean | MON87701 | MON-87701-2 | T7 | cry1Ac |
| Soybean | MON87705 | MON-87705-6 | T1, T31 | fatb1-A (sense & antisense); fad2-1A (sense & antisense); cp4 epsps (aroA:CP4) |
| Soybean | MON87708 | MON-87708-9 | T1, T12 | dmo; cp4 epsps (aroA:CP4) |
| Soybean | MON87769 | MON-87769-7 | T1, T31 | Pj.D6D; Nc.Fad3; cp4 epsps (aroA:CP4) |
| Soybean | MON89788 | MON-89788-1 | T1 | cp4 epsps (aroA:CP4) |
| Soybean | W62 | ACS-GM002-9 | T3 | bar |
| Soybean | W98 | ACS-GM001-8 | T3 | bar |
| Soybean | MON87754 | MON-87754-1 | T33 | dgat2A |
| Soybean | DAS21606 | DAS-21606 | T34, T3 | Modified aad-12; pat |
| Soybean | DAS44406 | DAS-44406-6 | T1, T3, T34 | Modified aad-12; 2mepsps; pat |
| Soybean | SYHT04R | SYN-0004R-8 | T35 | Modified avhppd |
| Soybean | 9582.814.19.1 | — | T3, T7 | cry1Ac, cry1F, PAT |
| Squash | CZW3 | SEM-ØCZW3-2 | T6 | cmv cp, zymv cp, wmv cp |
| Squash | ZW20 | SEM-0ZW20-7 | T6 | zymv cp, wmv cp |
| Sugar Beet | GTSB77 (T9100152) | SY-GTSB77-8 | T1 | cp4 epsps (aroA:CP4); goxv247 |
| Sugar Beet | H7-1 | KM-000H71-4 | T1 | cp4 epsps (aroA:CP4) |
| Sugar Beet | T120-7 | ACS-BV001-3 | T3 | pat |
| Sugar Beet | T227-1 | — | T1 | cp4 epsps (aroA:CP4) |
| Sugarcane | NXI-1T | — | T21 | EcbetA |
| Sunflower | X81359 | — | T16 | als |
| Pepper | PK-SP01 | — | T6 | cmv cp |
| Tobacco | C/F/93/08-02 | — | T5 | bxn |
| Tobacco | Vector 21-41 | — | T36 | NtQPT1 (antisense) |
| Sunflower | X81359 | — | T16 | als |
| Wheat | MON71800 | MON-718ØØ-3 | T1 | cp4 epsps (aroA:CP4) |

*Argentine (*Brassica napus*),
**Polish (*B. rapa*),
Eggplant

Although most typically, compounds of the invention are used to control undesired vegetation, contact of desired vegetation in the treated locus with compounds of the invention may result in super-additive or synergistic effects with genetic traits in the desired vegetation, including traits incorporated through genetic modification. For example, resistance to phytophagous insect pests or plant diseases, tolerance to biotic/abiotic stresses or storage stability may be greater than expected from the genetic traits in the desired vegetation.

Compounds of this invention can also be mixed with one or more other biologically active compounds or agents including herbicides, herbicide safeners, fungicides, insecticides, nematocides, bactericides, acaricides, growth regulators such as insect molting inhibitors and rooting stimulants, chemosterilants, semiochemicals, repellents, attractants, pheromones, feeding stimulants, plant nutrients, other biologically active compounds or entomopathogenic bacteria, virus or fungi to form a multi-component pesticide giving an even broader spectrum of agricultural protection. Mixtures of the compounds of the invention with other herbicides can broaden the spectrum of activity against additional weed species, and suppress the proliferation of any resistant biotypes. Thus the present invention also pertains to a composition comprising a compound of Formula 1 (in a herbicidally effective amount) and at least one additional biologically active compound or agent (in a biologically effective amount) and can further comprise at least one of a surfactant, a solid diluent or a liquid diluent. The other biologically active compounds or agents can be formulated in compositions comprising at least one of a surfactant, solid or liquid diluent. For mixtures of the present invention, one or more other biologically active compounds or agents can be formulated together with a compound of Formula 1, to form a premix, or one or more other biologically active compounds or agents can be formulated separately from the compound of Formula 1, and the formulations combined together before application (e.g., in a spray tank) or, alternatively, applied in succession.

A mixture of one or more of the following herbicides with a compound of this invention may be particularly useful for weed control: acetochlor, acifluorfen and its sodium salt, aclonifen, acrolein (2-propenal), alachlor, alloxydim, ametryn, amicarbazone, amidosulfuron, aminocyclopyrachlor and its esters (e.g., methyl, ethyl) and salts (e.g., sodium, potassium), aminopyralid, amitrole, ammonium sulfamate, anilofos, asulam, atrazine, azimsulfuron, beflubutamid, benazolin, benazolin-ethyl, bencarbazone, benfluralin, benfuresate, bensulfuron-methyl, bensulide, bentazone, benzobicyclon, benzofenap, bicyclopyrone, bifenox, bilanafos, bispyribac and its sodium salt, bromacil, bromobutide, bromofenoxim, bromoxynil, bromoxynil octanoate, butachlor, butafenacil, butamifos, butralin, butroxydim, butylate, cafenstrole, carbetamide, carfentrazone-ethyl, catechin, chlomethoxyfen, chloramben, chlorbromuron, chlorflurenol-methyl, chloridazon, chlorimuron-ethyl, chlorotoluron, chlorpropham, chlorsulfuron, chlorthal-dimethyl, chlorthiamid, cinidon-ethyl, cinmethylin, cinosulfuron, clacyfos, clefoxydim, clethodim, clodinafop-propargyl, clomazone, clomeprop, clopyralid, clopyralid-olamine, cloransulam-methyl, cumyluron, cyanazine, cycloate, cyclopyrimorate, cyclosulfamuron, cycloxydim, cyhalofop-butyl, 2,4-D and its butotyl, butyl, isoctyl and isopropyl esters and its dimethylammonium, diolamine and trolamine salts, daimuron, dalapon, dalapon-sodium, dazomet, 2,4-DB and its dimethylammonium, potassium and sodium salts, desmedipham, desmetryn, dicamba and its diglycolammonium, dimethylammonium, potassium and sodium salts, dichlobenil, dichlorprop, diclofop-methyl, diclosulam, difenzoquat metilsulfate, diflufenican, diflufenzopyr, dimefuron, dimepiperate, dimethachlor, dimethametryn, dimethenamid, dimethenamid-P, dimethipin, dimethylarsinic acid and its sodium salt, dinitramine, dinoterb, diphenamid, diquat dibromide, dithiopyr, diuron, DNOC, endothal, EPTC, esprocarb, ethalfluralin, ethametsulfuron-methyl, ethiozin, ethofumesate, ethoxyfen, ethoxysulfuron, etobenzanid, fenoxaprop-ethyl, fenoxaprop-P-ethyl, fenoxasulfone, fenquinotrione, fentrazamide, fenuron, fenuron-TCA, flamprop-methyl, flamprop-M-isopropyl, flamprop-M-methyl, flazasulfuron, florasulam, fluazifop-butyl, fluazifop-P-butyl, fluazolate, flucarbazone, flucetosulfuron, fluchloralin, flufenacet, flufenpyr, flufenpyr-ethyl, flumetsulam, flumiclorac-pentyl, flumioxazin, fluometuron, fluoroglycofen-ethyl, flupoxam, flupyrsulfuron-methyl and its sodium salt, flurenol, flurenol-butyl, fluridone, flurochloridone, fluroxypyr, flurtamone, fluthiacet-methyl, fomesafen, foramsulfuron, fosamine-ammonium, glufosinate, glufosinate-ammonium, glufosinate-P, glyphosate and its salts such as ammonium, isopropylammonium, potassium, sodium (including sesquisodium) and trimesium (alternatively named sulfosate), halauxifen, halauxifen-methyl, halosulfuron-methyl, haloxyfop-etotyl, haloxyfop-methyl, hexazinone, hydantocidin, imazamethabenz-methyl, imazamox, imazapic, imazapyr, imazaquin, imazaquin-ammonium, imazethapyr, imazethapyr-ammonium, imazosulfuron, indanofan, indaziflam, iofensulfuron, iodosulfuron-methyl, ioxynil, ioxynil octanoate, ioxynil-sodium, ipfencarbazone, isoproturon, isouron, isoxaben, isoxaflutole, isoxachlortole, lactofen, lenacil, linuron, maleic hydrazide, MCPA and its salts (e.g., MCPA-dimethylammonium, MCPA-potassium and MCPA-sodium), esters (e.g., MCPA-2-ethylhexyl, MCPA-butotyl) and thioesters (e.g., MCPA-thioethyl), MCPB and its salts (e.g., MCPB-sodium) and esters (e.g., MCPB-ethyl), mecoprop, mecoprop-P, mefenacet, mefluidide, mesosulfuron-methyl, mesotrione, metam-sodium, metamifop, metamitron, metazachlor, metazosulfuron, methabenzthiazuron, methylarsonic acid and its calcium, monoammonium, monosodium and disodium salts, methyldymron, metobenzuron, metobromuron, metolachlor, S-metolachlor, metosulam, metoxuron, metribuzin, metsulfuron-methyl, molinate, monolinuron, naproanilide, napropamide, napropamide-M, naptalam, neburon, nicosulfuron, norflurazon, orbencarb, orthosulfamuron, oryzalin, oxadiargyl, oxadiazon, oxasulfuron, oxaziclomefone, oxyfluorfen, paraquat dichloride, pebulate, pelargonic acid, pendimethalin, penoxsulam, pentanochlor, pentoxazone, perfluidone, pethoxamid, pethoxyamid, phenmedipham, picloram, picloram-potassium, picolinafen, pinoxaden, piperophos, pretilachlor, primisulfuron-methyl, prodiamine, profoxydim, prometon, prometryn, propachlor, propanil, propaquizafop, propazine, propham, propisochlor, propoxycarbazone, propyrisulfuron, propyzamide, prosulfocarb, prosulfuron, pyraclonil, pyraflufen-ethyl, pyrasulfotole, pyrazogyl, pyrazolynate, pyrazoxyfen, pyrazosulfuron-ethyl, pyribenzoxim, pyributicarb, pyridate, pyriftalid, pyriminobac-methyl, pyrimisulfan, pyrithiobac, pyrithiobac-sodium, pyroxasulfone, pyroxsulam, quinclorac, quinmerac, quinoclamine, quizalofop-ethyl, quizalofop-P-ethyl, quizalofop-P-tefuryl, rimsulfuron, saflufenacil, sethoxydim, siduron, simazine, simetryn, sulcotrione, sulfentrazone, sulfometuron-methyl, sulfosulfuron, 2,3,6-TBA, TCA, TCA-sodium, tebutam, tebuthiuron, tefuryltrione, tembotrione, tepraloxydim, terbacil, terbumeton, terbuthylazine, terbutryn, thenylchlor, thiazopyr, thiencarbazone, thifensulfuron-methyl, thiobencarb, tiafenacil, tiocarbazil, tolpyralate, topramezone, tralkoxydim, triallate, triafamone, triasulfuron, triaziflam, tribenuron-methyl, triclopyr, triclopyr-butotyl, triclopyr-triethylammonium, tridiphane, trietazine, trifloxysulfuron, trifludimoxazin, trifluralin, triflusulfuron-methyl, tritosulfuron, vernolate, 3-(2-chloro-3,6-difluorophenyl)-4-hydroxy-1-methyl-1,5-naphthyridin-2(1H)-one, 5-chloro-3-[(2-hydroxy-6-oxo-1-cyclohexen-1-yl)carbonyl]-1-(4-methoxyphenyl)-2(1H)-quinoxalinone, 2-chloro-N-(1-methyl-1H-tetrazol-5-yl)-6-(trifluoromethyl)-3-pyridinecarboxamide, 7-(3,5-dichloro-4-pyridinyl)-5-(2,2-difluoroethyl)-8-hydroxypyrido[2,3-b]pyrazin-6(5H)-one), 4-(2,6-diethyl-4-methylphenyl)-5-hydroxy-2,6-dimethyl-3(2H)-pyridazinone), 5-[[(2,6-difluorophenyl)methoxy]methyl]-4,5-dihydro-5-methyl-3-(3-methyl-2-thienyl)isoxazole (previously methioxolin), 4-(4-fluorophenyl)-6-[(2-hydroxy-6-oxo-1-cyclohexen-1-yl)carbonyl]-2-methyl-1,2,4-triazine-3,5(2H,4H)-dione, methyl 4-amino-3-chloro-6-(4-chloro-2-fluoro-3-methoxyphenyl)-5-fluoro-2-pyridinecarboxylate, 2-methyl-3-(methylsulfonyl)-N-(1-methyl-1H-tetrazol-5-yl)-4-(trifluoromethyl)benzamide and 2-methyl-N-(4-methyl-1,2,5-oxadiazol-3-yl)-3-(methylsulfinyl)-4-(trifluoromethyl)benzamide. Other herbicides also include bioherbicides such as *Alternaria destruens* Simmons, *Colletotrichum gloeosporiodes* (Penz.) Penz. & Sacc., *Drechsiera monoceras* (MTB-951), *Myrothecium verrucaria* (Albertini & Schweinitz) Ditmar: Fries, *Phytophthora palmivora* (Butl.) Butl. and *Puccinia thlaspeos* Schub.

Compounds of this invention can also be used in combination with plant growth regulators such as aviglycine, N-(phenylmethyl)-1H-purin-6-amine, epocholeone, gibberellic acid, gibberellin $A_4$ and $A_7$, harpin protein, mepiquat chloride, prohexadione calcium, prohydrojasmon, sodium nitrophenolate and trinexapac-methyl, and plant growth modifying organisms such as *Bacillus cereus* strain BP01.

General references for agricultural protectants (i.e. herbicides, herbicide safeners, insecticides, fungicides, nematocides, acaricides and biological agents) include *The Pesticide Manual*, 13th *Edition*, C. D. S. Tomlin, Ed., British Crop Protection Council, Famham, Surrey, U.K., 2003 and *The BioPesticide Manual, 2nd Edition*, L. G. Copping, Ed., British Crop Protection Council, Farnham, Surrey, U.K., 2001.

For embodiments where one or more of these various mixing partners are used, the mixing partners are typically used in the amounts similar to amounts customary when the mixture partners are used alone. More particularly in mixtures, active ingredients are often applied at an application rate between one-half and the full application rate specified on product labels for use of active ingredient alone. These amounts are listed in references such as *The Pesticide Manual* and *The BioPesticide Manual*. The weight ratio of these various mixing partners (in total) to the compound of Formula 1 is typically between about 1:3000 and about 3000:1. Of note are weight ratios between about 1:300 and about 300:1 (for example ratios between about 1:30 and about 30:1). One skilled in the art can easily determine through simple experimentation the biologically effective amounts of active ingredients necessary for the desired spectrum of biological activity. It will be evident that including these additional components may expand the spectrum of weeds controlled beyond the spectrum controlled by the compound of Formula 1 alone.

In certain instances, combinations of a compound of this invention with other biologically active (particularly herbicidal) compounds or agents (i.e. active ingredients) can result in a greater-than-additive (i.e. synergistic) effect on weeds and/or a less-than-additive effect (i.e. safening) on crops or other desirable plants. Reducing the quantity of active ingredients released in the environment while ensuring effective pest control is always desirable. Ability to use greater amounts of active ingredients to provide more effective weed control without excessive crop injury is also desirable. When synergism of herbicidal active ingredients occurs on weeds at application rates giving agronomically satisfactory levels of weed control, such combinations can be advantageous for reducing crop production cost and decreasing environmental load. When safening of herbicidal active ingredients occurs on crops, such combinations can be advantageous for increasing crop protection by reducing weed competition.

Of note is a combination of a compound of the invention with at least one other herbicidal active ingredient. Of particular note is such a combination where the other herbicidal active ingredient has different site of action from the compound of the invention. In certain instances, a combination with at least one other herbicidal active ingredient having a similar spectrum of control but a different site of action will be particularly advantageous for resistance management. Thus, a composition of the present invention can further comprise (in a herbicidally effective amount) at least one additional herbicidal active ingredient having a similar spectrum of control but a different site of action.

Compounds of this invention can also be used in combination with herbicide safeners such as allidochlor, benoxacor, cloquintocet-mexyl, cumyluron, cyometrinil, cyprosulfonamide, daimuron, dichlormid, dicyclonon, dietholate, dimepiperate, fenchlorazole-ethyl, fenclorim, flurazole, fluxofenim, furilazole, isoxadifen-ethyl, mefenpyr-diethyl, mephenate, methoxyphenone naphthalic anhydride (1,8-naphthalic anhydride), oxabetrinil, N-(aminocarbonyl)-2-methylbenzenesulfonamide, N-(aminocarbonyl)-2-fluorobenzenesulfonamide, 1-bromo-4-[(chloromethyl) sulfonyl]benzene (BCS), 4-(dichloroacetyl)-1-oxa-4-azospiro[4.5]decane (MON 4660), 2-(dichloromethyl)-2-methyl-1,3-dioxolane (MG 191), ethyl 1,6-dihydro-1-(2-methoxyphenyl)-6-oxo-2-phenyl-5-pyrimidinecarboxylate, 2-hydroxy-N,N-dimethyl-6-(trifluoromethyl)pyridine-3-carboxamide, and 3-oxo-1-cyclohexen-1-yl 1-(3,4-dimethylphenyl)-1,6-dihydro-6-oxo-2-phenyl-5-pyrimidinecarboxylate, 2,2-dichloro-1-(2,5-trimethyl-3-oxazolidinyl)-ethanone and 2-methoxy-N-[[4-[[(methylamino)carbonyl] amino]phenyl]sulfonyl]-benzamide to increase safety to certain crops. Antidotally effective amounts of the herbicide safeners can be applied at the same time as the compounds of this invention, or applied as seed treatments. Therefore an aspect of the present invention relates to a herbicidal mixture comprising a compound of this invention and an antidotally effective amount of a herbicide safener. Seed treatment is particularly useful for selective weed control, because it physically restricts antidoting to the crop plants. Therefore a particularly useful embodiment of the present invention is a method for selectively controlling the growth of undesired vegetation in a crop comprising contacting the locus of the crop with a herbicidally effective amount of a compound of this invention wherein seed from which the crop is grown is treated with an antidotally effective amount of safener. Antidotally effective amounts of safeners can be easily determined by one skilled in the art through simple experimentation.

Compounds of the invention cans also be mixed with: (1) polynucleotides including but not limited to DNA, RNA, and/or chemically modified nucleotides influencing the amount of a particular target through down regulation, interference, suppression or silencing of the genetically derived transcript that render a herbicidal effect; or (2) polynucleotides including but not limited to DNA, RNA, and/or chemically modified nucleotides influencing the amount of a particular target through down regulation, interference, suppression or silencing of the genetically derived transcript that render a safening effect.

Of note is a composition comprising a compound of the invention (in a herbicidally effective amount), at least one additional active ingredient selected from the group consisting of other herbicides and herbicide safeners (in an effective amount), and at least one component selected from the group consisting of surfactants, solid diluents and liquid diluents.

Table A1 lists specific combinations of a Component (a) with Component (b) illustrative of the mixtures, compositions and methods of the present invention. Compound 1 in the Component (a) column is identified in Index Tables A. The second column of Table A1 lists the specific Component (b) compound (e.g., "2,4-D" in the first line). The third, fourth and fifth columns of Table A1 lists ranges of weight ratios for rates at which the Component (a) compound is typically applied to a field-grown crop relative to Component (b) (i.e. (a):(b)). Thus, for example, the first line of Table A1 specifically discloses the combination of Component (a) (i.e. Compound 1 in Index Table A) with 2,4-D is typically applied in a weight ratio between 1:192-6:1. The remaining lines of Table A1 are to be construed similarly.

TABLE A1

| Component (a) (Compound #) | Component (b) | Typical Weight Ratio | More Typical Weight Ratio | Most Typical Weight Ratio |
|---|---|---|---|---|
| 1 | 2,4-D | 1:192-6:1 | 1:64-2:1 | 1:24-1:3 |
| 1 | Acetochlor | 1:768-2:1 | 1:256-1:2 | 1:96-1:11 |
| 1 | Acifluorfen | 1:96-12:1 | 1:32-4:1 | 1:12-1:2 |
| 1 | Aclonifen | 1:857-2:1 | 1:285-1:3 | 1:107-1:12 |
| 1 | Alachlor | 1:768-2:1 | 1:256-1:2 | 1:96-1:11 |
| 1 | Ametryn | 1:384-3:1 | 1:128-1:1 | 1:48-1:6 |
| 1 | Amicarbazone | 1:192-6:1 | 1:64-2:1 | 1:24-1:3 |
| 1 | Amidosulfuron | 1:6-168:1 | 1:2-56:1 | 1:1-11:1 |
| 1 | Aminocyclopyrachlor | 1:48-24:1 | 1:16-8:1 | 1:6-2:1 |
| 1 | Aminopyralid | 1:20-56:1 | 1:6-19:1 | 1:2-4:1 |
| 1 | Amitrole | 1:768-2:1 | 1:256-1:2 | 1:96-1:11 |
| 1 | Anilofos | 1:96-12:1 | 1:32-4:1 | 1:12-1:2 |
| 1 | Asulam | 1:960-2:1 | 1:320-1:3 | 1:120-1:14 |
| 1 | Atrazine | 1:192-6:1 | 1:64-2:1 | 1:24-1:3 |
| 1 | Azimsulfuron | 1:6-168:1 | 1:2-56:1 | 1:1-11:1 |
| 1 | Beflubutamid | 1:342-4:1 | 1:114-2:1 | 1:42-1:5 |
| 1 | Benfuresate | 1:617-2:1 | 1:205-1:2 | 1:77-1:9 |
| 1 | Bensulfuron-methyl | 1:25-45:1 | 1:8-15:1 | 1:3-3:1 |
| 1 | Bentazone | 1:192-6:1 | 1:64-2:1 | 1:24-1:3 |
| 1 | Benzobicyclon | 1:85-14:1 | 1:28-5:1 | 1:10-1:2 |
| 1 | Benzofenap | 1:257-5:1 | 1:85-2:1 | 1:32-1:4 |
| 1 | Bicyclopyrone | 1:42-27:1 | 1:14-9:1 | 1:5-2:1 |
| 1 | Bifenox | 1:257-5:1 | 1:85-2:1 | 1:32-1:4 |
| 1 | Bispyribac-sodium | 1:10-112:1 | 1:3-38:1 | 1:1-7:1 |
| 1 | Bromacil | 1:384-3:1 | 1:128-1:1 | 1:48-1:6 |
| 1 | Bromobutide | 1:384-3:1 | 1:128-1:1 | 1:48-1:6 |
| 1 | Bromoxynil | 1:96-12:1 | 1:32-4:1 | 1:12-1:2 |
| 1 | Butachlor | 1:768-2:1 | 1:256-1:2 | 1:96-1:11 |
| 1 | Butafenacil | 1:42-27:1 | 1:14-9:1 | 1:5-2:1 |
| 1 | Butylate | 1:1542-1:2 | 1:514-1:5 | 1:192-1:22 |
| 1 | Carfenstrole | 1:192-6:1 | 1:64-2:1 | 1:24-1:3 |
| 1 | Carfentrazone-ethyl | 1:128-9:1 | 1:42-3:1 | 1:16-1:2 |
| 1 | Chlorimuron-ethyl | 1:8-135:1 | 1:2-45:1 | 1:1-9:1 |
| 1 | Chlorotoluron | 1:768-2:1 | 1:256-1:2 | 1:96-1:11 |
| 1 | Chlorsulfuron | 1:6-168:1 | 1:2-56:1 | 1:1-11:1 |
| 1 | Cincosulfuron | 1:17-68:1 | 1:5-23:1 | 1:2-5:1 |
| 1 | Cinidon-ethyl | 1:384-3:1 | 1:128-1:1 | 1:48-1:6 |
| 1 | Cinmethylin | 1:34-34:1 | 1:11-12:1 | 1:4-3:1 |
| 1 | Clacyfos | 1:34-34:1 | 1:11-12:1 | 1:4-3:1 |
| 1 | Clethodim | 1:48-24:1 | 1:16-8:1 | 1:6-2:1 |
| 1 | Clodinafop-propargyl | 1:20-56:1 | 1:6-19:1 | 1:2-4:1 |
| 1 | Clomazone | 1:384-3:1 | 1:128-1:1 | 1:48-1:6 |
| 1 | Clomeprop | 1:171-7:1 | 1:57-3:1 | 1:21-1:3 |
| 1 | Clopyralid | 1:192-6:1 | 1:64-2:1 | 1:24-1:3 |
| 1 | Cloransulam-methyl | 1:12-96:1 | 1:4-32:1 | 1:1-6:1 |
| 1 | Cumyluron | 1:384-3:1 | 1:128-1:1 | 1:48-1:6 |
| 1 | Cyanazine | 1:384-3:1 | 1:128-1:1 | 1:48-1:6 |
| 1 | Cyclopyrimorate | 1:17-68:1 | 1:5-23:1 | 1:2-5:1 |
| 1 | Cyclosulfamuron | 1:17-68:1 | 1:5-23:1 | 1:2-5:1 |
| 1 | Cycloxydim | 1:96-12:1 | 1:32-4:1 | 1:12-1:2 |
| 1 | Cyhalofop | 1:25-45:1 | 1:8-15:1 | 1:3-3:1 |
| 1 | Daimuron | 1:192-6:1 | 1:64-2:1 | 1:24-1:3 |
| 1 | Desmedipham | 1:322-4:1 | 1:107-2:1 | 1:40-1:5 |
| 1 | Dicamba | 1:192-6:1 | 1:64-2:1 | 1:24-1:3 |
| 1 | Dichlobenil | 1:1371-1:2 | 1:457-1:4 | 1:171-1:20 |
| 1 | Dichlorprop | 1:925-2:1 | 1:308-1:3 | 1:115-1:13 |
| 1 | Diclofop-methyl | 1:384-3:1 | 1:128-1:1 | 1:48-1:6 |
| 1 | Diclosulam | 1:10-112:1 | 1:3-38:1 | 1:1-7:1 |
| 1 | Difenzoquat | 1:288-4:1 | 1:96-2:1 | 1:36-1:4 |
| 1 | Diflufenican | 1:857-2:1 | 1:285-1:3 | 1:107-1:12 |
| 1 | Diflufenzopyr | 1:12-96:1 | 1:4-32:1 | 1:1-6:1 |
| 1 | Dimethachlor | 1:768-2:1 | 1:256-1:2 | 1:96-1:11 |
| 1 | Dimethametryn | 1:192-6:1 | 1:64-2:1 | 1:24-1:3 |
| 1 | Dimethenamid-P | 1:384-3:1 | 1:128-1:1 | 1:48-1:6 |
| 1 | Dithiopyr | 1:192-6:1 | 1:64-2:1 | 1:24-1:3 |
| 1 | Diuron | 1:384-3:1 | 1:128-1:1 | 1:48-1:6 |
| 1 | EPTC | 1:768-2:1 | 1:256-1:2 | 1:96-1:11 |
| 1 | Esprocarb | 1:1371-1:2 | 1:457-1:4 | 1:171-1:20 |
| 1 | Ethalfluralin | 1:384-3:1 | 1:128-1:1 | 1:48-1:6 |
| 1 | Ethametsulfuron-methyl | 1:17-68:1 | 1:5-23:1 | 1:2-5:1 |
| 1 | Ethoxyfen | 1:8-135:1 | 1:2-45:1 | 1:1-9:1 |
| 1 | Ethoxysulfuron | 1:20-56:1 | 1:6-19:1 | 1:2-4:1 |
| 1 | Etobenzanid | 1:257-5:1 | 1:85-2:1 | 1:32-1:4 |
| 1 | Fenoxaprop-ethyl | 1:120-10:1 | 1:40-4:1 | 1:15-1:2 |
| 1 | Fenoxasulfone | 1:85-14:1 | 1:28-5:1 | 1:10-1:2 |
| 1 | Fenquinotrione | 1:17-68:1 | 1:5-23:1 | 1:2-5:1 |
| 1 | Fentrazamide | 1:17-68:1 | 1:5-23:1 | 1:2-5:1 |

TABLE A1-continued

| Component (a) (Compound #) | Component (b) | Typical Weight Ratio | More Typical Weight Ratio | Most Typical Weight Ratio |
|---|---|---|---|---|
| 1 | Flazasulfuron | 1:17-68:1 | 1:5-23:1 | 1:2-5:1 |
| 1 | Florasulam | 1:2-420:1 | 1:1-140:1 | 2:1-27:1 |
| 1 | Fluazifop-butyl | 1:192-6:1 | 1:64-2:1 | 1:24-1:3 |
| 1 | Flucarbazone | 1:8-135:1 | 1:2-45:1 | 1:1-9:1 |
| 1 | Flucetosulfuron | 1:8-135:1 | 1:2-45:1 | 1:1-9:1 |
| 1 | Flufenacet | 1:257-5:1 | 1:85-2:1 | 1:32-1:4 |
| 1 | Flumetsulam | 1:24-48:1 | 1:8-16:1 | 1:3-3:1 |
| 1 | Flumiclorac-pentyl | 1:10-112:1 | 1:3-38:1 | 1:1-7:1 |
| 1 | Flumioxazin | 1:25-45:1 | 1:8-15:1 | 1:3-3:1 |
| 1 | Fluometuron | 1:384-3:1 | 1:128-1:1 | 1:48-1:6 |
| 1 | Flupyrsulfuron-methyl | 1:3-336:1 | 1:1-112:1 | 2:1-21:1 |
| 1 | Fluridone | 1:384-3:1 | 1:128-1:1 | 1:48-1:6 |
| 1 | Fluroxypyr | 1:96-12:1 | 1:32-4:1 | 1:12-1:2 |
| 1 | Flurtamone | 1:857-2:1 | 1:285-1:3 | 1:107-1:12 |
| 1 | Fluthiacet-methyl | 1:48-42:1 | 1:16-14:1 | 1:3-3:1 |
| 1 | Fomesafen | 1:96-12:1 | 1:32-4:1 | 1:12-1:2 |
| 1 | Foramsulfuron | 1:13-84:1 | 1:4-28:1 | 1:1-6:1 |
| 1 | Glufosinate | 1:288-4:1 | 1:96-2:1 | 1:36-1:4 |
| 1 | Glyphosate | 1:288-4:1 | 1:96-2:1 | 1:36-1:4 |
| 1 | Halosulfuron-methyl | 1:17-68:1 | 1:5-23:1 | 1:2-5:1 |
| 1 | Halauxifen | 1:20-56:1 | 1:6-19:1 | 1:2-4:1 |
| 1 | Halauxifen methyl | 1:20-56:1 | 1:6-19:1 | 1:2-4:1 |
| 1 | Haloxyfop-methyl | 1:34-34:1 | 1:11-12:1 | 1:4-3:1 |
| 1 | Hexazinone | 1:192-6:1 | 1:64-2:1 | 1:24-1:3 |
| 1 | Hydantocidin | 1:1100-16:1 | 1:385-8:1 | 1:144-4:1 |
| 1 | Imazamox | 1:13-84:1 | 1:4-28:1 | 1:1-6:1 |
| 1 | Imazapic | 1:20-56:1 | 1:6-19:1 | 1:2-4:1 |
| 1 | Imazapyr | 1:85-14:1 | 1:28-5:1 | 1:10-1:2 |
| 1 | Imazaquin | 1:34-34:1 | 1:11-12:1 | 1:4-3:1 |
| 1 | Imazethabenz-methyl | 1:171-7:1 | 1:57-3:1 | 1:21-1:3 |
| 1 | Imazethapyr | 1:24-48:1 | 1:8-16:1 | 1:3-3:1 |
| 1 | Imazosulfuron | 1:27-42:1 | 1:9-14:1 | 1:3-3:1 |
| 1 | Indanofan | 1:342-4:1 | 1:114-2:1 | 1:42-1:5 |
| 1 | Indaziflam | 1:25-45:1 | 1:8-15:1 | 1:3-3:1 |
| 1 | Iodosulfuron-methyl | 1:3-336:1 | 1:1-112:1 | 2:1-21:1 |
| 1 | Ioxynil | 1:192-6:1 | 1:64-2:1 | 1:24-1:3 |
| 1 | Ipfencarbazone | 1:85-14:1 | 1:28-5:1 | 1:10-1:2 |
| 1 | Isoproturon | 1:384-3:1 | 1:128-1:1 | 1:48-1:6 |
| 1 | Isoxaben | 1:288-4:1 | 1:96-2:1 | 1:36-1:4 |
| 1 | Isoxaflutole | 1:60-20:1 | 1:20-7:1 | 1:7-2:1 |
| 1 | Lactofen | 1:42-27:1 | 1:14-9:1 | 1:5-2:1 |
| 1 | Lenacil | 1:384-3:1 | 1:128-1:1 | 1:48-1:6 |
| 1 | Linuron | 1:384-3:1 | 1:128-1:1 | 1:48-1:6 |
| 1 | MCPA | 1:192-6:1 | 1:64-2:1 | 1:24-1:3 |
| 1 | MCPB | 1:288-4:1 | 1:96-2:1 | 1:36-1:4 |
| 1 | Mecoprop | 1:768-2:1 | 1:256-1:2 | 1:96-1:11 |
| 1 | Mefenacet | 1:384-3:1 | 1:128-1:1 | 1:48-1:6 |
| 1 | Mefluidide | 1:192-6:1 | 1:64-2:1 | 1:24-1:3 |
| 1 | Mesosulfuron-methyl | 1:5-224:1 | 1:1-75:1 | 1:1-14:1 |
| 1 | Mesotrione | 1:42-27:1 | 1:14-9:1 | 1:5-2:1 |
| 1 | Metamifop | 1:42-27:1 | 1:14-9:1 | 1:5-2:1 |
| 1 | Metazachlor | 1:384-3:1 | 1:128-1:1 | 1:48-1:6 |
| 1 | Metazosulfuron | 1:25-45:1 | 1:8-15:1 | 1:3-3:1 |
| 1 | Methabenzthiazuron | 1:768-2:1 | 1:256-1:2 | 1:96-1:11 |
| 1 | Metolachlor | 1:768-2:1 | 1:256-1:2 | 1:96-1:11 |
| 1 | Metosulam | 1:8-135:1 | 1:2-45:1 | 1:1-9:1 |
| 1 | Metribuzin | 1:192-6:1 | 1:64-2:1 | 1:24-1:3 |
| 1 | Metsulfuron-methyl | 1:2-560:1 | 1:1-187:1 | 3:1-35:1 |
| 1 | Molinate | 1:1028-2:1 | 1:342-1:3 | 1:128-1:15 |
| 1 | Napropamide | 1:384-3:1 | 1:128-1:1 | 1:48-1:6 |
| 1 | Napropamide-M | 1:192-6:1 | 1:64-2:1 | 1:24-1:3 |
| 1 | Naptalam | 1:192-6:1 | 1:64-2:1 | 1:24-1:3 |
| 1 | Nicosulfuron | 1:12-96:1 | 1:4-32:1 | 1:1-6:1 |
| 1 | Norflurazon | 1:1152-1:1 | 1:384-1:3 | 1:144-1:16 |
| 1 | Orbencarb | 1:1371-1:2 | 1:457-1:4 | 1:171-1:20 |
| 1 | Orthosulfamuron | 1:20-56:1 | 1:6-19:1 | 1:2-4:1 |
| 1 | Oryzalin | 1:514-3:1 | 1:171-1:2 | 1:64-1:8 |
| 1 | Oxadiargyl | 1:384-3:1 | 1:128-1:1 | 1:48-1:6 |
| 1 | Oxadiazon | 1:548-3:1 | 1:182-1:2 | 1:68-1:8 |
| 1 | Oxasulfuron | 1:27-42:1 | 1:9-14:1 | 1:3-3:1 |
| 1 | Oxaziclomefone | 1:42-27:1 | 1:14-9:1 | 1:5-2:1 |
| 1 | Oxyfluorfen | 1:384-3:1 | 1:128-1:1 | 1:48-1:6 |
| 1 | Paraquat | 1:192-6:1 | 1:64-2:1 | 1:24-1:3 |
| 1 | Pendimethalin | 1:384-3:1 | 1:128-1:1 | 1:48-1:6 |
| 1 | Penoxsulam | 1:10-112:1 | 1:3-38:1 | 1:1-7:1 |
| 1 | Penthoxamid | 1:384-3:1 | 1:128-1:1 | 1:48-1:6 |
| 1 | Pentoxazone | 1:102-12:1 | 1:34-4:1 | 1:12-1:2 |

TABLE A1-continued

| Component (a) (Compound #) | Component (b) | Typical Weight Ratio | More Typical Weight Ratio | Most Typical Weight Ratio |
|---|---|---|---|---|
| 1 | Phenmedipham | 1:102-12:1 | 1:34-4:1 | 1:12-1:2 |
| 1 | Picloram | 1:96-12:1 | 1:32-4:1 | 1:12-1:2 |
| 1 | Picolinafen | 1:34-34:1 | 1:11-12:1 | 1:4-3:1 |
| 1 | Pinoxaden | 1:25-45:1 | 1:8-15:1 | 1:3-3:1 |
| 1 | Pretilachlor | 1:192-6:1 | 1:64-2:1 | 1:24-1:3 |
| 1 | Primisulfuron-methyl | 1:8-135:1 | 1:2-45:1 | 1:1-9:1 |
| 1 | Prodiamine | 1:384-3:1 | 1:128-1:1 | 1:48-1:6 |
| 1 | Profoxydim | 1:42-27:1 | 1:14-9:1 | 1:5-2:1 |
| 1 | Prometryn | 1:384-3:1 | 1:128-1:1 | 1:48-1:6 |
| 1 | Propachlor | 1:1152-1:1 | 1:384-1:3 | 1:144-1:16 |
| 1 | Propanil | 1:384-3:1 | 1:128-1:1 | 1:48-1:6 |
| 1 | Propaquizafop | 1:48-24:1 | 1:16-8:1 | 1:6-2:1 |
| 1 | Propoxycarbazone | 1:17-68:1 | 1:5-23:1 | 1:2-5:1 |
| 1 | Propyrisulfuron | 1:17-68:1 | 1:5-23:1 | 1:2-5:1 |
| 1 | Propyzamide | 1:384-3:1 | 1:128-1:1 | 1:48-1:6 |
| 1 | Prosulfocarb | 1:1200-1:2 | 1:400-1:4 | 1:150-1:17 |
| 1 | Prosulfuron | 1:6-168:1 | 1:2-56:1 | 1:1-11:1 |
| 1 | Pyraclonil | 1:42-27:1 | 1:14-9:1 | 1:5-2:1 |
| 1 | Pyraflufen-ethyl | 1:5-224:1 | 1:1-75:1 | 1:1-14:1 |
| 1 | Pyrasulfotole | 1:13-84:1 | 1:4-28:1 | 1:1-6:1 |
| 1 | Pyrazolynate | 1:857-2:1 | 1:285-1:3 | 1:107-1:12 |
| 1 | Pyrazosulfuron-ethyl | 1:10-112:1 | 1:3-38:1 | 1:1-7:1 |
| 1 | Pyrazoxyfen | 1:5-224:1 | 1:1-75:1 | 1:1-14:1 |
| 1 | Pyribenzoxim | 1:10-112:1 | 1:3-38:1 | 1:1-7:1 |
| 1 | Pyributicarb | 1:384-3:1 | 1:128-1:1 | 1:48-1:6 |
| 1 | Pyridate | 1:288-4:1 | 1:96-2:1 | 1:36-1:4 |
| 1 | Pyriftalid | 1:10-112:1 | 1:3-38:1 | 1:1-7:1 |
| 1 | Pyriminobac-methyl | 1:20-56:1 | 1:6-19:1 | 1:2-4:1 |
| 1 | Pyrimisulfan | 1:17-68:1 | 1:5-23:1 | 1:2-5:1 |
| 1 | Pyrithiobac | 1:24-48:1 | 1:8-16:1 | 1:3-3:1 |
| 1 | Pyroxasulfone | 1:85-14:1 | 1:28-5:1 | 1:10-1:2 |
| 1 | Pyroxsulam | 1:5-224:1 | 1:1-75:1 | 1:1-14:1 |
| 1 | Quinclorac | 1:192-6:1 | 1:64-2:1 | 1:24-1:3 |
| 1 | Quizalofop-ethyl | 1:42-27:1 | 1:14-9:1 | 1:5-2:1 |
| 1 | Rimsulfuron | 1:13-84:1 | 1:4-28:1 | 1:1-6:1 |
| 1 | Saflufenacil | 1:25-45:1 | 1:8-15:1 | 1:3-3:1 |
| 1 | Sethoxydim | 1:96-12:1 | 1:32-4:1 | 1:12-1:2 |
| 1 | Simazine | 1:384-3:1 | 1:128-1:1 | 1:48-1:6 |
| 1 | Sulcotrione | 1:120-10:1 | 1:40-4:1 | 1:15-1:2 |
| 1 | Sulfentrazone | 1:147-8:1 | 1:49-3:1 | 1:18-1:3 |
| 1 | Sulfometuron-methyl | 1:34-34:1 | 1:11-12:1 | 1:4-3:1 |
| 1 | Sulfosulfuron | 1:8-135:1 | 1:2-45:1 | 1:1-9:1 |
| 1 | Tebuthiuron | 1:384-3:1 | 1:128-1:1 | 1:48-1:6 |
| 1 | Tefuryltrione | 1:42-27:1 | 1:14-9:1 | 1:5-2:1 |
| 1 | Tembotrione | 1:31-37:1 | 1:10-13:1 | 1:3-3:1 |
| 1 | Tepraloxydim | 1:25-45:1 | 1:8-15:1 | 1:3-3:1 |
| 1 | Terbacil | 1:288-4:1 | 1:96-2:1 | 1:36-1:4 |
| 1 | Terbuthylazine | 1:857-2:1 | 1:285-1:3 | 1:107-1:12 |
| 1 | Terbutryn | 1:192-6:1 | 1:64-2:1 | 1:24-1:3 |
| 1 | Thenylchlor | 1:85-14:1 | 1:28-5:1 | 1:10-1:2 |
| 1 | Thiazopyr | 1:384-3:1 | 1:128-1:1 | 1:48-1:6 |
| 1 | Thiencarbazone | 1:3-336:1 | 1:1-112:1 | 2:1-21:1 |
| 1 | Thifensulfuron-methyl | 1:5-224:1 | 1:1-75:1 | 1:1-14:1 |
| 1 | Tiafenacil | 1:17-68:1 | 1:5-23:1 | 1:2-5:1 |
| 1 | Thiobencarb | 1:768-2:1 | 1:256-1:2 | 1:96-1:11 |
| 1 | Tolpyralate | 1:31-37:1 | 1:10-13:1 | 1:3-3:1 |
| 1 | Topramzone | 1:6-168:1 | 1:2-56:1 | 1:1-11:1 |
| 1 | Tralkoxydim | 1:68-17:1 | 1:22-6:1 | 1:8-2:1 |
| 1 | Triafamone | 1:2-420:1 | 1:1-140:1 | 2:1-27:1 |
| 1 | Triallate | 1:768-2:1 | 1:256-1:2 | 1:96-1:11 |
| 1 | Triasulfuron | 1:5-224:1 | 1:1-75:1 | 1:1-14:1 |
| 1 | Triaziflam | 1:171-7:1 | 1:57-3:1 | 1:21-1:3 |
| 1 | Tribenuron-methyl | 1:3-336:1 | 1:1-112:1 | 2:1-21:1 |
| 1 | Triclopyr | 1:192-6:1 | 1:64-2:1 | 1:24-1:3 |
| 1 | Trifloxysulfuron | 1:2-420:1 | 1:1-140:1 | 2:1-27:1 |
| 1 | Trifludimoxazin | 1:25-45:1 | 1:8-15:1 | 1:3-3:1 |
| 1 | Trifluralin | 1:288-4:1 | 1:96-2:1 | 1:36-1:4 |
| 1 | Triflusulfuron-methyl | 1:17-68:1 | 1:5-23:1 | 1:2-5:1 |
| 1 | Tritosulfuron | 1:13-84:1 | 1:4-28:1 | 1:1-6:1 |

Table A2 is constructed the same as Table A1 above except that entries below the "Component (a)" column heading are replaced with the respective Component (a) Column Entry shown below. Compound 2 in the Component (a) column is identified in Index Table A. Thus, for example, in Table A2 the entries below the "Component (a)" column heading all recite "Compound 2" (i.e. Compound 2 identified in Index Table A), and the first line below the column headings in Table A2 specifically discloses a mixture of Compound 2 with 2,4-D. Tables A3 through A4 are constructed similarly.

| Table Number | Component (a) Column Entries |
|---|---|
| A2 | Compound 2 |
| A3 | Compound 5 |
| A4 | Compound 6 |
| A5 | Compound 3 |
| A6 | Compound 4 |
| A7 | Compound 7 |
| A8 | Compound 8 |
| A9 | Compound 9 |
| A10 | Compound 10 |
| A11 | Compound 11 |
| A12 | Compound 12 |
| A13 | Compound 13 |
| A14 | Compound 14 |

Preferred for better control of undesired vegetation (e.g., lower use rate such as from synergism, broader spectrum of weeds controlled, or enhanced crop safety) or for preventing the development of resistant weeds are mixtures of a compound of this invention with a herbicide selected from the group consisting of chlorimuron-ethyl, nicosulfuron, diuron, hexazinoe, thifensulfuron-methyl and S-metolachlor.

The compounds of the present invention are useful for the control of weed species that are resistant to herbicides with the AHAS-inhibitor or (b2) [chemical compound that inhibits acetohydroxy acid synthase (AHAS), also known as acetolactate synthase (ALS)] mode of action.

The following Tests demonstrate the control efficacy of the compounds of this invention against specific weeds. The weed control afforded by the compounds is not limited, however, to these species. See Index Tables A and B for compound descriptions. The following abbreviations are used in the Index Tables which follow: t is tertiary, s is secondary, n is normal, i is iso, c is cyclo, Me is methyl, Et is ethyl, Pr is propyl, i-Pr is isopropyl, t-Bu is tertiary-butyl, i-Pr is iso-propyl, c-Pr is cyclopropyl, Ph is phenyl, OMe is methoxy, OEt is ethoxy, SMe is methylthio, SEt is ethylthio and —CN is cyano. The abbreviation "Cmpd. No." stands for "Compound Number". Mass spectra are reported with an estimated precision within +0.5 Da as the molecular weight of the highest isotopic abundance parent ion (M+1) formed by addition of $H^+$ (molecular weight of 1) to the molecule observed by using atmospheric pressure chemical ionization (AP+).

INDEX TABLE A

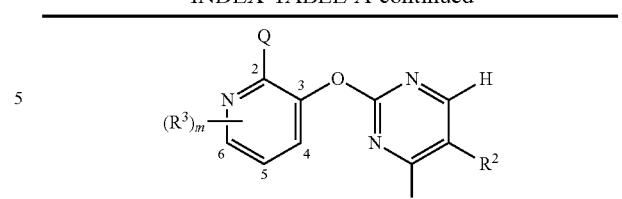

| No. | Q | $R^2$ | $(R^3)_m$ | M.S.(AP+) or m.p. |
|---|---|---|---|---|
| 1 (Ex. 2) | 4-Br-1H-pyrazol-1-yl | Cl | m = 0 | 129-131 |
| 2 | 4-Cl-1H-pyrazol-1-yl | Cl | m = 0 | 138-140 |
| 3 | 4-CH$_3$-1H-pyrazol-1-yl | Cl | m = 0 | 110-113 |
| 4 | 4-Ph-1H-pyrazol-1-yl | Cl | m = 0 | 130-132 |
| 5 | 3-CF$_2$H-5-isoxazolyl | Cl | m = 0 | 325 |

INDEX TABLE A-continued

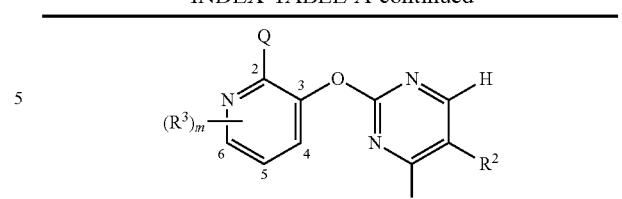

| No. | Q | $R^2$ | $(R^3)_m$ | M.S.(AP+) or m.p. |
|---|---|---|---|---|
| 6 (Ex. 1) | 5-CF$_2$H-3-isoxazolyl | Cl | m = 0 | 100-104 |
| 7 | 3-CF$_2$H-5-isoxazolyl | F | m = 0 | 100-104 |
| 10 | 4-Br-1H-pyrazol-1-yl | Cl | 6-CH$_3$ | 367 |
| 12 (Ex. 3) | (5-Cl-pyridin-2-yl) | Cl | m = 0 | 319 |
| 13 | (3-CF$_3$-1H-pyrazol-1-yl) | Cl | 5-CH$_3$ | 103.5-109 |
| 14 | (2-CF$_3$-pyridin-4-yl) | Cl | m = 0 | 353 |

INDEX TABLE B

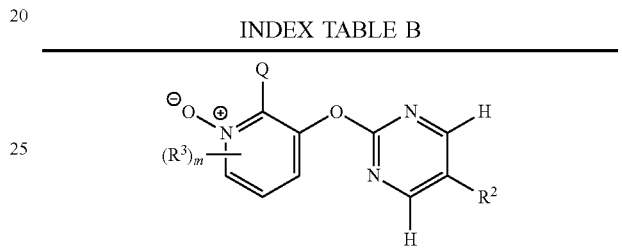

| No. | Q | $R^2$ | $(R^3)_m$ | M.S.(AP+) or m.p. |
|---|---|---|---|---|
| 8 (Ex. 1) | 5-CF$_2$H-3-isoxazolyl | Cl | m = 0 | 139-143 |
| 9 | 4-Cl-1H-pyrazol-1-yl | F | m = 0 | 129-133 |
| 11 | 4-Br-1H-pyrazol-1-yl | Cl | m = 0 | 368 |

Biological Examples of the Invention

Test A

Seeds of plant species selected from barnyardgrass (*Echinochloa crus-galli*), kochia (*Kochia scoparia*), ragweed (common ragweed, *Ambrosia elatior*), ryegrass, Italian (Italian ryegrass, *Lolium multiflorum*), foxtail, giant (giant foxtail, *Setaria faberii*), pigweed (*Amaranthus retroflexus*), crabgrass, large (large crabgrass, *Digitaria sanguinalis*), momingglory (*Ipomoea* spp.), velvetleaf (*Abutilon theophrasti*), wheat (*Triticum aestivum*), and corn (*Zea mays*) were planted into a blend of loam soil and sand and treated preemergence with a directed soil spray using test chemicals formulated in a non-phytotoxic solvent mixture which included a surfactant.

At the same time, plants selected from these crop and weed species and also blackgrass (*Alopecurus myosuroides*), and galium (catchweed bedstraw, *Galium aparine*) were planted in pots containing the same blend of loam soil and sand and treated with postemergence applications of test chemicals formulated in the same manner. Plants ranged in height from 2 to 10 cm and were in the one- to two-leaf stage for the postemergence treatment. Treated plants and untreated controls were maintained in a greenhouse for approximately 10 days, after which time all treated plants were compared to untreated controls and visually evaluated for injury. Plant response ratings, summarized in Table A, are based on a 0 to 100 scale where 0 is no effect and 100 is complete control. A dash (-) response means no test result.

TABLE A

| 1000 g ai/ha | Compound 11 |
|---|---|
| Postemergence | |
| Barnyardgrass | 0 |
| Blackgrass | 10 |
| Corn | 0 |
| Foxtail, Giant | 0 |
| Galium | 40 |
| Kochia | 60 |
| Pigweed | 90 |
| Ragweed | 20 |
| Ryegrass, Italian | 0 |
| Wheat | 0 |

| | Compounds | | | | | |
|---|---|---|---|---|---|---|
| 500 g ai/ha | 1 | 2 | 3 | 4 | 10 | 14 |
| Postemergence | | | | | | |
| Barnyardgrass | 10 | 20 | 10 | 20 | 0 | 60 |
| Blackgrass | — | — | — | — | — | 90 |
| Corn | 20 | 10 | 10 | 30 | 0 | 40 |
| Crabgrass, Large | 50 | 40 | 10 | 0 | 10 | — |
| Foxtail, Giant | 30 | 30 | 10 | 0 | 0 | 90 |
| Galium | — | — | — | — | — | 90 |
| Kochia | — | — | — | — | — | 100 |
| Morningglory | 80 | 80 | 30 | 10 | 10 | — |
| Pigweed | 100 | 100 | 40 | 70 | 50 | 100 |
| Ragweed | — | — | — | — | — | 30 |
| Ryegrass, Italian | — | — | — | — | — | 40 |
| Velvetleaf | 50 | 70 | 20 | 0 | 80 | — |
| Wheat | 20 | 20 | 10 | 0 | 0 | 10 |

| | Compounds | | | | | | | | | | | |
|---|---|---|---|---|---|---|---|---|---|---|---|---|
| 125 g ai/ha | 1 | 2 | 3 | 4 | 5 | 6 | 7 | 8 | 9 | 10 | 12 | 13 | 14 |
| Postemergence | | | | | | | | | | | | |
| Barnyardgrass | 0 | 0 | 0 | 0 | 20 | 30 | 0 | 10 | 0 | 0 | 30 | 0 | 40 |
| Blackgrass | — | — | — | — | 20 | 20 | 0 | 10 | 0 | — | 0 | 0 | 10 |
| Corn | 10 | 0 | 0 | 0 | 10 | 30 | 0 | 20 | 0 | 0 | 10 | 0 | 20 |
| Crabgrass, Large | 10 | 10 | 10 | 0 | — | — | — | — | 0 | — | — | — | — |
| Foxtail, Giant | 10 | 0 | 0 | 0 | 10 | 40 | 0 | 10 | 0 | 0 | 0 | 0 | 60 |
| Galium | — | — | — | — | 60 | 70 | 50 | 60 | 30 | — | 10 | 0 | 50 |
| Kochia | — | — | — | — | 90 | 100 | 90 | 70 | 50 | — | 40 | 0 | 80 |
| Morningglory | 10 | 40 | 20 | 0 | — | — | — | — | 0 | — | — | — | — |
| Pigweed | 90 | 100 | 10 | 20 | 90 | 100 | 70 | 70 | 50 | 10 | 30 | 0 | 100 |
| Ragweed | — | — | — | — | 60 | 40 | 10 | 50 | 30 | — | 10 | 0 | 10 |
| Ryegrass, Italian | — | — | — | 0 | 10 | 0 | 0 | 0 | — | 0 | 0 | 30 |
| Velvetleaf | 20 | 20 | 10 | 0 | — | — | — | — | 50 | — | — | — | — |
| Wheat | 10 | 10 | 10 | 0 | 10 | 30 | 20 | 20 | 0 | 0 | 0 | 0 | 0 |

| | Compounds | | | | | |
|---|---|---|---|---|---|---|
| 31 g ai/ha | 5 | 6 | 7 | 8 | 9 | 12 | 13 |
| Postemergence | | | | | | |
| Barnyardgrass | 0 | 10 | 0 | 0 | 0 | 0 | 0 |
| Blackgrass | 0 | 0 | 0 | 0 | 0 | 0 | 0 |
| Corn | 0 | 20 | 0 | 0 | 0 | 0 | 0 |
| Foxtail, Giant | 0 | 20 | 0 | 0 | 0 | 0 | 0 |
| Galium | 40 | 50 | 20 | 40 | 10 | 10 | 0 |
| Kochia | 80 | 90 | 70 | 40 | 10 | 0 | 0 |
| Pigweed | 80 | 70 | 20 | 50 | 30 | 10 | 0 |
| Ragweed | 20 | 20 | 0 | 30 | 10 | 0 | 0 |
| Ryegrass, Italian | 0 | 0 | 0 | 0 | 0 | 0 | 0 |
| Wheat | 0 | 20 | 0 | 10 | 0 | 0 | 0 |

TABLE A-continued

| 1000 g ai/ha | Compound 11 |
|---|---|
| Preemergence | |
| Barnyardgrass | 0 |
| Foxtail, Giant | 0 |
| Kochia | 30 |
| Pigweed | 100 |
| Ragweed | 30 |
| Ryegrass, Italian | 0 |

| | Compounds | | | | | |
|---|---|---|---|---|---|---|
| 500 g ai/ha | 1 | 2 | 3 | 4 | 10 | 14 |
| Preemergence | | | | | | |
| Barnyardgrass | 50 | 40 | 0 | 0 | 0 | 100 |
| Corn | 0 | 0 | 0 | 0 | 0 | — |
| Crabgrass, Large | 100 | 100 | 0 | 0 | 50 | — |
| Foxtail, Giant | 80 | 80 | 0 | 0 | 20 | 100 |
| Kochia | — | — | — | — | — | 100 |
| Morningglory | 0 | 0 | 0 | 0 | 10 | — |
| Pigweed | 90 | 90 | 10 | 0 | 40 | 100 |
| Ragweed | — | — | — | — | — | 20 |
| Ryegrass, Italian | — | — | — | — | — | 20 |
| Velvetleaf | 30 | 30 | 0 | 0 | 20 | — |
| Wheat | 10 | 10 | 0 | 0 | 0 | — |

| | Compounds | | | | | | | | | | | |
|---|---|---|---|---|---|---|---|---|---|---|---|---|
| 125 g ai/ha | 1 | 2 | 3 | 4 | 5 | 6 | 7 | 8 | 9 | 10 | 12 | 13 | 14 |
| Preemergence | | | | | | | | | | | | |
| Barnyardgrass | 10 | 0 | 0 | 0 | 20 | 70 | 20 | 0 | 0 | 0 | 0 | 0 | 40 |
| Corn | 0 | 0 | 0 | 0 | — | — | — | — | 0 | — | — | — | — |
| Crabgrass, Large | 40 | — | 0 | 0 | — | — | — | — | 0 | — | — | — | — |
| Foxtail, Giant | 20 | 10 | 0 | 0 | 80 | 90 | 20 | 10 | 0 | 0 | 0 | 0 | 90 |
| Kochia | — | — | — | — | 80 | 90 | 70 | 40 | 0 | — | 40 | 0 | 100 |
| Morningglory | — | 0 | 0 | 0 | — | — | — | — | 0 | — | — | — | — |
| Pigweed | 50 | 70 | 0 | 0 | 100 | 100 | 100 | 90 | 20 | 0 | 60 | 0 | 100 |
| Ragweed | — | — | — | — | 10 | 50 | 30 | 0 | 0 | — | 0 | 0 | 0 |
| Ryegrass, Italian | — | — | — | — | 0 | 0 | 0 | 0 | 0 | — | 0 | 0 | 10 |
| Velvetleaf | 10 | 10 | 0 | 0 | — | — | — | — | 0 | — | — | — | — |
| Wheat | 0 | 0 | 0 | 0 | — | — | — | — | 0 | — | — | — | — |

| | Compounds | | | | | |
|---|---|---|---|---|---|---|
| 31 g ai/ha | 5 | 6 | 7 | 8 | 9 | 12 | 13 |
| Preemergence | | | | | | |
| Barnyardgrass | 0 | 0 | 0 | 0 | 0 | 0 | 0 |

TABLE A-continued

| | | | | | | | |
|---|---|---|---|---|---|---|---|
| Foxtail, Giant | 10 | 0 | 0 | 0 | 0 | 0 | 0 |
| Kochia | 10 | 60 | 20 | 0 | 0 | 0 | 0 |
| Pigweed | 80 | 90 | 70 | 40 | 0 | 0 | 0 |
| Ragweed | 0 | 0 | 0 | 0 | 0 | 0 | 0 |
| Ryegrass, Italian | 0 | 0 | 0 | 0 | 0 | 0 | 0 |

Test B

Plant species in the flooded paddy test selected from rice (*Oryza sativa*), sedge, umbrella (small-flower umbrella sedge, *Cyperus difformis*), ducksalad (*Heteranthera limosa*), and barnyardgrass (*Echinochloa crus-galli*) were grown to the 2-leaf stage for testing. At time of treatment, test pots were flooded to 3 cm above the soil surface, treated by application of test compounds directly to the paddy water, and then maintained at that water depth for the duration of the test. Treated plants and controls were maintained in a greenhouse for 13 to 15 days, after which time all species were compared to controls and visually evaluated. Plant response ratings, summarized in Table B, are based on a scale of 0 to 100 where 0 is no effect and 100 is complete control. A dash (-) response means no test result.

TABLE B

| 250 g ai/ha | Compounds | | | | | | | | | | | | |
|---|---|---|---|---|---|---|---|---|---|---|---|---|---|
| | 1 | 2 | 3 | 4 | 5 | 6 | 7 | 8 | 9 | 10 | 12 | 13 | 14 |
| Flood | | | | | | | | | | | | | |
| Barnyardgrass | 0 | 0 | 0 | — | 0 | 0 | 0 | 0 | 0 | 0 | 0 | 0 | 0 |
| Ducksalad | 60 | 80 | 0 | 0 | 75 | 30 | 50 | 40 | 0 | 0 | 30 | 0 | 40 |
| Rice | 0 | 0 | 0 | 10 | 0 | 0 | 0 | 0 | 0 | 0 | 20 | 0 | 0 |
| Sedge, Umbrella | 50 | 75 | 60 | 70 | 80 | 0 | 0 | 0 | 0 | 0 | 30 | 0 | 50 |

Test C

Seeds of plant species selected from blackgrass (*Alopecurus myosuroides*), ryegrass, Italian (Italian ryegrass, *Lolium multiflorum*), wheat (winter wheat, *Triticum aestivum*), galium (catchweed bedstraw, *Galium aparine*), corn (*Zea mays*), crabgrass, large (large crabgrass, *Digitaria sanguinalis*), foxtail, giant (giant foxtail, *Setaria faberii*), lambsquarters (*Chenopodium album*), morningglory (*Ipomoea coccinea*), nutsedge, yellow (yellow nutsedge, *Cyperus esculentus*), pigweed (*Amaranthus retroflexus*), johnsongrass (*Sorghum halepense*), ragweed (common ragweed, *Ambrosia elatior*), soybean (*Glycine max*), barnyardgrass (*Echinochloa crus-galli*), oilseed rape (*Brassica napus*), waterhemp (common waterhemp, *Amaranthus rudis*), chickweed (common chickweed, *Stellaria media*), oat, wild (wild oat, *Avena fatua*), kochia (*Kochia scoparia*), and velvetleaf (*Abutilon theophrasti*) were planted in pots containing Redi-Earth® planting medium (Scotts Company, 14111 Scottslawn Road, Marysville, Ohio 43041) comprising spaghnum peat moss, vermiculite, wetting agent and starter nutrients and treated with postemergence applications of a test chemical formulated in a non-phytotoxic solvent mixture which included a surfactant. Plants ranged in height from 2 to 18 cm (1- to 4-leaf stage) for postemergence treatments. Treated plants and controls were maintained in a greenhouse for 13 to 15 days, after which time all species were compared to controls and visually evaluated. Plant response ratings, summarized in Table C, are based on a scale of 0 to 100 where 0 is no effect and 100 is complete control. A dash (-) response means no test result.

TABLE C

| | Compound |
|---|---|
| 125 g ai/ha Postemergence | 5 |
| Barnyardgrass | 10 |
| Blackgrass | 5 |
| Chickweed | 60 |
| Corn | 5 |
| Crabgrass, Large | 15 |
| Foxtail, Giant | 10 |
| *Galium* | 90 |
| Johnsongrass | 10 |
| *Kochia* | 90 |
| Lambsquarters | 60 |
| Morningglory | 85 |
| Nutsedge, Yellow | 5 |
| Oat, Wild | 5 |
| Oilseed Rape | 85 |
| Pigweed | 85 |
| Ragweed | 65 |
| Ryegrass, Italian | 5 |
| Soybean | 90 |
| Velvetleaf | 60 |
| Waterhemp | 85 |
| 62 g ai/ha Postemergence | 5 |
| Barnyardgrass | 5 |
| Blackgrass | 0 |
| Chickweed | 55 |
| Corn | 5 |
| Crabgrass, Large | 15 |
| Foxtail, Giant | 5 |
| *Galium* | 80 |
| Johnsongrass | 5 |
| *Kochia* | 90 |
| Lambsquarters | 55 |
| Morningglory | 65 |
| Nutsedge, Yellow | 5 |
| Oat, Wild | 0 |
| Oilseed Rape | 60 |
| Pigweed | 75 |
| Ragweed | 35 |
| Ryegrass, Italian | 0 |
| Soybean | 40 |
| Velvetleaf | 70 |
| Waterhemp | 75 |
| 31 g ai/ha Postemergence | 5 |
| Barnyardgrass | 0 |
| Blackgrass | 0 |
| Chickweed | 40 |
| Corn | 5 |
| Crabgrass, Large | 15 |
| Foxtail, Giant | 5 |
| *Galium* | 75 |
| Johnsongrass | 0 |
| *Kochia* | 90 |
| Lambsquarters | 70 |
| Morningglory | 65 |
| Nutsedge, Yellow | 10 |
| Oat, Wild | 0 |
| Oilseed Rape | 60 |
| Pigweed | 75 |
| Ragweed | 40 |
| Ryegrass, Italian | 5 |
| Soybean | 70 |
| Velvetleaf | 50 |
| Waterhemp | 65 |
| Wheat | 5 |
| 16 g ai/ha Postemergence | 5 |
| Barnyardgrass | 0 |
| Blackgrass | 0 |
| Chickweed | 35 |
| Corn | 5 |
| Crabgrass, Large | 10 |

TABLE C-continued

| Compound | |
|---|---|
| Foxtail, Giant | 0 |
| *Galium* | 35 |
| Johnsongrass | 0 |
| *Kochia* | 90 |
| Lambsquarters | 35 |
| Morningglory | 75 |
| Nutsedge, Yellow | 0 |
| Oat, Wild | 0 |
| Oilseed Rape | 5 |
| Pigweed | 65 |
| Ragweed | 5 |
| Ryegrass, Italian | 0 |
| Soybean | 60 |
| Velvetleaf | 40 |
| Waterhemp | 60 |
| Wheat | 5 |

What is claimed is:

1. A compound selected from Formula 1, N-oxides and salts thereof,

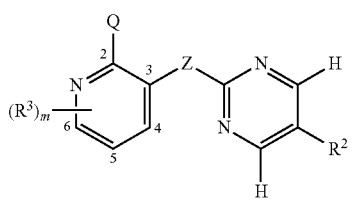

wherein

Q is selected from

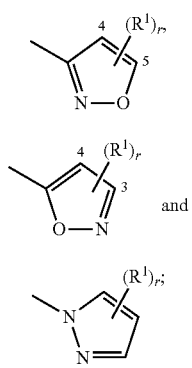

Z is O;
m is 0 or 1;
r is 1;
each $R^1$ is independently halogen, cyano, $C_1$-$C_4$ alkyl, $C_1$-$C_4$ haloalkyl, $C_1$-$C_4$ alkoxy, $C_1$-$C_4$ haloalkoxy or $SO_nR^{14}$;
n is 0, 1 or 2;
$R^2$ is halogen or $C_1$-$C_4$ alkyl;
each $R^3$ is independently halogen, cyano, $C_1$-$C_4$ alkyl, $C_2$-$C_4$ alkenyl, $C_2$-$C_4$ alkynyl, $C_1$-$C_4$ haloalkyl, $C_2$-$C_6$ alkylcarbonyl, $C_2$-$C_6$ haloalkylcarbonyl, $C_2$-$C_6$ alkoxycarbonyl, $C_1$-$C_4$ alkoxy, $C_1$-$C_4$ haloalkoxy, $C_2$-$C_6$ alkoxyalkyl or $C_2$-$C_6$ haloalkoxyalkyl; and
each $R^{14}$ is independently $C_1$-$C_4$ alkyl or $C_1$-$C_4$ haloalkyl.

2. The compound of claim 1 wherein
each $R^1$ is independently halogen, $C_1$-$C_4$ alkyl, $C_1$-$C_4$ haloalkyl or $C_1$-$C_4$ haloalkoxy;
$R^2$ is halogen or $CH_3$; and
each $R^3$ is independently halogen, cyano, $C_1$-$C_4$ alkyl or $C_1$-$C_4$ haloalkyl.

3. The compound of claim 1 selected from the group consisting of
2-[[2-(4-bromo-1H-pyrazol-1-yl)-3-pyridinyl]oxyl]-5-chloropyrimidine,
5-chloro-2-[[2-(4-chloro-1H-pyrazol-1-yl)-3-pyridinyl]oxy]pyrimidine,
5-chloro-2-[[2-[3-(difluoromethyl)-5-isoxazolyl]-3-pyridinyl]oxy]pyrimidine and
5-chloro-2-[[2-[5-(difluoromethyl)-3-isoxazolyl]-3-pyridinyl]oxy]pyrimidine.

4. A herbicidal composition comprising a compound of claim 1 and at least one component selected from the group consisting of surfactants, solid diluents and liquid diluents.

5. A herbicidal composition comprising a compound of claim 1, at least one additional active ingredient selected from the group consisting of other herbicides and herbicide safeners, and at least one component selected from the group consisting of surfactants, solid diluents and liquid diluents.

6. A herbicidal mixture comprising (a) a compound of claim 1, and (b) at least one additional active ingredient selected from (b1) photosystem II inhibitors, (b2) acetohydroxy acid synthase (AHAS) inhibitors, (b3) acetyl-CoA carboxylase (ACCase) inhibitors, (b4) auxin mimics, (b5) 5-enol-pyruvylshikimate-3-phosphate (EPSP) synthase inhibitors, (b6) photosystem I electron diverters, (b7) protoporphyrinogen oxidase (PPO) inhibitors, (b8) glutamine synthetase (GS) inhibitors, (b9) very long chain fatty acid (VLCFA) elongase inhibitors, (b10) auxin transport inhibitors, (b11) phytoene desaturase (PDS) inhibitors, (b12) 4-hydroxyphenyl-pyruvate dioxygenase (HPPD) inhibitors, (b13) homogentisate solanesyltransferase (HST) inhibitors, (b14) cellulose biosynthesis inhibitors, (b15) other herbicides including mitotic disruptors, organic arsenicals, asulam, bromobutide, cinmethylin, cumyluron, dazomet, difenzoquat, dymron, etobenzanid, flurenol, fosamine, fosamine-ammonium, hydantocidin, metam, methyldymron, oleic acid, oxaziclomefone, pelargonic acid and pyributicarb, (b16) herbicide safeners, and salts of compounds of (b1) through (b16).

7. A method for controlling the growth of undesired vegetation comprising contacting the vegetation or its environment with a herbicidally effective amount of a compound of claim 1.

8. The compound of claim 1 wherein
Q is

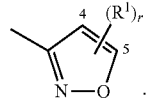

9. The compound of claim 8 wherein
each $R^1$ is independently halogen, $C_1$-$C_4$ alkyl, $C_1$-$C_4$ haloalkyl or $C_1$-$C_4$ haloalkoxy;
$R^2$ is halogen or $CH_3$; and
each $R^3$ is independently halogen, cyano, $C_1$-$C_4$ alkyl or $C_1$-$C_4$ haloalkyl.

10. The compound of claim 1 that is 5-chloro-2-[[2-[5-(difluoromethyl)-3-isoxazolyl]-3-pyridinyl]oxy]pyrimidine.

* * * * *